(12) United States Patent
Udagawa et al.

(10) Patent No.: US 8,263,381 B2
(45) Date of Patent: Sep. 11, 2012

(54) ENZYMES FOR STARCH PROCESSING

(75) Inventors: Hiroaki Udagawa, Yokohama (JP); Rikako Taira, Tokyo (JP); Shinobu Takagi, Funabashi Chiba (JP); Carsten Hjort, Vaerlose (DK); Anders Vikso-Nielsen, Slangerup (DK); Eric Allain, Wake Forest, NC (US); Shiro Fukuyama, Chiba (JP); Tomoko Matsui, Chiba (JP)

(73) Assignees: Novozyms A/S, Bagsvaerd (DK); Novozymes North America, Inc., Franklinton, NC (US)

(*) Notice: Subject to any disclaimer, the term of this patent is extended or adjusted under 35 U.S.C. 154(b) by 0 days.

(21) Appl. No.: 12/859,866

(22) Filed: Aug. 20, 2010

(65) Prior Publication Data

US 2010/0323061 A1 Dec. 23, 2010

Related U.S. Application Data

(63) Continuation of application No. 10/877,849, filed on Jun. 25, 2004, now Pat. No. 7,883,883.

(60) Provisional application No. 60/482,589, filed on Jun. 25, 2003, provisional application No. 60/490,751, filed on Jul. 29, 2003, provisional application No. 60/511,044, filed on Oct. 14, 2003, provisional application No. 60/514,854, filed on Oct. 27, 2003, provisional application No. 60/569,862, filed on May 10, 2004.

(30) Foreign Application Priority Data

| Jun. 25, 2003 | (DK) | 2003 00949 |
| Oct. 24, 2003 | (DK) | 2003 01568 |

(51) Int. Cl.
*C12N 9/26* (2006.01)
*C12N 9/24* (2006.01)
*A21D 2/00* (2006.01)
*C07H 21/04* (2006.01)

(52) U.S. Cl. ............ 435/201; 435/200; 435/99; 426/18; 426/20; 536/23.2; 536/23.4

(58) Field of Classification Search .............. 435/201, 435/200, 99; 426/18, 20; 536/23.2, 23.4
See application file for complete search history.

(56) References Cited

U.S. PATENT DOCUMENTS

| 4,009,074 | A | | 2/1977 | Walon |
| 4,591,560 | A | | 5/1986 | Kainuma |
| 4,727,026 | A | | 2/1988 | Sawada |
| 6,017,751 | A | * | 1/2000 | von der Osten et al. ...... 435/263 |
| 6,566,114 | B1 | | 5/2003 | Kauppinen et al. |
| 2003/0170634 | A1 | | 9/2003 | Callen et al. |
| 2005/0158839 | A1 | | 7/2005 | Borchert |

FOREIGN PATENT DOCUMENTS

| EP | 0 171 218 B1 | 10/1993 |
| WO | WO 98/14601 A1 | 4/1998 |
| WO | WO 98/16633 A1 | 4/1998 |
| WO | WO 98/22613 A1 | 5/1998 |
| WO | WO 00/77165 A2 | 12/2000 |
| WO | WO 03/012071 A2 | 2/2003 |
| WO | WO 03/018766 A3 | 3/2003 |
| WO | WO 2005/095624 A2 | 10/2005 |
| WO | WO 2006/069290 A2 | 6/2006 |
| WO | WO 2005/069840 A2 | 8/2006 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Nagasaka et al., Cloning of Corticium rolfsii glucoamyalse cDNA and its expression in *Saccharomyces cerevisiae*. Appl Microbiol Biotechnol., 1995, vol. 44: 451-458.*
Seffernick et al., Melamine deaminase and Atrazine chlorohydrolase: 98 percent identical but functionally different. J. Bacteriol.,2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Boel et al., The EMBO Journal, vol. 3, No. 7, pp. 1581-1585 (1984).
Brady et al., Biochemistry, vol. 29, pp. 6244-6249 (1990).
Guo et al., PNAS, vol. 101, No. 25, pp. 9205-9210 (2004).
Kaneko et al., Journal of Fermentation and Bioengineering, vol. 81, No. 4, pp. 292-298 (1996).
Kitamoto et al., Journal of Bacteriology, vol. 170, No. 12, pp. 5848-5854 (1998).
Matsuura et al., Journal of Biochemistry, vol. 95, No. 3, pp. 697-702 (1984).
Sogaard et al., Journal of Biological Chemistry, vol. 268, No. 30, pp. 22480-22484 (1993).
Yanagitani, Mari, "2D01A05—Creation of a Highly Efficient Starch-Degrading Amylase Using Starch-Bonding Domain Derived from *Bacillus sp* no195 strain" (2003).
Nagasaka et al., Appl. Microbiol. Biotechnol., vol. 50, No. 3, pp. 323-330 (1998).
Nagasaka et al, J. Appl. Glycosci., vol. 46, No. 2, pp. 169-178 (1999).
Joutsjoki et al., "Glucoamylase P Gene of Hormoconis Resinae: Molecular Cloning, Sequencing and Introduction Into Trichoderma Reesei", FEMS Microbiology Letters, vol. 99, pp. 237-244 (1992).
Sauer et al., "Glucoamylase: Structure/Function Relationships, and Protein Engineering", Biochimica et Biophysica Acta, vol. 1543, pp. 275-293 (2000).

* cited by examiner

*Primary Examiner* — Ganapathirama Raghu
(74) *Attorney, Agent, or Firm* — Elias Lambiris

(57) ABSTRACT

The present invention relates to a hybrid enzyme comprising carbohydrate-binding module amino acid sequence and a fungal alpha-amylase amino acid sequence and to a variant of a fungal wild type enzyme comprising a carbohydrate-binding module and an alpha-amylase catalytic module. The invention also relates to the use of the hybrid enzyme or the variant in starch liquefaction.

7 Claims, No Drawings

ENZYMES FOR STARCH PROCESSING

CROSS-REFERENCE TO RELATED APPLICATIONS

This application is a continuation of U.S. application Ser. No. 10/877,849 filed on Jun. 25, 2004, now U.S. Pat. No. 7,883,883, which claims the benefit or priority of Danish application nos. PA 2003 00949 and PA 2003 01568 filed Jun. 25, 2003 and Oct. 24, 2003, respectively, and U.S. provisional application nos. 60/482,589, 60/490,751, 60/511,044, 60/514,854, and 60/569,862 filed Jun. 25, 2003, Jul. 29, 2003, Oct. 14, 2003, Oct. 27, 2003, and May 10, 2004, respectively, the contents of which are fully incorporated herein by reference.

SEQUENCE LISTING

This application contains a Sequence Listing in computer readable form, which is incorporated herein by reference.

FIELD OF THE INVENTION

The present invention relates, inter alia, to an enzyme comprising a carbohydrate-binding module ("CBM") and an alpha-amylase catalytic domain. The enzyme may be a hybrid between a carbohydrate-binding module ("CBM") and an alpha-amylase or the enzyme may be a variant of a parent enzyme comprising a carbohydrate-binding module ("CBM") and an alpha-amylase catalytic domain. The invention also relates to the use of the enzyme in a starch liquefaction process in which starch is degraded to smaller oligo- and/or polysaccharide fragments.

BACKGROUND OF THE INVENTION

A large number of enzymes and processes have been described for converting starch to starch hydrolysates, such as maltose, glucose or specialty syrups, either for use as sweeteners or as precursors for other saccharides such as fructose. Glucose may also be fermented to ethanol or other fermentation products, such as citric acid, monosodium glutamate, gluconic acid, sodium gluconate, calcium gluconate, potassium gluconate, glucono delta lactone, or sodium erythorbate, itaconic acid, lactic acid, gluconic acid; ketones; amino acids, glutamic acid (sodium monoglutaminate), penicillin, tetracyclin; enzymes; vitamins, such as riboflavin, B12, beta-carotene or hormones.

Starch is a high molecular-weight polymer consisting of chains of glucose units. It usually consists of about 80% amylopectin and 20% amylose. Amylopectin is a branched polysaccharide in which linear chains of alpha-1,4 D-glucose residues are joined by alpha-1,6 glucosidic linkages.

Amylose is a linear polysaccharide built up of D-glucopyranose units linked together by alpha-1,4 glucosidic linkages. In the case of converting starch into a soluble starch hydrolysate, the starch is depolymerized. The conventional depolymerization process consists of a gelatinization step and two consecutive process steps, namely a liquefaction process and a saccharification process.

Granular starch consists of microscopic granules, which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typical industrial process, the starch has to be thinned or "liquefied" so that it can be handled. This reduction in viscosity is today mostly obtained by enzymatic degradation. During the liquefaction step, the long-chained starch is degraded into smaller branched and linear units (maltodextrins) by an alpha-amylase. The liquefaction process is typically carried out at about 105-110° C. for about 5 to 10 minutes followed by about 1-2 hours at about 95° C. The temperature is then lowered to 60° C., a glucoamylase or a beta-amylase and optionally a debranching enzyme, such as an isoamylase or a pullulanase are added, and the saccharification process proceeds for about 24 to 72 hours.

It will be apparent from the above discussion that the conventional starch conversion process is very energy consuming due to the different requirements in terms of temperature during the various steps. It is thus desirable to be able to select and/or design the enzymes used in the process so that the overall process can be performed without having to gelatinize the starch. Such processes are the subject of U.S. Pat. Nos. 4,591,560, 4,727,026 and 4,009,074 and EP 0171218, and Danish application no. PA 2003 00949. The present invention discloses a new hybrid enzyme and a genetic modification of a wild type enzyme designed for such processes and comprising an amino acid sequence of a CBM and an amino acid sequence of a fungal starch degrading enzyme. Hybrid enzymes are the subject of WO 98/14601, WO 00/77165 and Danish application no. PA 2003 00949.

SUMMARY OF THE INVENTION

The invention provides in a first aspect a hybrid enzyme which comprises an amino acid sequence of a catalytic module having alpha-amylase activity and an amino acid sequence of a carbohydrate-binding module, wherein the catalytic module is of fungal origin.

The invention provides in a second aspect a variant of the fungal alpha-amylase shown as SEQ ID NO:41 or variants of an alpha-amylase having at least 60% homology, at least 70% homology, at least 80% homology, or even at least 90% homology to SEQ ID NO:41, which variant comprising an alteration at one or more of the positions: 13, 15, 18, 31, 32, 33, 34, 35, 36, 61, 63, 64, 68, 69, 73, 74, 75, 76, 77, 78, 79, 80, 81, 82, 83, 84, 89, 117, 118, 119, 120, 121, 122, 123, 124, 125, 152, 153, 154, 155, 156, 157, 158, 161, 162, 165, 166, 167, 168, 169, 170, 171, 172, 173, 174, 175, 204, 205, 206, 207, 208, 209, 210, 211, 216, 229, 230, 231, 232, 233, 234, 235, 236, 237, 238, 239, 242, 245, 250, 252, 253, 255, 256, 257, 259, 260, 275, 292, 295, 296, 297, 298, 299, 304, 328, 339, 344, 348, 378, 383, 386, 387, 405, 448 and 480 wherein (a) the alteration(s) are independently, i) an insertion of an amino acid downstream of the amino acid which occupies the position, ii) a deletion of the amino acid which occupies the position, or iii) a substitution of the amino acid which occupies the position with a different amino acid, (b) the variant has increased acid alpha-amylase activity and or improved enzyme stability relative to the parent fungal alpha-amylase and, (c) each position corresponds to a position of the amino acid sequence of the TAKA amylase shown in SEQ ID NO:43 and/or the *A. kawachii* alpha-amylase shown as SEQ ID NO:41.

In further aspects the invention provides an isolated DNA sequence encoding the hybrid enzyme of the first aspect or the variant of the second aspect, a DNA construct comprising the DNA sequence encoding the hybrid enzyme of the first aspect or the variant of the second aspect, an expression vector comprising the DNA sequence encoding the hybrid enzyme of the first aspect or the variant of the second aspect, and a host cell transformed with a vector; which host cell is capable of expressing the DNA sequence encoding the hybrid enzyme of the first aspect or the variant of the second aspect.

In an eighth aspect the invention provides a method for liquefying starch, wherein a gelatinized or granular starch substrate is treated in aqueous medium with the hybrid enzyme of the first aspect or the variant of the second aspect.

DETAILED DESCRIPTION OF THE INVENTION

The term "granular starch" is understood as raw uncooked starch, i.e., starch that has not been subjected to a gelatinization. Starch is formed in plants as tiny granules insoluble in water. These granules are preserved in starches at temperatures below the initial gelatinization temperature. When put in cold water, the grains may absorb a small amount of the liquid. Up to 50° C. to 70° C. the swelling is reversible, the degree of reversibility being dependent upon the particular starch. With higher temperatures an irreversible swelling called gelatinization begins.

The term "initial gelatinization temperature" is understood as the lowest temperature at which gelatinization of the starch commences. Starch heated in water begins to gelatinize between 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch is the temperature at which birefringence is lost in 5% of the starch granules using the method described by Gorinstein and Lii, 1992, Starch/Stärke 44(12): 461-466.

The term "soluble starch hydrolysate" is understood as the soluble products of the processes of the invention and may comprise mono-, di-, and oligosaccharides, such as glucose, maltose, maltodextrins, cyclodextrins and any mixture of these. Preferably at least 90%, 91%, 92%, 93%, 94%, 95%, 96%, 97% or 98% of the dry solids of the granular starch is converted into a soluble starch hydrolysate.

The term polypeptide "homology" is understood as the degree of identity between two sequences indicating a derivation of the first sequence from the second. The homology may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman and Wunsch, 1970, *Journal of Molecular Biology* 48: 443-453. The following settings for amino acid sequence comparison are used: GAP creation penalty of 3.0 and GAP extension penalty of 0.1. The relevant part of the amino acid sequence for the homology determination is the mature polypeptide, i.e., without the signal peptide.

Hybrid Enzymes

Enzyme classification numbers (EC numbers) referred to in the present specification with claims are in accordance with the Recommendations of the Nomenclature Committee of the International Union of Biochemistry and Molecular Biology, Academic Press Inc, 1992.

Hybrid enzymes or a genetically modified wild type enzymes as referred to herein include species comprising an amino acid sequence of an alpha-amylolytic enzyme (EC 3.2.1.1) linked (i.e., covalently bound) to an amino acid sequence comprising a carbohydrate-binding module (CBM).

CBM-containing hybrid enzymes, as well as detailed descriptions of the preparation and purification thereof, are known in the art [see, e.g., WO 90/00609, WO 94/24158 and WO 95/16782, as well as Greenwood et al., 1994, *Biotechnology and Bioengineering* 44: 1295-1305]. They may, e.g., be prepared by transforming into a host cell a DNA construct comprising at least a fragment of DNA encoding the carbohydrate-binding module ligated, with or without a linker, to a DNA sequence encoding the enzyme of interest, and growing the transformed host cell to express the fused gene. The resulting recombinant product (hybrid enzyme)—often referred to in the art as a "fusion protein"—may be described by the following general formula:

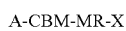

A-CBM-MR-X

In the latter formula, A-CBM is the N-terminal or the C-terminal region of an amino acid sequence comprising at least the carbohydrate-binding module (CBM) per se. MR is the middle region (the "linker"), and X is the sequence of amino acid residues of a polypeptide encoded by a DNA sequence encodng the enzyme (or other protein) to which the CBM is to be linked.

The moiety A may either be absent (such that A-CBM is a CBM per se, i.e., comprises no amino acid residues other than those constituting the CBM) or may be a sequence of one or more amino acid residues (functioning as a terminal extension of the CBM per se). The linker (MR) may be a bond, or a short linking group comprising from about 2 to about 100 carbon atoms, in particular of from 2 to 40 carbon atoms. However, MR is preferably a sequence of from about 2 to about 100 amino acid residues, more preferably of from 2 to 40 amino acid residues, such as from 2 to 15 amino acid residues.

The moiety X may constitute either the N-terminal or the C-terminal region of the overall hybrid enzyme.

It will thus be apparent from the above that the CBM in a hybrid enzyme of the type in question may be positioned C-terminally, N-terminally or internally in the hybrid enzyme.

Linker Sequence

The linker sequence may be any suitable linker sequence. In preferred embodiments the linker sequence is derived from the *Athelia rolfsii* AMG, the *A. niger* AMG or the *A. kawachii* alpha-amylase such as a linker sequence selected from the list consisting of *A. niger* AMG linker: T G G T T T T A T P T G S G S V T S T S K T T A T A S K T S T S T S S T S A (SEQ ID NO:26), *A. kawachii* alpha-amylase linker: T T T T T T A A A T S T S K A T T S S S S S S A A A T T S S S (SEQ ID NO:27), *Athelia rolfsii* AMG linker: G A T S P G G S S G S (SEQ ID NO:28), and the PEPT linker: P E P T P E P T (SEQ ID NO:29). In another preferred embodiment the hybrid enzyme has a linker sequence which differs from the amino acid sequence shown in SEQ ID NO:26, SEQ ID NO:27, SEQ ID NO:28, or SEQ ID NO:29 in no more than 10 positions, no more than 9 positions, no more than 8 positions, no more than 7 positions, no more than 6 positions, no more than 5 positions, no more than 4 positions, no more than 3 positions, no more than 2 positions, or even no more than 1 position.

Carbohydrate-Binding Modules

A carbohydrate-binding module (CBM), or as often referred to, a carbohydrate-binding domain (CBD), is a polypeptide amino acid sequence which binds preferentially to a poly- or oligosaccharide (carbohydrate), frequently—but not necessarily exclusively—to a water-insoluble (including crystalline) form thereof.

CBMs derived from starch degrading enzymes are often referred to as starch-binding modules or SBMs (CBMs which may occur in certain amylolytic enzymes, such as certain glucoamylases, or in enzymes such as cyclodextrin glucanotransferases, or in alpha-amylases). Likewise, other subclasses of CBMs would embrace, e.g., cellulose-binding modules (CBMs from cellulolytic enzymes), chitin-binding modules (CBMs which typically occur in chitinases), xylan-binding modules (CBMs which typically occur in xylanases), mannan-binding modules (CBMs which typically occur in mannanases). SBMs are often referred to as SBDs (Starch Binding Domains).

CBMs are found as integral parts of large polypeptides or proteins consisting of two or more polypeptide amino acid sequence regions, especially in hydrolytic enzymes (hydrolases) which typically comprise a catalytic module containing the active site for substrate hydrolysis and a carbohydrate-binding module (CBM) for binding to the carbohydrate substrate in question. Such enzymes can comprise more than one catalytic module and one, two or three CBMs, and optionally further comprise one or more polypeptide amino acid sequence regions linking the CBM(s) with the catalytic module(s), a region of the latter type usually being denoted a "linker". Examples of hydrolytic enzymes comprising a CBM—some of which have already been mentioned above—are cellulases, xylanases, mannanases, arabinofuranosidases, acetylesterases and chitinases. CBMs have also been found in algae, e.g., in the red alga *Porphyra purpurea* in the form of a non-hydrolytic polysaccharide-binding protein.

In proteins/polypeptides in which CBMs occur (e.g., enzymes, typically hydrolytic enzymes), a CBM may be located at the N or C terminus or at an internal position.

That part of a polypeptide or protein (e.g., hydrolytic enzyme) which constitutes a CBM per se typically consists of more than about 30 and less than about 250 amino acid residues.

The "Carbohydrate-Binding Module of Family 20" or a CBM-20 module is in the context of this invention defined as a sequence of approximately 100 amino acids having at least 45% homology to the Carbohydrate-Binding Module (CBM) of the polypeptide disclosed in FIG. 1 by Joergensen et al., 1997, *Biotechnol. Lett.* 19: 1027-1031. The CBM comprises the last 102 amino acids of the polypeptide, i.e., the subsequence from amino acid 582 to amino acid 683. The numbering of Glycoside Hydrolase Families applied in this disclosure follows the concept of Coutinho and Henrissat, 1999, *CAZy—Carbohydrate-Active Enzymes server* at URL: afmb.cnrs-mrs.fr/~cazy/CAZY/index.html or alternatively Coutinho and Henrissat, 1999, The modular structure of cellulases and other carbohydrate-active enzymes: an integrated database approach. In "*Genetics, Biochemistry and Ecology of Cellulose Degradation*", Ohmiya, Hayashi, Sakka, Kobayashi, Karita and Kimura eds., Uni Publishers Co., Tokyo, pp. 15-23, and Bourne and Henrissat, 2001, Glycoside hydrolases and glycosyltransferases: families and functional modules, *Current Opinion in Structural Biology* 11: 593-600.

Examples of enzymes which comprise a CBM suitable for use in the context of the invention are alpha-amylases, maltogenic alpha-amylases, cellulases, xylanases, mannanases, arabinofuranosidases, acetylesterases and chitinases. Further CBMs of interest in relation to the present invention include CBMs deriving from glucoamylases (EC 3.2.1.3) or from CGTases (EC 2.4.1.19).

CBMs deriving from fungal, bacterial or plant sources will generally be suitable for use in the context of the invention. Preferred are CBMs of fungal origin, more preferably from *Aspergillus* sp., *Bacillus* sp., *Klebsiella* sp., or *Rhizopus* sp. In this connection, techniques suitable for isolating the relevant genes are well known in the art.

Preferred for the invention is CBMs of Carbohydrate-Binding Module Family 20. CBMs of Carbohydrate-Binding Module Family 20 suitable for the invention may be derived from glucoamylases of *Aspergillus awamori* (SWISSPROT Q12537), *Aspergillus kawachii* (SWISSPROT P23176), *Aspergillus niger* (SWISSPROT P04064), *Aspergillus oryzae* (SWISSPROT P36914), from alpha-amylases of *Aspergillus kawachii* (EMBL:#AB008370), *Aspergillus nidulans* (NCBI AAF17100.1), from beta-amylases of *Bacillus cereus* (SWISSPROT P36924), or from CGTases of *Bacillus circulans* (SWISSPROT P43379). Preferred is a CBM from the alpha-amylase of *Aspergillus kawachii* (EMBL:#AB008370) as well as CBMs having at least 50%, 60%, 70%, 80% or even at least 90% homology to the CBM of the alpha-amylase of *Aspergillus kawachii* (EMBL:#AB008370), i.e., a CBM having at least 50%, 60%, 70%, 80% or even at least 90% homology to the amino acid sequence of SEQ ID NO:6. Also preferred for the invention are the CBMs of Carbohydrate-Binding Module Family 20 having the amino acid sequences shown in SEQ ID NO:9, SEQ ID NO:10, and SEQ ID NO:11 and disclosed in Danish application no. PA 2003 00949 as SEQ ID NO:1, SEQ ID NO:2 and SEQ ID NO:3 respectively. Further preferred CBMs include the CBMs of the glucoamylase from *Hormoconis* sp. such as from *Hormoconis resinae* (Syn. Creosote fungus or *Amorphotheca resinae*) such as the CBM of SWISSPROT:Q03045 (SEQ ID NO:12), from *Lentinula* sp. such as from *Lentinula edodes* (shiitake mushroom) such as the CBM of SPTREMBL:Q9P4C5 (SEQ ID NO:13), from *Neurospora* sp. such as from *Neurospora crassa* such as the CBM of SWISSPROT:P14804 (SEQ ID NO:14), from *Talaromyces* sp. such as from *Talaromyces byssochlamydioides* such as the CBM of NN005220 (SEQ ID NO:15), from *Geosmithia* sp. such as from *Geosmithia cylindrospora*, such as the CBM of NN48286 (SEQ ID NO:16), from *Scorias* sp. such as from *Scorias spongiosa* such as the CBM of NN007096 (SEQ ID NO:17), from *Eupenicillium* sp. such as from *Eupenicillium ludwigii* such as the CBM of NN005968 (SEQ ID NO:18), from *Aspergillus* sp. such as from *Aspergillus japonicus* such as the CBM of NN001136 (SEQ ID NO:19), from *Penicillium* sp. such as from *Penicillium* cf. *miczynskii* such as the CBM of NN48691 (SEQ ID NO:20), from Mz1 *Penicillium* sp. such as the CBM of NN48690 (SEQ ID NO:21), from *Thysanophora* sp. such as the CBM of NN48711 (SEQ ID NO:22), and from *Humicola* sp. such as from *Humicola grisea* var. *thermoidea* such as the CBM of SPTREMBL:Q12623 (SEQ ID NO:23). Most preferred CBMs include the CBMs of the glucoamylase from *Aspergillus* sp. such as from *Aspergillus niger*, such as SEQ ID NO:24, and *Athelia* sp. such as from *Athelia rolfsii*, such as SEQ ID NO:25. Also preferred for the invention is any CBD having at least 50%, 60%, 70%, 80% or even at least 90% homology to any of the afore mentioned CBD amino acid sequences.

Further suitable CBMs of Carbohydrate-Binding Module Family 20 may be found at URL: afmb.cnrs-mrs.fr/~cazy/CAZY/index.html).

Once a nucleotide sequence encoding the substrate-binding (carbohydrate-binding) region has been identified, either as cDNA or chromosomal DNA, it may then be manipulated in a variety of ways to fuse it to a DNA sequence encoding the enzyme of interest. The DNA fragment encoding the carbohydrate-binding amino acid sequence, and the DNA encoding the enzyme of interest are then ligated with or without a linker. The resulting ligated DNA may then be manipulated in a variety of ways to achieve expression.

Alpha-Amylolytic Sequence

Alpha-amylases (in particular acid stable alpha-amylases) which are appropriate as the basis for CBM/amylase hybrids of the types employed in the context of the present invention include those of fungal origin.

Preferably the alpha-amylase is a wild type enzyme. More preferably the alpha-amylase is a variant alpha-amylases comprising amino acid modifications leading to increased activity, increased protein stability at low pH, and/or at high pH, increased stability towards calcium depletion, and/or increased stability at elevated temperature. Chemically or genetically modified mutants of such alpha-amylases are included in this connection.

Relevant alpha-amylases include, for example, alpha-amylases obtainable from *Aspergillus* species, in particular from *Aspergillus niger*, such as an acid stable alpha-amylase (SWISSPROT P56271), described in more detail in WO 8901969 (example 3) and having the amino acid sequence shown in SEQ ID NO:8 and/or encode by the DNA sequence shown in SEQ ID NO:7. Also preferred are alpha-amylase sequences having more than 50%, such as 60%, or 70%, 80% or 90% homology to the amino acid sequence shown in SEQ ID NO:8 and/or encode by the DNA sequence shown in SEQ ID NO:7.

In another preferred embodiment the alpha-amylolytic sequence is derived from the *A. oryzae* acid alpha-amylase (Fungamyl™). More preferably the alpha-amylolytic sequence has more than 50%, such as 60%, or 70%, 80% or 90% homology to the amino acid sequence shown in SEQ ID NO:30 and/or to the sequence shown as amino acids 21-498 of the amino acid sequence shown in SEQ ID NO:30.

Even more preferred is an embodiment wherein the hybrid enzyme comprises an alpha-amylolytic sequence derived from the *A. oryzae* acid alpha-amylase (Fungamyl™, SEQ ID NO:30), and/or a linker sequence derived from the *A. kawachii* alpha-amylase or the *A. rolfsii* AMG, and/or a CBM derived from the *A. kawachii* alpha-amylase (SEQ ID NO:5) or the *A. rolfsii* AMG (SEQ ID NO:25). In a particular such embodiment the hybrid enzyme has the amino acid sequence shown in SEQ ID NO:36 or in SEQ ID NO:40.

Also preferred is an embodiment wherein the hybrid enzyme comprises an alpha-amylolytic sequence derived from the *A. niger* acid alpha-amylase catalytic module having the sequence shown in SEQ ID NO:8, and/or a linker sequence derived from the *A. kawachii* alpha-amylase or the *A. rolfsii* AMG, and/or the CBM is derived from the *A. kawachii* alpha-amylase, the *A. rolfsii* AMG or the *A. niger* AMG. In a particularly preferred embodiment the hybrid enzyme comprises the *A. niger* acid alpha-amylase catalytic module having the sequence shown in SEQ ID NO:8 and the *A. kawachii* alpha-amylase linker and CBM (SEQ ID NO:6).

Preferably the hybrid enzyme comprises a CBD sequence having at least 50%, 60%, 70%, 80% or even at least 90% homology to any of the amino acid sequences shown in SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24 or SEQ ID NO:25. Even more preferred the hybrid enzyme comprises a CBD sequence having an amino acid sequence shown in SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24 or SEQ ID NO:25. In yet another preferred embodiment the CBM sequence has an amino acid sequence which differs from the amino acid sequence amino acid sequence shown in SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24 or SEQ ID NO:25 in no more than 10 amino acid positions, no more than 9 positions, no more than 8 positions, no more than 7 positions, no more than 6 positions, no more than 5 positions, no more than 4 positions, no more than 3 positions, no more than 2 positions, or even no more than 1 position. In a most preferred embodiment the hybrid enzyme comprises a CBM derived from an AMG from *A. rolfsii*, such as the AMG from *A. rolfsii* AHU 9627 described in U.S. Pat. No. 4,727,026.

In a particular embodiment the hybrid enzyme has the amino acid sequence shown in SEQ ID NO:32, SEQ ID NO:34 or SEQ ID NO:38 or the hybrid enzyme has an amino acid sequence having at least 50%, 60%, 70%, 80% or even at least 90% homology to any of the aforementioned amino acid sequences.

In yet another preferred embodiment the hybrid enzyme has an amino acid sequence which differs from the amino acid sequence amino acid sequence shown in SEQ ID NO:32, SEQ ID NO:34, SEQ ID NO:36, SEQ ID NO:38 or SEQ ID NO:40 in no more than 10 positions, no more than 9 positions, no more than 8 positions, no more than 7 positions, no more than 6 positions, no more than 5 positions, no more than 4 positions, no more than 3 positions, no more than 2 positions, or even no more than 1 position.

In a preferred embodiment the hybrid enzyme is a variant comprises the catalytic domain shown as amino acids 21-498 of SEQ ID NO:40 (and/or amino acids 21-498 of SEQ ID NO:30) with one or more substitutions, more preferably a substitution in one or more positions selected from the list consisting of: 81, 158, 161, 163, 164, 175, 176, 177, 253, 264, 266, 466, 468, 470, and most preferably one or more substitutions selected from the list consisting of: □81R, K158D, K158V, S161 D, S161 N, Q163S, Q163A, D164S, Y175W, E176D, D177N, D253N,N264K, N264E, M266L, G466D, D468S, and N470D. In an even more preferred embodiment the hybrid enzyme is one of the variants listed in Table 6. Also preferred are variants comprising the catalytic domain shown as amino acids 21-498 of SEQ ID NO:40 (and/or amino acids 21-498 of SEQ ID NO:30) with one or more substations or combination of substitutions selected from the list comprising: Y175W+E176D, 276W+P277Q, K380T+L381W, G62N, G62F, Y95D, D106K+S109D, A140P, K158D+D164S, F171L+E182Q, K200E+V202A, K200E+V202A, K200E+V202A, T227S+K233P, L252D+D255N, N264K+M266L, K283E, N359K+D360V, N390K+Y391L, G466D+N470D, Y484L+S498S, Y484L+S498G. and Y484L+S498R.

In a preferred embodiment the hybrid enzyme comprises the catalytic module according shown as amino acids 21-498 of SEQ ID NO:40 (and/or amino acids 21-498 of SEQ ID NO:30) with one or more substitutions selected from the list consisting of: K158V, S161 N, Q163A, D164S, N264K, M266L, G466D, D468S and N470D.

In another preferred embodiment the hybrid enzyme comprises the catalytic module shown as amino acids 21-498 of SEQ ID NO:40 (and/or amino acids 21-498 of SEQ ID NO:30) with one or more substitutions selected from the list consisting of: □81R, K158V, S161 N, Q163A, D164S, Y175W, E176D, D177N, N264K, M266L, G466D, D468S and N470D.

Expression Vectors

The present invention also relates to recombinant expression vectors which may comprise a DNA sequence encoding the hybrid enzyme or a genetically modified wild type enzyme, a promoter, a signal peptide sequence, and transcriptional and translational stop signals. The various DNA and control sequences described above may be joined together to produce a recombinant expression vector which may include one or more convenient restriction sites to allow for insertion or substitution of the DNA sequence encoding the polypeptide at such sites. Alternatively, the DNA sequence of the present invention may be expressed by inserting the DNA sequence or a DNA construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus), which can be conveniently subjected to recombinant DNA procedures and can bring about the expression of the DNA sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, a cosmid or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

Markers

The vectors of the present invention preferably contain one or more selectable markers, which permit easy selection of transformed cells. A selectable marker is a gene the product of which provides for biocide or viral resistance, resistance to heavy metals, prototrophy to auxotrophs, and the like.

Examples of selectable markers for use in a filamentous fungus host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. Preferred for use in an *Aspergillus* cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243, where the selectable marker is on a separate vector.

The vectors of the present invention preferably contain an element(s) that permits stable integration of the vector into the host cell genome or autonomous replication of the vector in the cell independent of the genome of the cell.

The vectors of the present invention may be integrated into the host cell genome when introduced into a host cell. For integration, the vector may rely on the DNA sequence encoding the polypeptide of interest or any other element of the vector for stable integration of the vector into the genome by homologous or none homologous recombination. Alternatively, the vector may contain additional DNA sequences for directing integration by homologous recombination into the genome of the host cell. The additional DNA sequences enable the vector to be integrated into the host cell genome at a precise location(s) in the chromosome(s). To increase the likelihood of integration at a precise location, the integrational elements should preferably contain a sufficient number of DNAs, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding DNA sequences. On the other hand, the vector may be integrated into the genome of the host cell by non-homologous recombination. These DNA sequences may be any sequence that is homologous with a target sequence in the genome of the host cell, and, furthermore, may be non-encoding or encoding sequences.

For autonomous replication, the vector may further comprise an origin of replication enabling the vector to replicate autonomously in the host cell in question.

The episomal replicating the AMA1 plasmid vector disclosed in WO 00/24883 may be used.

More than one copy of a DNA sequence encoding a polypeptide of interest may be inserted into the host cell to amplify expression of the DNA sequence. Stable amplification of the DNA sequence can be obtained by integrating at least one additional copy of the sequence into the host cell genome using methods well known in the art and selecting for transformants.

The procedures used to ligate the elements described above to construct the recombinant expression vectors of the present invention are well known to one skilled in the art (see, e.g., Sambrook et al, 1989, Molecular Cloning, A Laboratory Manual, $2^{nd}$ edition, Cold Spring Harbor, N.Y.).

Host Cells

The host cell of the invention, either comprising a DNA construct or an expression vector comprising the DNA sequence encoding the hybrid enzyme or a genetically modified wild type enzyme, is advantageously used as a host cell in the recombinant production of the hybrid enzyme or a genetically modified wild type enzyme. The cell may be transformed with an expression vector. Alternatively, the cell may be transformed with the DNA construct of the invention encoding the hybrid enzyme or a genetically modified wild type enzyme, conveniently by integrating the DNA construct (in one or more copies) in the host chromosome. Integration of the DNA construct into the host chromosome may be performed according to conventional methods, e.g., by homologous or heterologous recombination.

The host cell may be any appropriate prokaryotic or eukaryotic cell, e.g., a bacterial cell, a filamentous fungus cell, a plant cell or a mammalian cell.

In a preferred embodiment, the host cell is a filamentous fungus represented by the following groups of Ascomycota, include, e.g., *Neurospora, Eupenicillium* (=*Penicillium*), *Emericella* (=*Aspergillus*), *Eurotium* (=*Aspergillus*).

In a more preferred embodiment, the filamentous fungus include all filamentous forms of the subdivision Eumycota and Oomycota (as defined by Hawksworth et al. In, *Ainsworth and Bisby's Dictionary of The Fungi*, $8^{th}$ edition, 1995, CAB International, University Press, Cambridge, UK. The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic.

In an even more preferred embodiment, the filamentous fungus host cell is a cell of a species of, but not limited to a cell selected from the group consisting of a strain belonging to a species of *Aspergillus*, preferably *Aspergillus oryzae*,

*Aspergillus niger, Aspergillus awamori, Aspergillus kawachii*, or a strain of *Bacillus*, or a strain of *Fusarium*, such as a strain of *Fusarium oxysporium, Fusarium graminearum* (in the perfect state named *Gribberella zeae*, previously *Sphaeria zeae*, synonym with *Gibberella roseum* and *Gibberella roseum* f. sp. *cerealis*), or *Fusarium sulphureum* (in the prefect state named *Gibberella puricaris*, synonym with *Fusarium trichothecioides, Fusarium bactridioides, Fusarium sambucium, Fusarium roseum*, and *Fusarium roseum* var. *graminearum*), *Fusarium cerealis* (synonym with *Fusarium crookwellense*), or *Fusarium venenatum*.

In a most preferred embodiment, the filamentous fungus host cell is a cell of a strain belonging to a species of *Aspergillus*, preferably *Aspergillus oryzae* or *Aspergillus niger*.

The host cell may be a wild type filamentous fungus host cell or a variant, a mutant or a genetically modified filamentous fungus host cell. In a preferred embodiment of the invention the host cell is a protease deficient or protease minus strain. Also specifically contemplated is *Aspergillus* strains, such as *Aspergillus niger* strains, genetically modified to disrupt or reduce expression of glucoamylase, acid-stable alpha-amylase, alpha-1,6 transglucosidase, and protease activities.

Transformation of Filamentous Fungus Host Cells

Filamentous fungus host cells may be transformed by a process involving protoplast formation, transformation of the protoplasts, and regeneration of the cell wall in a manner known in the art. Suitable procedures for transformation of *Aspergillus* host cells are described in EP 238 023, EP 184 438, and Yelton et al., 1984, *Proceedings of the National Academy of Sciences USA* 81:1470-1474. A suitable method of transforming *Fusarium* species is described by Malardier et al., 1989, *Gene* 78:147-156 or U.S. Pat. No. 6,060,305.

Isolating and Cloning a DNA Sequence Encoding a Parent Alpha-Amylase

The techniques used to isolate or clone a DNA sequence encoding a polypeptide of interest are known in the art and include isolation from genomic DNA, preparation from cDNA, or a combination thereof. The cloning of the DNA sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other DNA amplification procedures such as ligase chain reaction (LCR), ligated activated transcription (LAT) and DNA sequence-based amplification (NASBA) may be used.

The DNA sequence encoding a parent alpha-amylase may be isolated from any cell or microorganism producing the alpha-amylase in question, using various methods well known in the art. First, a genomic DNA and/or cDNA library should be constructed using chromosomal DNA or messenger RNA from the organism that produces the alpha-amylase to be studied. Then, if the amino acid sequence of the alpha-amylase is known, labeled oligonucleotide probes may be synthesized and used to identify alpha-amylase-encoding clones from a genomic library prepared from the organism in question. Alternatively, a labelled oligonucleotide probe containing sequences homologous to another known alpha-amylase gene could be used as a probe to identify alpha-amylase-encoding clones, using hybridization and washing conditions of very low to very high stringency.

Yet another method for identifying alpha-amylase-encoding clones would involve inserting fragments of genomic DNA into an expression vector, such as a plasmid, transforming alpha-amylase-negative bacteria with the resulting genomic DNA library, and then plating the transformed bacteria onto agar containing a substrate for alpha-amylase (i.e., maltose), thereby allowing clones expressing the alpha-amylase to be identified.

Alternatively, the DNA sequence encoding the enzyme may be prepared synthetically by established standard methods, e.g., the phosphoroamidite method described in Beaucage and Caruthers, 1981, *Tetrahedron Letters* 22: 1859-1869, or the method described by Matthes et al., 1984, *EMBO J.* 3: 801-805. In the phosphoroamidite method, oligonucleotides are synthesized, e.g., in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or Saiki et al., 1988, *Science* 239: 487-491.

Isolated DNA Sequence

The present invention relates, inter alia, to an isolated DNA sequence comprising a DNA sequence encoding a hybrid enzyme or a genetically modified wild type enzyme comprising an amino acid sequence of a catalytic module having alpha-amylase activity and an amino acid sequence of a carbohydrate-binding module, wherein the catalytic module is of fungal origin.

The term "isolated DNA sequence" as used herein refers to a DNA sequence, which is essentially free of other DNA sequences, e.g., at least about 20% pure, preferably at least about 40% pure, more preferably at least about 60% pure, even more preferably at least about 80% pure, and most preferably at least about 90% pure as determined by agarose electrophoresis.

For example, an isolated DNA sequence can be obtained by standard cloning procedures used in genetic engineering to relocate the DNA sequence from its natural location to a different site where it will be reproduced. The cloning procedures may involve excision and isolation of a desired DNA fragment comprising the DNA sequence encoding the polypeptide of interest, insertion of the fragment into a vector molecule, and incorporation of the recombinant vector into a host cell where multiple copies or clones of the DNA sequence will be replicated. An isolated DNA sequence may be manipulated in a variety of ways to provide for expression of the polypeptide of interest. Manipulation of the DNA sequence prior to its insertion into a vector may be desirable or necessary depending on the expression vector. The techniques for modifying DNA sequences utilizing recombinant DNA methods are well known in the art.

DNA Construct

The present invention relates, inter alia, to a DNA construct comprising a DNA sequence encoding a hybrid enzyme or a genetically modified wild type enzyme comprising an amino acid sequence of a catalytic module having alpha-amylase activity and an amino acid sequence of a carbohydrate-binding module, wherein the catalytic module is of fungal origin. "DNA construct" is defined herein as a DNA molecule, either single- or double-stranded, which is isolated from a naturally occurring gene or which has been modified to contain segments of DNA, which are combined and juxtaposed in a manner, which would not otherwise exist in nature. The term DNA construct is synonymous with the term expression cassette when the DNA construct contains all the control sequences required for expression of a coding sequence of the present invention.

Site-Directed Mutagenesis

Once a parent alpha-amylase-encoding DNA sequence has been isolated, and desirable sites for mutation identified, mutations may be introduced using synthetic oligonucleotides. These oligonucleotides contain nucleotide sequences flanking the desired mutation sites. In a specific method, a single-stranded gap of DNA, the alpha-amylase-encoding sequence, is created in a vector carrying the alpha-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., 1984, *Biotechnology* 2: 646-639. U.S. Pat. No. 4,760,025 discloses the introduction of oligo-nucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into alpha-amylase-encoding DNA sequences is described in Nelson and Long, 1989, *Analytical Biochemistry* 180: 147-151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Localized Random Mutagenesis

The random mutagenesis may be advantageously localized to a part of the parent alpha-amylase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

Variants of Hybrid or Wild Type Enzymes

The performance in a starch degradation process of a wild type or hybrid enzyme comprising a carbohydrate-binding module ("CBM") and an alpha-amylase catalytic module may be improved through protein engineering, such as by site directed mutagenesis, by localized random mutagenesis, by synthetically preparing a new variant of the parent wild type enzyme or parent hybrid enzyme, or by any other suitable protein engineering techniques.

Parent alpha-amylase contemplated for the invention include wild-type fungal alpha-amylase having a CBM, in particular fungal alpha-amylase obtainable from an *Aspergillus* strain, such as an *Aspergillus kawachii* acid alpha-amylase and variants or mutants thereof, homologous alpha-amylases, and further wild type or artificial alpha-amylases being structurally and/or functionally similar to the acid alpha-amylase from *Aspergillus kawachii* shown in SEQ ID NO:41.

While the acid alpha-amylase from *Aspergillus kawachii* is an example of a wild type alpha-amylase comprising a carbohydrate-binding module ("CBM"), the *Aspergillus kawachii* acid alpha-amylase catalytic module has a limited specific activity, e.g., compared to the catalytic activity of the acid alpha-amylase from *A. niger*. Furthermore, the CBM of the *Aspergillus kawachii* alpha-amylase is easily cleaved off from the catalytic module during a conventional fermentation process thereby reducing the suitability of the enzyme for industrial application. Thus the *Aspergillus kawachii* alpha-amylase has several serious drawbacks as an industrial enzyme for raw starch hydrolysis. Protein engineering techniques can be applied to yield more suitable variants of a parent acid alpha-amylase wherein the catalytic activity and/or the enzyme stability has been improved.

Preferred variants are variants of the fungal alpha-amylase shown as SEQ ID NO:41 or variants of an alpha-amylase having at least 60% homology, at least 70% homology, at least 80% homology, or even at least 90% homology to SEQ ID NO:41, which variant comprising an alteration at one or more of the positions: 13, 15, 18, 31, 32, 33, 34, 35, 36, 61, 63, 64, 68, 69, 73, 74, 75, 76, 77, 78, 79, 80, 81, 82, 83, 84, 89, 117, 118, 119, 120, 121, 122, 123, 124, 125, 152, 153, 154, 155, 156, 157, 158, 161, 162, 165, 166, 167, 168, 169, 170, 171, 172, 173, 174, 175, 204, 205, 206, 207, 208, 209, 210, 211, 216, 229, 230, 231, 232, 233, 234, 235, 236, 237, 238, 239, 242, 245, 250, 252, 253, 255, 256, 257, 259, 260, 275, 292, 295, 296, 297, 298, 299, 304, 328, 339, 344, 348, 378, 383, 386, 387, 405, 448 and 480 and more preferred at one or more of the positions 31, 33, 36, 74, 75, 77, 84, 120, 153, 154, 155, 156, 157, 158, 162, 166, 169, 170, 199, 232, 233, 235, 238, 239, 245, 256, 257, 331, 336, 339, 340, 342, 348, 378, 383, 386, 387, 405, 448 and 480 wherein (a) the alteration(s) are independently (i) an insertion of an amino acid downstream of the amino acid which occupies the position, (ii) a deletion of the amino acid which occupies the position, or iii) a substitution of the amino acid which occupies the position with a different amino acid, (b) the variant has increased acid alpha-amylase activity and or improved enzyme stability relative to the parent fungal alpha-amylase and (c) each position corresponds to a position of the amino acid sequence of the TAKA amylase shown in SEQ ID NO:43 and/or the *A. kawachii* alpha-amylase shown as SEQ ID NO:41.

More preferred variants are variants of the *A. kawachii* alpha-amylase shown as SEQ ID NO:41 or variants of an alpha-amylase having at least 60% homology, at least 70% homology, at least 80% homology, or even at least 90% homology to SEQ ID NO:41 and comprising alterations in one or more of the following positions: 13, 15, 18, 31, 32, 33, 34, 35, 36, 61, 63, 64, 68, 69, 73, 74, 75, 76, 77, 78, 79, 80, 81, 82, 83, 84, 89, 117, 118, 119, 120, 121, 122, 123, 124, 125, 152, 153, 154, 155, 156, 157, 158, 161, 162, 165, 166, 167, 168, 169, 170, 171, 172, 173, 174, 175, 204, 205, 206, 207, 208, 209, 210, 211, 216, 229, 230, 231, 232, 233, 234, 235, 236, 237, 238, 239, 242, 245, 250, 252, 253, 255, 256, 257, 259, 260, 275, 292, 295, 296, 297, 298, 299, 304, 328, 339, 344, 348, 378, 383, 386, 387, 405, 448 and 480 wherein (a) the alteration(s) are independently (i) an insertion of an amino acid downstream of the amino acid which occupies the position, (ii) a deletion of the amino acid which occupies the position, or iii) a substitution of the amino acid which occupies the position with a different amino acid, (b) the variant has increased acid alpha-amylase activity and or improved enzyme stability relative to the parent fungal alpha-amylase and (c) each position corresponds to a position of the amino acid sequence of the TAKA amylase shown in SEQ ID NO:43 and/or the *A. kawachii* alpha-amylase shown as SEQ ID NO:41. Even more preferred variants of the *A. kawachii* alpha-amylase shown as SEQ ID NO:41 or variants of an alpha-amylase having at least 60% homology, at least 70% homology, at least 80% homology, or even at least 90% homology to SEQ ID NO:41 and comprising alterations in one or more of the following positions: 31, 33, 36, 74, 75, 77, 84, 120, 153, 154, 155, 156, 157, 158, 162, 166, 169, 170, 199, 232, 233, 235, 238, 239, 245, 256, 257, 331, 336, 339, 340, 342, 348, 378, 383, 386, 387, 405, 448 and 480.

Yet more preferred are variants of the *A. kawachii* alpha-amylase shown as SEQ ID NO: 41 or variants of an alpha-amylase having at least 60% homology, at least 70% homology, at least 80% homology, or even at least 90% homology to SEQ ID NO: 41 comprising one or more of the following amino acid substitution: G33A, I36K, S74A, D75Y, E77D, P120A, I153D, D154N, W155Y, D156E, N157D, L158Q, Q162E, E166L, T169N, I170T, E199K, E199L, D232L, N233D, N235D, L238Y, D239T, W256Y, Q257P, E331Q, S336A, D339K, D339N, V340D, and Y342A, and most preferred variants comprises one or more of the following amino acid substitution S74A, E166L, E199L, D339K, and D156E, such as the variant comprising the multiple amino acid substitution: S74A/E166L/E199L, wherein the variant has improve activity and/or enzyme stability relative to the parent alpha-amylase shown as SEQ ID NO:41.

The variants may also be a variants of the *A. kawachii* alpha-amylase shown as SEQ ID NO:41 or variants of an alpha-amylase having at least 60% homology, at least 70% homology, at least 80% homology, or even at least 90% homology to SEQ ID NO:41 and comprising alterations in one or more of the following positions: 31, 74, 89, 209, 245, 348, 378, 383, 386, 387, 405, 448, and 480, wherein (a) the alteration(s) are independently (i) an insertion of an amino acid downstream of the amino acid which occupies the position, (ii) a deletion of the amino acid which occupies the position, or iii) a substitution of the amino acid which occupies the position with a different amino acid, (b) the variant has increased acid alpha-amylase activity and or improved enzyme stability relative to the parent fungal alpha-amylase.

Preferably the variants is a variants of the *A. kawachii* alpha-amylase shown as SEQ ID NO:41 or variants of an alpha-amylase having at least 60% homology, at least 70% homology, at least 80% homology, or even at least 90% homology to SEQ ID NO:41 and comprising one or more of the following substitutions: N31D, S74A, Y89D, E209L, Y245V, D348K, D378A, K383A, P386A, I387F, I405V, N448S, and N480R, wherein the variant has increased acid alpha-amylase activity and or improved enzyme stability relative to the parent fungal alpha-amylase shown as SEQ ID NO:41.

Most preferred is a variants of the *A. kawachii* alpha-amylase shown as SEQ ID NO:41 and comprising the following substitutions: N31D, S74A, Y89D, E209L, Y245V, D348K, D378A, K383A, P386A, I387F, I405V, N448S, and N480R.

The variants may be produced using conventional protein engineering techniques.

Expression of the Enzymes in Plants

A DNA sequence encoding an enzyme of interest, such as a hybrid enzyme or a variant of a wild type enzyme or a hybrid of the present invention, may be transformed and expressed in transgenic plants as described below.

The transgenic plant can be dicotyledonous or monocotyledonous, for short a dicot or a monocot. Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum and maize (corn).

Examples of dicot plants are tobacco, legumes, such as lupins, potato, sugar beet, pea, bean and soybean, and cruciferous plants (family Brassicaceae), such as cauliflower, oil seed rape and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. In the present context, also specific plant cell compartments, such as chloroplast, apoplast, mitochondria, vacuole, peroxisomes and cytoplasm are considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the invention are the progeny of such plants, plant parts and plant cells.

The transgenic plant or plant cell expressing the enzyme of interest may be constructed in accordance with methods known in the art. In short the plant or plant cell is constructed by incorporating one or more expression constructs encoding the enzyme of interest into the plant host genome and propagating the resulting modified plant or plant cell into a transgenic plant or plant cell.

Conveniently, the expression construct is a DNA construct which comprises a gene encoding the enzyme of interest in operable association with appropriate regulatory sequences required for expression of the gene in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, e.g., on the basis of when, where and how the enzyme is desired to be expressed. For instance, the expression of the gene encoding the enzyme of the invention may be constitutive or inducible, or may be developmental, stage or tissue specific, and the gene product may be targeted to a specific cell compartment, tissue or plant part such as seeds or leaves. Regulatory sequences are, e.g., described by Tague et al., 1988, *Plant Phys*. 86: 506.

For constitutive expression the 35S-CaMV, the maize ubiquitin 1 and the rice actin 1 promoter may be used (Franck et al., 1980, *Cell* 21: 285-294, Christensen, Sharrock and Quail, 1992, Maize polyubiquitin genes: structure, thermal perturbation of expression and transcript splicing, and promoter activity following transfer to protoplasts by electroporation. *Plant Mol. Biol*. 18: 675-689; Zhang, McElroy and Wu, 1991, Analysis of rice Act1 5' region activity in transgenic rice plants. *Plant Cell* 3: 1155-1165). Organ-specific promoters may, e.g., be a promoter from storage sink tissues such as seeds, potato tubers, and fruits (Edwards and Coruzzi, 1990, *Annu. Rev. Genet*. 24: 275-303), or from metabolic sink tissues such as meristems (Ito et al., 1994, *Plant Mol. Biol*. 24: 863-878), a seed specific promoter such as the glutelin, prolamin, globulin or albumin promoter from rice (Wu et al., 1998, *Plant and Cell Physiology* 39(8): 885-889), a *Vicia faba* promoter from the legumin B4 and the unknown seed protein gene from *Vicia faba* described by Conrad et al., 1998, *Journal of Plant Physiology* 152(6): 708-711, a promoter from a seed oil body protein (Chen et al., 1998, *Plant and Cell Physiology* 39(9): 935-941, the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102(3): 991-1000, the chlorella virus adenine methyltransferase gene promoter (Mitra and Higgins, 1994, *Plant Molecular Biology* 26(1): 85-93, or the aldP gene promoter from rice (Kagaya et al., 1995, *Molecular and General Genetics* 248(6): 668-674, or a wound inducible promoter such as the potato pin2 promoter (Xu et al., 1993, *Plant Molecular Biology* 22(4): 573-588. Likewise, the promoter may inducible by abiotic treatments such as temperature, drought or alterations in salinity or induced by exogenously applied substances that activate the promoter e.g., ethanol, oestrogens, plant hormones like ethylene, abscisic acid and gibberellic acid and heavy metals.

A promoter enhancer element may be used to achieve higher expression of the enzyme in the plant. For instance, the promoter enhancer element may be an intron which is placed between the promoter and the nucleotide sequence encoding the enzyme. For instance, Xu et al. op cit disclose the use of the first intron of the rice actin 1 gene to enhance expression.

The selectable marker gene and any other parts of the expression construct may be chosen from those available in the art.

The DNA construct is incorporated into the plant genome according to conventional techniques known in the art, including *Agrobacterium*-mediated transformation, virus-mediated transformation, micro injection, particle bombardment, biolistic transformation, and electroporation (Gasser et al., *Science* 244: 1293; Potrykus, 1990, *Bio/Techn.* 8: 535; and Shimamoto et al., 1989, *Nature* 338: 274).

Presently, *Agrobacterium tumefaciens* mediated gene transfer is the method of choice for generating transgenic dicots (for review Hooykas & Schilperoort, 1992, *Plant Mol. Biol.* 19: 15-38), and can also be used for transforming monocots, although other transformation methods often are used for these plants. Presently, the method of choice for generating transgenic monocots supplementing the *Agrobacterium* approach is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21(3): 415-428.

Following transformation, the transformants having incorporated the expression construct are selected and regenerated into whole plants according to methods well-known in the art. Often the transformation procedure is designed for the selective elimination of selection genes either during regeneration or in the following generations by using, e.g., co-transformation with two separate T-DNA constructs or site specific excision of the selection gene by a specific recombinase.

Starch Processing

The hybrid enzyme of the first aspect of the invention or the variant of the second aspect of the invention may in an eighth aspect be used in a process for liquefying starch, wherein a gelatinized or granular starch substrate is treated in aqueous medium with the hybrid enzyme. Preferably the process comprising hydrolysis of a slurry of gelatinized or granular starch, in particular hydrolysis of granular starch into a soluble starch hydrolysate at a temperature below the initial gelatinization temperature of said granular starch.

In a preferred embodiment the starch slurry in addition to being contacted with the hybrid enzyme of the first aspect or the variant of the second aspect of the invention is contacted with an enzyme selected from the list consisting of; a fungal alpha-amylase (EC 3.2.1.1), a beta-amylase (E.C. 3.2.1.2), and a glucoamylase (E.C.3.2.1.3). In an embodiment further a Termamyl-like alpha-amylase or a debranching enzyme, such as an isoamylase (E.C. 3.2.1.68) or a pullulanases (E.C. 3.2.1.41) is added. In the context of the present invention a Termamyl-like alpha-amylase is an alpha-amylase as defined in WO 99/19467 on page 3, line 18 to page 6, line 27.

The starch slurry to be subjected to the process of the seventh aspect of the invention may have 20-55% dry solids granular starch, preferably 25-40% dry solids granular starch, more preferably 30-35% dry solids granular starch.

After being subjected to the process of the seventh aspect of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids of the granular starch is converted into a soluble starch hydrolysate.

According to the invention the process of the seventh aspect is conducted at a temperature below the initial gelatinization temperature. Preferably the temperature at which the processes are conducted is at least 30° C., at least 31° C., at least 32° C., at least 33° C., at least 34° C., at least 35° C., at least 36° C., at least 37° C., at least 38° C., at least 39° C., at least 40° C., at least 41° C., at least 42° C., at least 43° C., at least 44° C., at least 45° C., at least 46° C., at least 47° C., at least 48° C., at least 49° C., at least 50° C., at least 51° C., at least 52° C., at least 53° C., at least 54° C., at least 55° C., at least 56° C., at least 57° C., at least 58° C., at least 59° C., or preferably at least 60° C.

The pH at which the process of the seventh aspect of the invention is conducted may in be in the range of 3.0 to 7.0, preferably from 3.5 to 6.0, or more preferably from 4.0-5.0.

The granular starch to be processed in the process of the invention may in particular be obtained from tubers, roots, stems, legumes, cereals or whole grain. More specifically the granular starch may be obtained from corns, cobs, wheat, barley, rye, milo, sago, cassava, tapioca, sorghum, rice, peas, bean, banana or potatoes. Specially contemplated are both waxy and non-waxy types of corn and barley. The granular starch to be processed may be a highly refined starch quality, preferably at least 90%, at least 95%, at least 97% or at least 99.5% pure or it may be a more crude starch containing material comprising milled whole grain including non-starch fractions such as germ residues and fibres. The raw material, such as whole grain, is milled in order to open up the structure and allowing for further processing. Two milling processes are preferred according to the invention: wet and dry milling. In dry milling the whole kernel is milled and used. Wet milling gives a good separation of germ and meal (starch granules and protein) and is with a few exceptions applied at locations where the starch hydrolysate is used in production of syrups. Both dry and wet milling is well known in the art of starch processing and are equally contemplated for the process of the invention. Also corn grits, and preferably milled corn grits may be applied.

In an embodiment of the process of the seventh aspect of the invention the hybrid enzyme is used in a process for production of fuel or potable ethanol comprising contacting the treated starch with a yeast. Preferably the process comprises fermentation with a yeast carried out simultaneously or separately/sequential to the hydrolysis of the granular starch slurry. When the fermentation is performed simultaneous to the hydrolysis the temperature is preferably between 30° C. and 35° C., and more preferably between 31° C. and 34° C.

In another embodiment the granular starch slurry is being contacted with a polypeptide comprising a CBM, but no catalytic module, i.e., application of loose CBMs. The loose CBMs may be starch binding modules, cellulose-binding modules, chitin-binding modules, xylan-binding modules, mannan-binding modules, and other binding modules. Preferred CBMs in the present context are microbial CBMs, particularly bacterial or fungal CBMs. Particularly preferred are the starch binding modules disclosed in Danish application no. PA 2003 01568 as the polypeptide sequences SEQ ID NO:1, SEQ ID NO:2, and SEQ ID NO:3 or the starch binding modules shown in the present disclosure as SEQ ID NO:12, SEQ ID NO:13, SEQ ID NO:14, SEQ ID NO:15; SEQ ID NO:16, SEQ ID NO:17, SEQ ID NO:18; SEQ ID NO:19, SEQ ID NO:20, SEQ ID NO:21, SEQ ID NO:22, SEQ ID NO:23. Most preferred CBMs include the CBMs disclosed in the present disclosure as SEQ ID NO:24 and as SEQ ID NO:25. Also preferred for the invention is the application of any CBM having at least 50%, 60%, 70%, 80% or even at least 90% homology to any of the afore mentioned CBM amino acid sequences. The loose CBMs may be applied to the granular starch slurry in effective amounts.

The glucose may also be fermented in to other fermentation products, such as citric acid, itaconic acid, lactic acid, gluconic acid; ketones; amino acids, such as glutamic acid (sodium monoglutaminate), but also more complex compounds such as antibiotics, such as penicillin, tetracyclin; enzymes; vitamins, such as riboflavin, B12, beta-carotene; hormones, which are difficult to produce synthetically.

Dough-Based Products

The hybrid enzyme may be used for the preparation of a dough-based edible product, particularly a hybrid enzyme comprising an amylolytic module derived from *Aspergillus oryzae* such as the amino acid sequence shown in SEQ ID NO: 30. The hybrid enzyme used for the preparation of a dough-based edible product is in particular a hybrid enzyme comprising the sequence shown as SEQ ID NO: 30 and/or as amino acids 21-498 of SEQ ID NO: 30 or any variant thereof such as a variant comprising one or more substitutions selected from the list consisting of: □81R, K158D, K158V, S161 D, S161 N, Q163S, Q163A, D164S, Y175W, E176D, D177N, N264K, N264E, M266L, G466D, D468S, and N470D. The hybrid enzyme used for the preparation of a dough-based edible product is in particular a hybrid enzyme comprising an amino acid sequence which has at least 50% homology, preferably at least 60%, 70%, 80%, 85% or at least 90%, e.g., at least 95%, 97%, 98%, or at least 99%, such as 100% homology to the sequences set forth in SEQ ID NO: 30.

The dough generally comprises flour (particularly wheat flour) and water. The dough is leavened, e.g., by adding chemical leavening agents or yeast, usually *Saccharomyces cerevisiae* (baker's yeast).

The dough-based product is made by leavening and heating the dough, e.g., by baking or steaming. Examples are steamed or baked bread (in particular white, whole-meal or rye bread), typically in the form of loaves or rolls, The dough may comprise one or more additional enzymes, e.g., a second amylase (e.g., a maltogenic alpha-amylase), a cyclodextrin glucanotransferase, a protease or peptidase, in particular an exopeptidase, a transglutaminase, a lipase, a phospholipase, a cellulase, a hemicellulase (e.g., a pentopsanase or xylanase), a glycosyltransferase, a branching enzyme or an oxidase such as glucose oxidase or an oxidase with higher activity on maltose than on glucose.

The hybrid enzyme may be used at a lower dosage than the catalytic module with alpha-amylase activity used alone (compared on a weight basis).

Materials and Methods
Purchased Material

Enzymes for DNA manipulations (e.g., restriction endonucleases, ligases etc.) are obtainable from New England Biolabs, Inc. and were used according to the manufacturer's instructions. Amplified plasmids were recovered with Qiagen® Plasmid Kit (Qiagen). Polymerase Chain Reaction (PCR) was carried out with Expand™ PCR system (Roche). QIAquick™ Gel Extraction Kit (Qiagen) was used for purification of PCR fragments and DNA fragments excised from agarose gels.

Strains and Plasmids

*Aspergillus kawachii* strain IF04308 was used as donor of CBM and linker sequences. *Aspergillus niger* strain DSM 2761 donated the amylolytic sequence (WO89/01969). *Aspergillus niger* strain MBin120 described in U.S. provisional patent application No. 60/459,902 (10345.000-US) was used as host strain. The *Aspergillus* expression plasmid pMT2188 described in the patent WO200295014 was used as vector. The pyrF defective *Escherichia coli* strain DB6507 (ATCC 35673) was used for propagation of pHUda381 and pHUda387

Plasmid pMT2188 consists of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglycosidase terminator (Tamg). Also present on the plasmid is the *Aspergillus* selective marker amdS from *Aspergillus nidulans* enabling growth on acetamide as sole nitrogen source and the URA3 marker from *Saccharomyces cerevisiae* enabling growth of the pyrF defective *Escherichia coli* strain DB6507 (ATCC 35673), which propagates pHUda381 and pHUda387. Transformation into *E. coli* DB6507 using the *S. cerevisiae* URA 3 gene as selective marker was done in the following way:

*E. coli* DB6507 was made competent by the method of Mandel and Higa (Mandel and Higa, 1970, *J. Mol. Biol.* 45: 154). Transformants were selected on solid M9 medium (Sambrook et al., 1989, Molecular Cloning, a Laboratory Manual, 2. edition, Cold Spring Harbor Laboratory Press) supplemented with 1 g/l casaminoacids, 500 micrograms/l thiamine and 10 mg/l kanamycin.

Media and Substrates

Cove was composed of 342.3 g/L Sucrose, 20 ml/L COVE salt solution, 10 mM Acetamide and 30 g/L noble agar. Cove-2 was composed of 30 g/L Sucrose, 20 ml/L COVE salt solution, 10 mM, Acetamide and 30 g/L noble agar. COVE salt solution was composed of 26 g/L KCl, 26 g/L $MgSO_4.7H_2O$, 76 g/L $KH_2PO_4$ and 50 ml/L Cove trace metals. COVE trace metals was composed of 0.04 g/L $Na_2B_4O_7.10H_2O$, 0.4 g/L $CuSO_4.5H_2O$, 1.2 g/L $FeSO_4.7H_2O$, 1.0 g/L $MnSO_4.H_2O$, 0.8 g/L $Na_2MoO_2.2H_2O$ and 10 g/L $ZnSO_4.7H_2O$. YPG was composed of 4 g/L yeast extract, 1 g/L $K_2HPO_4$, 0.5 g/L $MgSO_4.7H_2O$ and 15 g/L glucose, pH 6.0. STC was composed of 0.8 M Sorbitol, 25 mM Tris pH 8 and 25 mM $CaCl_2$. STPC was composed of 40% PEG4000 in STC buffer. Cove top agarose was composed of 342.3 g/L Sucrose, 20 ml/L COVE salt solution, 10 mM Acetamide and 10 g/L low melt agarose. MLC was composed of 40 g/L Glucose, 50 g/L Soybean powder, 4 g/L Citric acid, pH 5.0. G0-50 was composed of glucose 50 g/L, KH2PO4 2 g/L, MgSO4-7aq 2 g/L, K2SO4 3 g, citric acid 3 g/L, oxalic acid 50 g/L, AMG trace metal solution 0.5 m/L and urea 3 g/L, pH 5.0. AMG trace metal solution was composed of 6.8 g/L $ZnCl_2.7H_2O$, 2.5 g/L $CuSO_4.5H_2O$, 0.24 g/L $NiCl_2.6H_2O$, 13.9 g/L $FeSO_4.7H_2O$, 13.5 g/L $MnSO_4.H_2O$ and 3 g/L citric acid.

Acid Stable Alpha-Amylase Activity

When used according to the present invention the activity of any acid stable alpha-amylase may be measured in AFAU (Acid Fungal Alpha-amylase Units), which are determined relative to an enzyme standard. 1 FAU is defined as the amount of enzyme which degrades 5.260 mg starch dry matter per hour under the below mentioned standard conditions.

Acid stable alpha-amylase, an endo-alpha-amylase (1,4-alpha-D-glucan-glucano-hydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

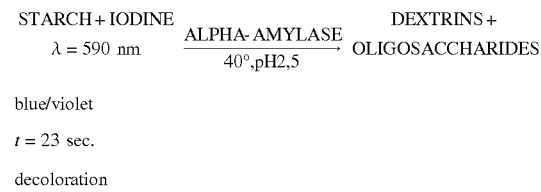

STARCH + IODINE $\xrightarrow[40°,pH2,5]{\text{ALPHA-AMYLASE}}$ DEXTRINS + OLIGOSACCHARIDES
$\lambda = 590$ nm blue/violet $t = 23$ sec.

decoloration

Standard Conditions/Reaction Conditions:

| Substrate: | Soluble starch, approx. 0.17 g/L |
|---|---|
| Buffer: | Citrate, approx. 0.03 M |
| Iodine (I2): | 0.03 g/L |
| $CaCl_2$: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

A folder EB-SM-0259.02/01 describing this analytical method in more detail is available upon request to Novozymes A/S, Denmark, which folder is hereby included by reference.

Glucoamylase Activity

Glucoamylase activity may be measured in AmyloGlucosidase Units (AGU). The AGU is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

Amg Incubation:

| Substrate: | maltose 23.2 mM |
|---|---|
| Buffer: | acetate 0.1 M |
| pH: | 4.30 ± 0.05 |
| Incubation temperature: | 37° C. ± 1 |
| Reaction time: | 5 minutes |
| Enzyme working range: | 0.5-4.0 AGU/mL |

Color Reaction:

| GlucDH: | 430 U/L |
|---|---|
| Mutarotase: | 9 U/L |
| NAD: | 0.21 mM |
| Buffer: | phosphate 0.12 M; 0.15 M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

DNA Manipulations

Unless otherwise stated, DNA manipulations and transformations were performed using standard methods of molecular biology as described in Sambrook et al., 1989, Molecular cloning: A laboratory manual, Cold Spring Harbor lab. Cold Spring Harbor, N.Y.; Ausubel, F. M. et al. (eds.) "Current Protocols in Molecular Biology", John Wiley and Sons, 1995; Harwood, C. R. and Cutting, S. M. (eds.)

EXAMPLE 1

Cloning of Carbohydrate Binding Module (CBM) from *Aspergillus Kawachii*

In order to clone the carbohydrate binding module (CBM) with linker from *A. kawachii*, the primers CBM1 (SEQ ID NO:1) and CBM2 (SEQ ID NO:2) were designed based on the nucleotide sequences of *Aspergillus kawachii* acid stable alpha-amylase in the EMBL database (EMBL:#AB008370). CBM1 and CBM2 comprise a BamHI site and a SalI site, respectively.

```
CBM1:
5'-gaagggatccgattttactagtacatccaaagccaccac-3'

CBM2:
5'-tttgtcgacctacctccacgtatcaaccaccgtctcc-3'
```

PCR reaction was carried out with the primers CBM1 and CBM2 using genomic DNA from *A. kawachii* (IF04308) as template. Reaction components (1 ng/microL of genomic DNA, 250 mM dNTP each, primer 250 nM each, 0.1 U/microL in Taq polymerase in 1× buffer (Roche Diagnostics, Japan)) were mixed and submitted for PCR under the following conditions.

| Step | Temperature | Time |
|---|---|---|
| 1 | 94° C. | 2 min |
| 2 | 92° C. | 1 min |
| 3 | 55° C. | 1 min |
| 4 | 72° C. | 1 min |
| 5 | 72° C. | 10 min |
| 6 | 4° C. | forever |

Steps 2 to 4 were repeated 30 times.

A 0.4 kb fragment comprising the CBM with linker region was amplified. The amplified DNA was cut by Sal I and BamH I and ligated into pMT2188 digested by Xho I and BamH I to create pHUda381 having CBM with linker region from *Aspergillus kawachii*, *Aspergillus niger* neutral amylase promoter, *Aspergillus nidulans* TPI leader sequences, *Aspergillus niger* glucoamylase terminator and *Aspergillus nidulans* amdS gene as a marker. The pHUda381 was sequenced to confirm presence of correct CBM with linker sequence. The CBM with linker sequence is shown in SEQ ID NO:5.

EXAMPLE 2

Expression of the Hybrid Enzyme in *Aspergillus niger*

The production of the cDNA sequence of *Aspergillus niger* acid stable alpha-amylase gene and the cDNA clone of *Aspergillus niger* acid stable alpha-amylase are described in WO 89/01969 (example 1 and 3). A PCR reaction with cDNA clone of *Aspergillus niger* acid stable alpha-amylase as template was performed using the primers (SEQ ID NO:3) and (SEQ ID NO:4) to introduce a BamHI site and a SpeI site, respectively.

```
                                        (SEQ ID NO: 3)
5'-tttggatccaccatgagattatcgacttcgagtctcttc-3'

(SEQ ID NO: 4)
5'-tttactagtagcagcagcagttgtggtcgtggttgttc-3'
```

Reaction components (1 ng/microL of template DNA, 250 mM dNTP each, primer 250 nM each, 0.1 U/microL in Taq polymerase in 1× buffer (Roche Diagnostics, Japan)) were mixed and submitted for PCR under the following conditions.

| Step | Temperature | Time |
|---|---|---|
| 1 | 94° C. | 2 min |
| 2 | 92° C. | 1 min |
| 3 | 55° C. | 1 min |
| 4 | 72° C. | 2 min |
| 5 | 72° C. | 10 min |
| 6 | 4° C. | forever |

Steps 2 to 4 were repeated 30 times.

The 1.5 kb amplified DNA fragment was cut by Spe I and BamH I and ligated into pHUda381 digested by Spe I and BamH I to create the expression plasmid pHUda387 comprising *Aspergillus niger* acid stable alpha-amylase cDNA fused with CBM from *Aspergillus* kawachii. The pHUda387 was sequenced to confirm that no changes had happen in the *Aspergillus niger* acid stable alpha-amylase cDNA sequences. The *Aspergillus niger* acid stable alpha-amylase cDNA sequence is shown in SEQ ID NO:7.

The pHUda387 was transformed into *Aspergillus niger* MBin120. The host strain was propagated in 100 ml of non-selective YPG medium at 32° C. for 16 hrs on a rotary shaker at 120 rpm. Cells were collected by filtering, washed with 0.6 M KCl and resuspended in 20 ml of 0.6 M KCl containing a commercial beta-glucanase product (GLUCANEX™, Novozymes A/S) at final concentration of 600 microL/ml. The suspension was incubated at 32° C. at 80 rpm until protoplasts were formed, then washed twice with STC buffer. The protoplasts were counted with a hematometer and resuspended and adjusted in an 8:2:0.1 solution of STC:STPC:DMSO to a final concentration of $2.5 \times 10^7$ protoplasts/ml. About 3 micrograms of plasmid DNA was added to 100 microL of protoplast suspension, mixed gently and incubated on ice for 20 min. One ml of SPTC was added and the protoplast suspension was incubated for 30 min at 37° C. After the addition of 10 ml of 50° C. Cove top agarose, the reaction was poured onto Cove agar plates and the plates were incubated at 32° C. After 5 days transformants were selected from the Cove medium.

The selected transformants were inoculated in 100 ml of MLC media and cultivated at 30° C. for 2 days. 10 ml of MLC medium was inoculated to 100 ml of G0-50 medium and cultivated at 30° C. for 5 days. The supernatant was obtained by centrifugation.

The acid stable alpha-amylase activity in the supernatant was determined as decrease of blue color of starch-iodine complex measured in OD 590 nm. 25 microL of enzyme samples dissolved in sample buffer (51.4 mM calcium chloride in 2 mM citrate buffer [pH 2.5]) was mixed with 135 microL of substrate solution (0.6 g/L of starch [Merck 1253] and 12 g/L of sodium acetate in 100 mM citrate buffer [pH 2.5]) and incubated at 37° C. for 325 sec. After 325 sec, 90 microL of iodine solution (1.2 g/L of potassium iodine [Merck 5043] and 0.12 g/L of iodine [Merck 4761]) was added to the reaction mixture and incubated at 37° C. for 25 sec. Activity was measured at 590 nm on a spectrophotometer. 25 microL of distilled water was used instead of enzyme samples in blank experiments.

EXAMPLE 3

Performance of the Hybrid Enzyme in SSF of Non-Gelatinized Starch

The relative performance of *Aspergillus niger* acid stable alpha-amylase and *Aspergillus niger* acid stable alpha-amylase with an attached carbohydrate-binding module was evaluated via mini-scale SSF (Simultaneous Saccharification and Fermentation) fermentations. Dosages used were 0.3, 0.5 and 1.0 AFAU/g DS of the respective alpha-amylase complemented with a 0.5 AGU/g DS dose of purified *Aspergillus niger* glucoamylase. Briefly, approximately 1.9 g of ground corn (yellow #2 dent corn ground in a pilot scale hammer mill and passed through a 2 mm screen, 11.2% moisture content) was added to 16 ml polystyrene tubes (Falcon 352025). A solution of 0.02 N $H_2SO_4$ with 3 mg/ml penicillin was added in an amount appropriate to bring the dry solids level (DS) to 34% and the pH to 5.0. Treatments were made in six replicates.

After dosing the enzymes, the tubes were inoculated with $4.74 \times 10^8$ yeast cells/ml. Tubes were capped with a screw on lid which had been punctured with a very small needle to allow gas release and vortexed briefly before weighing and incubation at 32° C. Fermentation progress was followed by weighing the tubes over time. Tubes were vortexed briefly before weighing. The relationship used between amount of $CO_2$ loss and the weight of ethanol was: $CO_2$ loss (g)× 1.045=EtOH (g). The results are shown in table 2.

TABLE 2

Average ethanol yield as g ethanol/g DS after 50 hrs.

| Dose (AFAU/g DS) | *Aspergillus niger* alpha-amylase | *Aspergillus niger* alpha-amylase + CBM |
|---|---|---|
| 0.3 | 0.342 | 0.366 |
| 0.5 | 0.348 | 0.383 |
| 1.0 | 0.365 | 0.390 |

95% confidence limits: +/−0.008

On an equal activity basis, *Aspergillus niger* acid stable alpha-amylase with an attached carbohydrate-binding module (hybrid) significantly outperformed *Aspergillus niger* acid stable alpha-amylase (native) at all dosages tested. The hybrid enzyme was approximately three times more effective than the native enzyme (i.e., performance of *Aspergillus niger* acid stable alpha-amylase could be matched with about three times less *Aspergillus niger* acid stable alpha-amylase with an attached carbohydrate-binding module).

EXAMPLE 4

Performance of Hybrid Enzymes with Different Combinations of CBM, Linker Sequence and Catalytic Module Hybrid enzyme variants comprising the *Aspergillus niger* acid stable alpha-amylase (AA) and a CBM from *A. kawachii* alpha-amylase, *A. niger* AMG, *T. emersonii* AMG, *Athelia rolfsii* AMG, or *Bacillus* sp. maltogenic alpha-amylase (Novamyl) were constructed. The linker sequence from *A. kawachii* alpha-amylase (SEQ ID NO:27) was used in all the variants.

The performance of the variants was assessed using corn starch (SIGMA S-9679) as substrate, *Aspergillus niger* glucoamylase G2 0.5 AGU/g DS, variant 1.0 AFAU/g DS and quantification of the liberated glucose with the Glucose B-test kit (Wako Pure Chemicals 271-3141). The results are shown in table 3.

TABLE 3

Performance of hybrid enzymes with different CBMs.
Glucose mg/ml after 20, 48, and 68 hrs (1.0 AFAU/gDS)

| Variant | Catalytic module | Linker | SBD | 20 hrs | 48 hrs | 68 hrs |
|---|---|---|---|---|---|---|
| JA001 | *Aspergillus niger* | kawachii AA | kawachii AA | 0.18 | 0.51 | 1.07 |
| JA002 | *Aspergillus niger* | kawachii AA | *niger* AMG | 0.38 | 1.08 | 1.88 |
| JA003 | *Aspergillus niger* | kawachii AA | *emersonii* AMG | 0.04 | 0.19 | 0.43 |
| JA004 | *Aspergillus niger* | kawachii AA | *rolfsii* AMG | 0.48 | 1.43 | 2.48 |
| JA005 | *Aspergillus niger* | kawachii AA | *Bacillus* MA | −0.03 | −0.04 | 0.10 |

Hybrid enzyme variants comprising the *Aspergillus niger* acid stable alpha-amylase and a CBM from *A. kawachii* alpha-amylase, *A. niger* AMG, or *Athelia rolfsii* AMG, were constructed. Also variants with different linker sequence were constructed. The linker sequences used were *A. niger* AMG linker (SEQ ID NO:26), *A. kawachii* alpha-amylase linker (SEQ ID NO:27), *Athelia rolfsii* AMG linker (SEQ ID NO:28), and the PEPT linker (SEQ ID NO:29). A variant having two CBDs in tandem was also constructed (JA012).

The performance of the variants was assessed as above, only with *Aspergillus niger* glucoamylase G1 and the variant was dosed as 0.3 AFAU/g DS. The results are shown in table 4.

TABLE 4

Performance of hybrid enzymes with different linker sequences and catalytic modules. Glucose mg/ml after 18, 24, and 42 hrs.

| Variant | Catalytic module | Linker | SBD | 18 hrs | 24 hrs | 42 hrs | 68 hrs |
|---|---|---|---|---|---|---|---|
| JA001 | *Aspergillus niger* | kawachii AA | kawachii AA | 2.73 | 4.40 | 7.01 | 8.93 |
| JA002 | *Aspergillus niger* | kawachii AA | niger AMG | 2.75 | 4.30 | 7.03 | 9.23 |
| JA004 | *Aspergillus niger* | kawachii AA | rolfsii AMG | 2.91 | 4.35 | 7.16 | 9.11 |
| JA008 | *Aspergillus niger* | niger AMG | niger AMG | 3.01 | 4.26 | 7.31 | 8.76 |
| JA009 | *Aspergillus niger* | rolfsii AMG | niger AMG | 3.02 | 4.69 | 7.60 | 9.11 |
| JA010 | *Aspergillus niger* | PEPT | niger AMG | 3.18 | 4.66 | 7.82 | 9.38 |
| JA011 | *Aspergillus niger* | rolfsii AMG | rolfsii AMG | 3.31 | 4.62 | 7.49 | 9.60 |
| JA012 | *Aspergillus niger* | kawachii AA | niger AMG + rolfsii AMG | 2.99 | 4.10 | 6.97 | 8.85 |

Hybrid enzyme variants comprising the linker and CBM from *A. kawachii* alpha-amylase with different catalytic modules were constructed. The catalytic modules applied were from *Aspergillus niger* acid stable alpha-amylase, *A. kawachii* alpha-amylase or *Aspergillus oryzae* alpha-amylase (Fungamyl™). The performance of the variants was assessed as above, with *Aspergillus niger* glucoamylase G1 and the variant dosed as 0.3 AFAU/g DS. The results are shown in table 5.

TABLE 5

Performance of hybrid enzymes with different catalytic modules. Glucose mg/ml after 18, 24, 42 and 68 hrs.

| Variant | catalytic module | Linker | SBD | 18 hrs | 24 hrs | 42 hrs | 68 hrs |
|---|---|---|---|---|---|---|---|
| JA001 | *A. niger* AA | kawachii AA | kawachii AA | 2.73 | 4.40 | 7.01 | 8.93 |
| JA006 | *A. oryzae* AA | kawachii AA | kawachii AA | 3.39 | 5.10 | 7.99 | 9.77 |
| JA007 | *A. kawachii* AA | kawachii AA | kawachii AA | 2.91 | 3.99 | 6.82 | 8.57 |

Hybrid enzyme variants comprising the linker and CBM from *A. kawachii* alpha-amylase or *A. rolfsii* AMG with different catalytic modules from *Aspergillus niger* acid stable alpha-amylase or *Aspergillus oryzae* alpha-amylase (Fungamyl™). The performance of the variants was assessed as above with *Aspergillus niger* glucoamylase G1 and the variant dosed as 0.3 AFAU/g DS. The results are shown in table 6.

TABLE 6

Performance of different hybrid enzymes. Glucose mg/ml after 18, 24 or 42 hrs.

| Variant | catalytic module | Linker | SBD | 18 hrs | 24 hrs | 42 hrs |
|---|---|---|---|---|---|---|
| JA001 | *A. niger* AA | kawachii AA | kawachii AA | 4.64 | 5.61 | 8.38 |
| JA006 | *A. oryzae* AA | kawachii AA | kawachii AA | 6.27 | 7.93 | 9.40 |
| JA017 | *A. oryzae* AA | rolfsii AMG | rolfsii AMG | 6.68 | 8.87 | 9.80 |

EXAMPLE 5

Variants of JA017 with One or More Substitutions in the Catalytic Module

Variants of the hybrid enzyme JA017 (amino acid sequence shown in SEQ ID NO:40) comprising the *A. rolfsii* AMG CBM, *A. rolfsii* linker sequence and the *A. oryzae* alpha amylase catalytic module with one or more substitutions in the catalytic module were constructed using conventional protein engineering techniques. Table 7 lists the substitutions in the variants.

TABLE 7

Variants of JA017 (SEQ ID NO: 40) with one or more substitutions in the catalytic module.

| No. | Substitution |
|---|---|
| JA019 | Y175W E176D |
| JA050 | N264K M266L |
| JA056 | D253N |
| JA057 | K158D S161D Q163S D164S G466D D468S N470D |
| JA059 | G60N N264K M266L |
| JA060 | D177N |
| JA061 | K158D S161D Q163S D164S Y175W E176D G466D D468S N470D |
| JA062 | K158D S161D Q163S D164S Y175W E176D N264K M266L G466D D468S N470D |
| JA063 | K158V S161D Q163S D164S G466D D468S N470D |
| JA069 | K158D S161N Q163A D164S G466D D468S N470D |
| JA074 | K158V S161N Q163A D164S N264K M266L G466D D468S N470D |
| JA076 | Q81R K158V S161N Q163A D164S Y175W E176D G466D D468S N470D |
| JA083 | K158D S161D Q163S D164S Y175W E176D N264E M266L G466D D468S N470D |
| JA085 | Q81R K158V S161N Q163A D164S Y175W E176D D177N N264K M266L G466D |
| JA093 | Q81R K158V S161N Q163A D164S Y175W E176D D177N N264E M266L G466D |
| JA094 | K158V S161N Q163A D164S Y175W E176D D177N N264K M266L G466D D468S |
| JA095 | K158V S161N Q163A D164S Y175W E176D D177N N264E M266L G466D D468S |
| JA096 | K158V S161N Q163A D164S D177N N264K M266L G466D D468S N470D |
| JA097 | K158V S161N Q163A D164S D177N N264E M266L G466D D468S N470D |

The variants were expressed in *Aspergillus oryzae* and characterized for pH stability, thermostability and the performance toward raw starch by glucose releasing test.

JA085 showed at least by 5° C. higher thermostability than JA017 at pH 4.5 was and stable even at pH 3.0.

The new variants JA085 and JA074 showed a high specific activity in the glucose release test. JA085 continued to release glucose even at pH 3.8 where JA017 was quickly inactivated. JA074 had the highest glucose yields at pH 4.0 was but was inactivated at pH 3.8.

Tables 8-10 list the temperature stability as residual activity after 30 min incubation at 55° C. and 60° C. at pH 4.5, the specific activity, the pH stability and the activity in the glucose releasing test of a number of variants.

TABLE 8

Temperature stability and specific activity of selected PE variants

| | Temperature stability (%) | | | Specific activity |
|---|---|---|---|---|
| | in 1 mM CaCl$_2$ | | No CaCl$_2$ | |
| | 55° C. | 60° C. | 55° C. | (mFAU/OD280) |
| JA017 | 2 | 0 | 0 | 3157 |
| JA057 | 12 | 0 | 0 | |
| JA061 | 51 | 0 | 16 | |
| JA063 | 18 | 0 | 0 | |
| JA069 | 16 | 0 | 0 | |
| JA074 | 19 | 0 | 0 | |
| JA085 | 68 | 20 | 12 | 3653 |
| JA095 | 59 | 7 | 2 | 4240 |
| JA096 | 53 | 0 | 0 | |
| JA097 | 40 | 0 | 0 | |

Table 9a. Temperature stability (pH4.5, 1 hour incubation)

| Temp. ° | JA017A | JA085A |
|---|---|---|
| 35 | 101 | 107 |
| 40 | 109 | 102 |
| 45 | 98 | 96 |
| 50 | 64 | 95 |
| 55 | 0 | 56 |
| 60 | 0 | 27 |
| 65 | 0 | 0 |

Table 9b. pH stability (32° C., 1 hour incubation)

| pH | JA017A | JA085A |
|---|---|---|
| 2.5 | 0 | 20 |
| 3.0 | 23 | 76 |
| 3.5 | 74 | 83 |
| 4.0 | 88 | 92 |
| 4.5 | 86 | 95 |
| 5.0 | 96 | 99 |
| 5.5 | 100 | 100 |

Table 10a. Performance in glucose releasing test with purified *A. niger* AMG G2 at pH 4.0. Glucose mg/ml.

| | 0 min | 19 min | 43 min | 67 min | 91 min |
|---|---|---|---|---|---|
| JA001 | 0.48 | 3.48 | 5.67 | 8.26 | 10.79 |
| JA017 | 0.46 | 6.45 | 7.97 | 8.71 | 8.98 |
| JA074 | 0.44 | 8.85 | 14.69 | 18.24 | 20.29 |
| JA085 | 0.41 | 5.87 | 10.62 | 13.92 | 17.34 |

Table 10b. Performance in glucose releasing test with purified *A. niger* AMG G2 at pH 3.8. Glucose mg/ml.

| | 0 min | 19 min | 43 min | 67 min | 91 min |
|---|---|---|---|---|---|
| JA001 | 0.48 | 3.19 | 5.28 | 7.63 | 10.32 |
| JA017 | 0.46 | 4.28 | 4.71 | 4.98 | 5.13 |
| JA074 | 0.43 | 7.75 | 11.58 | 13.55 | 13.93 |
| JA085 | 0.41 | 5.71 | 9.73 | 12.99 | 15.76 |

Table 11a. Performance in glucose releasing test with purified *A. niger* AMG G2 at pH 3.9. Glucose mg/ml.

|       | 0 min | 18 min | 90 min |
|-------|-------|--------|--------|
| JA074 | 0.41  | 6.83   | 16.87  |
| JA085 | 0.40  | 4.50   | 14.08  |
| JA094 | 0.40  | 4.48   | 14.00  |
| JA095 | 0.40  | 4.49   | 13.82  |

Table 11b. Performance in glucose releasing test with purified *A. niger* AMG G2 at pH 3.6. Glucose mg/ml.

|       | 0 min | 18 min | 90 min |
|-------|-------|--------|--------|
| JA074 | 0.43  | 5.01   | 7.57   |
| JA085 | 0.43  | 4.18   | 10.61  |
| JA094 | 0.42  | 4.18   | 11.18  |
| JA095 | 0.42  | 4.33   | 11.52  |

EXAMPLE 6

Variants of the *Aspergillus kawachii* Acid Alpha-Amylase

A variant of the *Aspergillus kawachii* acid alpha-amylase suitable for raw starch hydrolysis may be produced by conventional protein engineered of the sequence comprising the catalytic module. Specific position wherein alterations can improve specific activity and/or stability was predicted based on similarity to one of the following fungal alpha-amylases having the indicated amino acid sequence and a three-dimensional structure found under the indicated identifier in the RCSB Protein Data Bank (www.rcsb.org): the *A. niger* acid alpha-amylase (2aaa, SEQ ID NO:42) and the alpha-amylase (TAKA amylase) from *Aspergillus oryzae* (6taa or 7taa, SEQ ID NO:43). The two 3D models were superimposed by aligning the amino acid residues of each catalytic triad. This was done by methods known in the art based on the deviations of the three pairs of C-alpha atoms, e.g., by minimizing the sum of squares of the three deviations or by aligning so as to keep each deviation below 0.8 Å, e.g., below 0.6 Å, below 0.4 Å, below 0.3 Å or below 0.2 Å.

Alternatively, the superimposition may be done by aligning the two amino acid sequences by a conventional method and minimizing the sum of squares of the deviations of all corresponding pairs of amino acid residues. The sequence alignment may be done by conventional methods, e.g., by use the software GAP from UWGCG Version 8.

On the alignment of the three alpha-amylases from *A. kawachii*, *A. niger* (aaa_new) and *A. oryzae* (7taa) shown below are indicated the residues which are within 10 Å from the acarbose substrate in 7taa.pdb structure. These residues are targets for alterations conferring improved specific activity.

```
kawachi  MRVSTSSIAL AVSLFGKLAL GLSAAEWRTQ SIYFLLTDRF GRTDNSTTAT  50
aaa_new  MRLSTSSLFL SVSLLGKLAL GLSAAEWRTQ SIYFLLTDRF GRTDNSTTAT
7taa     .......... ..........  .ATPADWRSQ SIYFLLTDRF ARTDGSTTAT  29
                                          *  *   * kawachi  CNTGDQIYCG GSWQGIINHL DYIQGMGFTA IWISPITEQL PQDTSDGEAY 100
aaa_new  CDTGDQIYCG GSWQGIINHL DYIQGMGFTA IWISPITEQL PQDTADGEAY
7taa     CNTADQKYCG GTWQGIIDKL DYIQGMGFTA IWITPVTAQL PQTTAYGDAY  79
              *****                        *             ******* kawachi  HGYWQQKIYY VNSNFGTADD LKSLSDALHA RGMYLMVDVV PNHMGYAGNG 150
aaa_new  HGYWQQKIYD VNSNFGTADD LKSLSDALHA RGMYLMVDVV PNHMGYAGNG
7taa     HGYWQQDIYS LNENYGTADD LKALSSALHE RGMYLMVDVV ANHMGYDGAG 129
              ***                             * ****** kawachi  NDVDYSVFDP FDSSSYFHPY CLITDWDNLT MVQDCWEGDT IVSLPDLNTT 200
aaa_new  NDVDYSVFDP FDSSSYFHPY CLITDWDNLT MVQDCWEGDT IVSLPDLNTT
7taa     SSVDYSVFKP FSSQDYFHPF CFIQNYEDQT QVEDCWLGDN TVSLPDLDTT 179
              *****       *** **** kawachi  ETAVRTIWYD WVADLVSNYS VDGLRIDSVE EVEPDFFPGY QEAAGVYCVG 250
aaa_new  ETAVRTIWYD WVADLVSNYS VDGLRIDSVL EVEPDFFPGY QEAAGVYCVG
7taa     KDVVKNEWYD WVGSLVSNYS IDGLRIDTVK HVQKDFWPGY NKAAGVYCIG 229
                                ****     *                * kawachi  EVDNGNPALD CPYQKYLDGV LNYPIYWQLL YAFESSSGSI SNLYNMIKSV 300
aaa_new  EVDNGNPALD CPYQKVLDGV LNYPIYWQLL YAFESSSGSI SNLYNMIKSV
7taa     EVLDGDPAYT CPYQNVMDGV LNYPIYYPLL NAFKSTSGSM DDLYNMINTV 279
         **********    *          *  * * *              * kawachi  ASDCSDPTLL GNFIENHDNP RFASYTSDYS QAKNVLSYIF LSDGIPIVYA 350
aaa_new  ASDCSDPTLL GNFIENHDNP RFASYTSDYS QAKNVLSYIF LSDGIPIVYA
7taa     KSDCPDSTLL GTFVENHDNP RFASYTNDIA LAKNVAAFII LNDGIPIIYA 329
             *  *****    *                            * kawachi  GEEQHYSGGD VPYNREATWL SGYDTSAELY TWIATTNAIR KLAISADSDY 400
aaa_new  GEEQHYSGGK VPYNREATWL SGYDTSAELY TWIATTNAIR KLAISADSAY
7taa     GQEQHYAGGN DPANREATWL SGYPTDSELY KLIASANAIR NYAISKDTGF 379
          *  ***** kawachi  ITYKNDPIYT DSNTIAMRKG TSGSQIITVL SNKGSSGSSY TLTLSGSGYT 450
aaa_new  ITYANDAFYT DSNTIAMRKG TSGSQVITVL SNKGSSGSSY TLTLSGSGYT
7taa     VTYKNWPIYK DDTTIAMRKG TDGSQIVTIL SNKGASGDSY TLSLSGAGYT 429 kawachi  SGTKLIEAYT CTSVTVDSNG DIPVPMASGL PRVLLPASVV DSSSLCGGSG 500
aaa_new  SGTKLIEAYT CTSVTVDSSG DIPVPMASGL PRVLLPASVV DSSSLCGGSG
7taa     AGQQLTEVIG CTTVTVGSDG NVPVPMAGGL PRVLYPTEKL AGSKICS... 474
```

```
                                                     -continued
kawachi  NTTTTTTAAT  STSKATTSSS  SSSAAATTSS  SCTATSTTLP  ITFEELVTTT  550
aaa_new  RLYVE.....  ..........  ..........  ..........  ..........  505
7taa     ..........  ..........  ..........  ..........  ..........

kawachi  YGEEVYLSGS  ISQLGEWHTS  DAVKLSADDY  TSSNPEWSVT  VSLPVGTTFE  600
aaa_new  ..........  ..........  ..........  ..........  ..........
7taa     ..........  ..........  ..........  ..........  ..........

601                                           640
kawachi  YKFIKVDEGG  SVTWESDPNR  EYTVPECGSG  SGETVVDTWR              640
aaa_new  ..........  ..........  ..........  ..........
7taa     ..........  ..........  ..........  ..........
```

The specific alterations for increased specific activity is one substitution or a combination of substitutions in the following positions within the "10 Å distance of the substrate": 13, 15, 18, 32-36 (i.e., 32, 33, 34, 35, 36), 61, 63-64, 68-69, 73-84 (e.g., 73, 74, 75, 76, 77, 78, 79, 80, 81, 82, 83, 84), 117-125 (e.g., 117, 118, 119, 120, 121, 122, 123, 124, 125), 152-158 (e.g., 152, 153, 154, 155, 156, 157, 158), 161-162, 165-175 (e.g., 165, 166, 167, 168, 169, 170, 171, 172, 173, 174, 175), 204-211 (e.g., 204, 205, 206, 207, 208, 209, 210, 211), 216, 229-239 (229, 230, 231, 232, 233, 234, 235, 236, 237, 238, 239), 242, 250, 252-253, 255-257 (e.g., 255, 256, 257), 259-260, 275, 292, 295-299 (e.g., 295, 296, 297, 298, 299), 304, 328, 339-344 according to the 7taa numbering in the alignment above where the N-terminal is ATPAD in 7taa (TAKA amylase). Most interesting positions are: 33, 36, 74, 75, 77, 120, 153, 154, 155, 156, 157, 158, 162, 166, 169, 170, 199, 232, 233, 235, 238, 239, 256, 257, 331, 336, 339, 340, and 342. The substitutions may be to any amino acid residue.

Variants comprising one of the following substitutions or combinations thereof may be produced: G33A, I36K, S74A, D75Y, E77D, P120A, I153D, D154N, W155Y, D156E, N157D, L158Q, Q162E, E166L, T169N, I170T, E199K, E199L, D232L, N233D, N235D, L238Y, D239T, W256Y, Q257P, E331Q, S336A, D339K, D339N, V340D, and Y342A. The most interesting variants comprise one or more of the following substitutions; S74A, E166L, E199L, D339K, and D156E. Yet more interesting is the variant having the multiple substitutions S74A/E166L/E199L.

Based on similarity between *Aspergillus kawachii* and the *A. niger* acid alpha-amylases the following substitutions is predicted to improve the specific activity; N31D, S74A, Y89D, E209L, Y245V, D348K, D378A, K383A, P386A, I387F, I405V, N448S, and N480R, and a variant named WA01 comprising these substitutions can be produced.

EXAMPLE 7

Performance of a Variant of the *Aspergillus kawachii* Acid Alpha-Amylase

The sequences of the hybrids JA007 and JA001 described in example 4 are identical to respectively the sequence of the *A. kawachii* acid alpha-amylase (SEQ ID NO:41) and the sequence of the variant WA01 described in the previous example. As the two hybrids JA001 and JA007 have been compared in several tests the improvement in specific activity conferred by the substitutions to the variant WA01 can be very accurately predicted. Specific activity of the variant WA01 will be 1.7 to 1.8 times higher than the specific activity of the *A. kawachii* wild type amylase. The prediction is based on the data shown in table 12.

TABLE 12

Performance of the hybrid JA007 (identical to *A. kawachii* acid alpha-amylase) and the hybrid JA001 (identical to WA01, a variant of the *A. kawachii* acid alpha-amylase comprising the substitutions N31D, S74A, Y89D, E209L, Y245V, D348K, D378A, K383A, P386A, I387F, I405V, N448S, and N480R)

|  | AFAU/ml | mg/ml | AFAU/mg | A280 | AFAU/A280 |
|---|---|---|---|---|---|
| JA001 | 1.41 | 0.67 | 2.11 | 1.22 | 1.15 |
| JA007 | 0.56 | 0.46 | 1.22 | 0.89 | 0.63 |

EXAMPLE 8

Raw Starch Hydrolysis with an Acid Fungal Alpha-Amylase with or without CBD

This example illustrates the conversion of granular wheat starch or corn grits into glucose using acid fungal amylase without a CBM (SEQ ID NO:8) or the corresponding hybrid with a CBM (JA001). A slurry with 33% dry solids (DS) granular starch was prepared by adding 247.5 g of wheat starch or maize grits under stirring to 502.5 ml of water. The pH was adjusted with HCl to 4.5. The granular starch slurry was distributed to 100 ml blue cap flasks with 75 g in each flask. The flasks were incubated with magnetic stirring in a 60° C. water bath. At zero hours the enzyme activities were dosed to the flasks; glucoamylase (200 AGU/kg DS), an acid fungal amylase (50 AFAU/kg DS) and the wild type *Aspergillus niger* acid alpha-amylase (SEQ ID NO:8) or the *Aspergillus niger* acid alpha-amylase but fused to a linker and CBM derived from *A. kawachii* (SEQ ID NO:8 fused to SEQ ID NO:6). The *Aspergillus niger* acid alpha-amylase w/wo CBM was dosed as 100 KNU/kg DS. Samples were withdrawn after 24, 48, 72, and 96 hours.

Total dry solids starch was determined using the following method. The starch was completely hydrolyzed by adding an excess amount of alpha-amylase (300 KNU/kg dry solids) and placing the sample in an oil bath at 95° C. for 45 minutes. Subsequently the samples were cooled to 60° C. and an excess amount of glucoamylase (600 AGU/kg DS) was added followed by incubation for 2 hours at 60° C.

Soluble dry solids in the starch hydrolysate were determined by refractive index measurement on samples after filtering through a 0.22 microM filter. The sugar profiles were determined by HPLC. The amount of glucose was calculated as DX.

The results are shown in tables 13-14 (wheat starch) and 15-16 (corn grits).

TABLE 13

Soluble dry solids as percentage of total dry substance from wheat starch. Enzymes: glucoamylase, acid fungal alpha-amylase and more acid fungal alpha-amylase with the CBM or without the CBM.

|  | 24 hours | 46 hours | 70 hours | 90 hours |
|---|---|---|---|---|
| Without CBM | 81.1 | 88.6 | 89.4 | 90.7 |
| With CBM | 86.2 | 92.6 | 93.7 | 95.1 |

TABLE 14

The DX of the soluble hydrolysate from wheat starch: Enzymes: glucoamylase, acid fungal amylase and more acid fungal alpha-amylase with the CBM or without the CBM.

|  | 24 hours | 46 hours | 70 hours | 90 hours |
|---|---|---|---|---|
| Without CBM | 78.1 | 84.9 | 85.6 | 86.7 |
| With CBM | 82.3 | 88.4 | 89.5 | 905 |

TABLE 15

Soluble dry solids as percentage of total dry substance from corn grits. Enzymes: glucoamylase, acid fungal alpha-amylase and more acid fungal alpha-amylase with the CBM or without the CBM.

|  | 24 hours | 46 hours | 70 hours | 90 hours |
|---|---|---|---|---|
| Without CBM | 44.0 | 49.6 | 56.8 | 62.2 |
| With CBM | 53.6 | 59.7 | 63.8 | 68.4 |

TABLE 16

The DX of the soluble hydrolysate from corn grits: Enzymes: glucoamylase, acid fungal amylase and more acid fungal alpha-amylase with the CBM or without the CBM.

|  | 24 hours | 46 hours | 70 hours | 90 hours |
|---|---|---|---|---|
| Without CBM | 42.1 | 47.3 | 53.9 | 58.8 |
| With CBM | 51.2 | 56.8 | 60.4 | 64.5 |

The invention claimed is:

1. An isolated hybrid alpha-amylase which comprises an amino acid sequence of a catalytic module and an amino acid sequence of a carbohydrate binding module, wherein
   (a) the catalytic module comprises the amino acid sequence of SEQ ID NO:8; and
   (b) the carbohydrate binding module is an amino acid sequence having at least 90% homology to an amino acid sequence selected from the group consisting of SEQ ID NO:25.

2. The hybrid enzyme of claim 1, wherein the carbohydrate binding module has at least 95% homology to the amino acid sequence of SEQ ID NO:25.

3. The hybrid enzyme of claim 1, wherein the carbohydrate binding module comprises the amino acid sequence of SEQ ID NO:25.

4. The hybrid enzyme of claim 1, wherein the hybrid enzyme further comprises a linker amine acid sequence which connects the amino acid sequence of the catalytic module and the amino acid sequence of the carbohydrate-binding module.

5. The hybrid enzyme of claim 4, wherein the linker sequence is SEQ ID NO:27.

6. A method for liquefying starch, comprising treating a gelatinized or granular starch substrate with the hybrid enzyme of claim 1 in an aqueous medium.

7. A process for preparing dough-base product, comprising adding the hybrid enzyme of claim 1 to a dough.

* * * * *

```
                        SEQUENCE LISTING

<160> NUMBER OF SEQ ID NOS: 43

<210> SEQ ID NO 1
<211> LENGTH: 40
<212> TYPE: DNA
<213> ORGANISM: Artificial sequence
<220> FEATURE:
<223> OTHER INFORMATION: Synthetic construct

<400> SEQUENCE: 1
gaagggatcc gatttttact agtacatcca aagccaccac                              40

<210> SEQ ID NO 2
<211> LENGTH: 37
<212> TYPE: DNA
<213> ORGANISM: Artificial sequence
<220> FEATURE:
<223> OTHER INFORMATION: Synthetic construct

<400> SEQUENCE: 2
tttgtcgacc tacctccacg tatcaaccac cgtctcc                                 37

<210> SEQ ID NO 3
<211> LENGTH: 39
<212> TYPE: DNA
<213> ORGANISM: Artificial sequence
<220> FEATURE:
<223> OTHER INFORMATION: Synthetic construct

<400> SEQUENCE: 3
tttggatcca ccatgagatt atcgacttcg agtctcttc                               39

<210> SEQ ID NO 4
<211> LENGTH: 38
<212> TYPE: DNA
<213> ORGANISM: Artificial sequence
<220> FEATURE:
<223> OTHER INFORMATION: Synthetic construct

<400> SEQUENCE: 4
tttactagta gcagcagcag ttgtggtcgt ggttgttc                                38
```

-continued

```
<210> SEQ ID NO 5
<211> LENGTH: 396
<212> TYPE: DNA
<213> ORGANISM: Aspergillus kawachii
<220> FEATURE:
<221> NAME/KEY: CDS
<222> LOCATION: (1)..(396)

<400> SEQUENCE: 5 act agt aca tcc aaa gcc acc acc tcc tct tct tct tct gct gct       48
Thr Ser Thr Ser Lys Ala Thr Thr Ser Ser Ser Ser Ser Ala Ala
 1               5                  10                  15 gct act act tct tca tca tgc acc gca aca agc acc acc ctc ccc atc   96
Ala Thr Thr Ser Ser Ser Cys Thr Ala Thr Ser Thr Thr Leu Pro Ile
             20                  25                  30 acc ttc gaa gaa ctc gtc acc act acc tac ggg gaa gaa gtc tac ctc  144
Thr Phe Glu Glu Leu Val Thr Thr Thr Tyr Gly Glu Glu Val Tyr Leu
         35                  40                  45 agc gga tct atc tcc cag ctc gga gag tgg gat acg agt gac gcg gtg  192
Ser Gly Ser Ile Ser Gln Leu Gly Glu Trp Asp Thr Ser Asp Ala Val
     50                  55                  60 aag ttg tcc gcg gat gat tat acc tcg agt aac ccc gag tgg tct gtt  240
Lys Leu Ser Ala Asp Asp Tyr Thr Ser Ser Asn Pro Glu Trp Ser Val
 65                  70                  75                  80 act gtg tcg ttg ccg gtg ggg acg acc ttc gag tat aag ttt att aag  288
Thr Val Ser Leu Pro Val Gly Thr Thr Phe Glu Tyr Lys Phe Ile Lys
                 85                  90                  95 gtc gat gag ggt gga agt gtg act tgg gaa agt gat ccg aat agg gag  336
Val Asp Glu Gly Gly Ser Val Thr Trp Glu Ser Asp Pro Asn Arg Glu
            100                 105                 110 tat act gtg cct gaa tgt ggg aat ggg agt ggg gag acg gtg gtt gat  384
Tyr Thr Val Pro Glu Cys Gly Asn Gly Ser Gly Glu Thr Val Val Asp
        115                 120                 125 acg tgg agg tag                                                   396
Thr Trp Arg
    130

<210> SEQ ID NO 6
<211> LENGTH: 131
<212> TYPE: PRT
<213> ORGANISM: Aspergillus kawachii

<400> SEQUENCE: 6

Thr Ser Thr Ser Lys Ala Thr Thr Ser Ser Ser Ser Ser Ala Ala
 1               5                  10                  15

Ala Thr Thr Ser Ser Ser Cys Thr Ala Thr Ser Thr Thr Leu Pro Ile
             20                  25                  30

Thr Phe Glu Glu Leu Val Thr Thr Thr Tyr Gly Glu Glu Val Tyr Leu
         35                  40                  45

Ser Gly Ser Ile Ser Gln Leu Gly Glu Trp Asp Thr Ser Asp Ala Val
     50                  55                  60

Lys Leu Ser Ala Asp Asp Tyr Thr Ser Ser Asn Pro Glu Trp Ser Val
 65                  70                  75                  80

Thr Val Ser Leu Pro Val Gly Thr Thr Phe Glu Tyr Lys Phe Ile Lys
                 85                  90                  95

Val Asp Glu Gly Gly Ser Val Thr Trp Glu Ser Asp Pro Asn Arg Glu
            100                 105                 110

Tyr Thr Val Pro Glu Cys Gly Asn Gly Ser Gly Glu Thr Val Val Asp
        115                 120                 125

Thr Trp Arg
    130
```

<210> SEQ ID NO 7
<211> LENGTH: 1533
<212> TYPE: DNA
<213> ORGANISM: Aspergillus niger
<220> FEATURE:
<221> NAME/KEY: CDS
<222> LOCATION: (1)..(1533)

<400> SEQUENCE: 7

| | | | | | | | | | | | | | | | | |
|---|---|---|---|---|---|---|---|---|---|---|---|---|---|---|---|---|
| atg | aga | tta | tcg | act | tcg | agt | ctc | ttc | ctt | tcc | gtg | tct | ctg | ctg | ggg | 48 |
| Met | Arg | Leu | Ser | Thr | Ser | Ser | Leu | Phe | Leu | Ser | Val | Ser | Leu | Leu | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| aag | ctg | gcc | ctc | ggg | ctg | tcg | gct | gca | gaa | tgg | cgc | act | cag | tcg | att | 96 |
| Lys | Leu | Ala | Leu | Gly | Leu | Ser | Ala | Ala | Glu | Trp | Arg | Thr | Gln | Ser | Ile | |
| | | | 20 | | | | | 25 | | | | | 30 | | | |

| | | | | | | | | | | | | | | | | |
|---|---|---|---|---|---|---|---|---|---|---|---|---|---|---|---|---|
| tac | ttc | cta | ttg | acg | gat | cgg | ttc | ggt | agg | acg | gac | aat | tcg | acg | aca | 144 |
| Tyr | Phe | Leu | Leu | Thr | Asp | Arg | Phe | Gly | Arg | Thr | Asp | Asn | Ser | Thr | Thr | |
| | | | | 35 | | | | | 40 | | | | | 45 | | |

| | | | | | | | | | | | | | | | | |
|---|---|---|---|---|---|---|---|---|---|---|---|---|---|---|---|---|
| gct | aca | tgc | gat | acg | ggt | gac | caa | atc | tat | tgt | ggt | ggc | agt | tgg | caa | 192 |
| Ala | Thr | Cys | Asp | Thr | Gly | Asp | Gln | Ile | Tyr | Cys | Gly | Gly | Ser | Trp | Gln | |
| | 50 | | | | | 55 | | | | | 60 | | | | | |

| | | | | | | | | | | | | | | | | |
|---|---|---|---|---|---|---|---|---|---|---|---|---|---|---|---|---|
| gga | atc | atc | aac | cat | ctg | gat | tat | atc | cag | ggc | atg | gga | ttc | acg | gcc | 240 |
| Gly | Ile | Ile | Asn | His | Leu | Asp | Tyr | Ile | Gln | Gly | Met | Gly | Phe | Thr | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| atc | tgg | atc | tcg | cct | atc | act | gaa | cag | ctg | ccc | cag | gat | act | gct | gat | 288 |
| Ile | Trp | Ile | Ser | Pro | Ile | Thr | Glu | Gln | Leu | Pro | Gln | Asp | Thr | Ala | Asp | |
| | | | | 85 | | | | | 90 | | | | | 95 | | |

| | | | | | | | | | | | | | | | | |
|---|---|---|---|---|---|---|---|---|---|---|---|---|---|---|---|---|
| ggt | gaa | gct | tac | cat | gga | tat | tgg | cag | cag | aag | ata | tac | gac | gtg | aac | 336 |
| Gly | Glu | Ala | Tyr | His | Gly | Tyr | Trp | Gln | Gln | Lys | Ile | Tyr | Asp | Val | Asn | |
| | | | | 100 | | | | | 105 | | | | | 110 | | |

| | | | | | | | | | | | | | | | | |
|---|---|---|---|---|---|---|---|---|---|---|---|---|---|---|---|---|
| tcc | aac | ttc | ggc | act | gca | gat | gac | ctc | aag | tcc | ctc | tca | gat | gcg | ctt | 384 |
| Ser | Asn | Phe | Gly | Thr | Ala | Asp | Asp | Leu | Lys | Ser | Leu | Ser | Asp | Ala | Leu | |
| | | | 115 | | | | | 120 | | | | | 125 | | | |

| | | | | | | | | | | | | | | | | |
|---|---|---|---|---|---|---|---|---|---|---|---|---|---|---|---|---|
| cat | gcc | cgc | gga | atg | tac | ctc | atg | gtg | gac | gtc | gtc | cct | aac | cac | atg | 432 |
| His | Ala | Arg | Gly | Met | Tyr | Leu | Met | Val | Asp | Val | Val | Pro | Asn | His | Met | |
| | | 130 | | | | | 135 | | | | | 140 | | | | |

| | | | | | | | | | | | | | | | | |
|---|---|---|---|---|---|---|---|---|---|---|---|---|---|---|---|---|
| ggc | tac | gcc | ggc | aac | ggc | aac | gat | gta | gac | tac | agc | gtc | ttc | gac | ccc | 480 |
| Gly | Tyr | Ala | Gly | Asn | Gly | Asn | Asp | Val | Asp | Tyr | Ser | Val | Phe | Asp | Pro | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ttc | gat | tcc | tcc | tcc | tac | ttc | cac | cca | tac | tgc | ctg | atc | aca | gat | tgg | 528 |
| Phe | Asp | Ser | Ser | Ser | Tyr | Phe | His | Pro | Tyr | Cys | Leu | Ile | Thr | Asp | Trp | |
| | | | | 165 | | | | | 170 | | | | | 175 | | |

| | | | | | | | | | | | | | | | | |
|---|---|---|---|---|---|---|---|---|---|---|---|---|---|---|---|---|
| gac | aac | ttg | acc | atg | gtc | caa | gat | tgt | tgg | gag | ggt | gac | acc | atc | gta | 576 |
| Asp | Asn | Leu | Thr | Met | Val | Gln | Asp | Cys | Trp | Glu | Gly | Asp | Thr | Ile | Val | |
| | | | 180 | | | | | 185 | | | | | 190 | | | |

| | | | | | | | | | | | | | | | | |
|---|---|---|---|---|---|---|---|---|---|---|---|---|---|---|---|---|
| tct | ctg | cca | gac | cta | aac | acc | acc | gaa | act | gcc | gtg | aga | aca | atc | tgg | 624 |
| Ser | Leu | Pro | Asp | Leu | Asn | Thr | Thr | Glu | Thr | Ala | Val | Arg | Thr | Ile | Trp | |
| | | 195 | | | | | 200 | | | | | 205 | | | | |

| | | | | | | | | | | | | | | | | |
|---|---|---|---|---|---|---|---|---|---|---|---|---|---|---|---|---|
| tat | gac | tgg | gta | gcc | gac | ctg | gta | tcc | aat | tat | tca | gtc | gac | gga | ctc | 672 |
| Tyr | Asp | Trp | Val | Ala | Asp | Leu | Val | Ser | Asn | Tyr | Ser | Val | Asp | Gly | Leu | |
| | 210 | | | | | 215 | | | | | 220 | | | | | |

| | | | | | | | | | | | | | | | | |
|---|---|---|---|---|---|---|---|---|---|---|---|---|---|---|---|---|
| cgc | atc | gac | agt | gtc | ctc | gaa | gtc | gaa | cca | gac | ttc | ttc | ccg | ggc | tac | 720 |
| Arg | Ile | Asp | Ser | Val | Leu | Glu | Val | Glu | Pro | Asp | Phe | Phe | Pro | Gly | Tyr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| cag | gaa | gca | gca | ggt | gtc | tac | tgc | gtc | ggc | gaa | gtc | gac | aac | ggc | aac | 768 |
| Gln | Glu | Ala | Ala | Gly | Val | Tyr | Cys | Val | Gly | Glu | Val | Asp | Asn | Gly | Asn | |
| | | | | 245 | | | | | 250 | | | | | 255 | | |

| | | | | | | | | | | | | | | | | |
|---|---|---|---|---|---|---|---|---|---|---|---|---|---|---|---|---|
| cct | gcc | ctc | gac | tgc | cca | tac | cag | aag | gtc | ctg | gac | ggc | gtc | ctc | aac | 816 |
| Pro | Ala | Leu | Asp | Cys | Pro | Tyr | Gln | Lys | Val | Leu | Asp | Gly | Val | Leu | Asn | |
| | | | 260 | | | | | 265 | | | | | 270 | | | |

```
tat ccg atc tac tgg caa ctc ctc tac gcc ttc gaa tcc tcc agc ggc    864
Tyr Pro Ile Tyr Trp Gln Leu Leu Tyr Ala Phe Glu Ser Ser Ser Gly
    275                 280                 285 agc atc agc aat ctc tac aac atg atc aaa tcc gtc gca agc gac tgc    912
Ser Ile Ser Asn Leu Tyr Asn Met Ile Lys Ser Val Ala Ser Asp Cys
290                 295                 300 tcc gat ccg aca cta ctc ggc aac ttc atc gaa aac cac gac aat ccc    960
Ser Asp Pro Thr Leu Leu Gly Asn Phe Ile Glu Asn His Asp Asn Pro
305                 310                 315                 320 cgt ttc gcc tcc tac acc tcc gac tac tcg caa gcc aaa aac gtc ctc   1008
Arg Phe Ala Ser Tyr Thr Ser Asp Tyr Ser Gln Ala Lys Asn Val Leu
                325                 330                 335 agc tac atc ttc ctc tcc gac ggc atc ccc atc gtc tac gcc ggc gaa   1056
Ser Tyr Ile Phe Leu Ser Asp Gly Ile Pro Ile Val Tyr Ala Gly Glu
            340                 345                 350 gaa cag cac tac tcc ggc ggc aag gtg ccc tac aac cgc gaa gcg acc   1104
Glu Gln His Tyr Ser Gly Gly Lys Val Pro Tyr Asn Arg Glu Ala Thr
        355                 360                 365 tgg ctt tca ggc tac gac acc tcc gca gag ctg tac acc tgg ata gcc   1152
Trp Leu Ser Gly Tyr Asp Thr Ser Ala Glu Leu Tyr Thr Trp Ile Ala
370                 375                 380 acc acg aac gcg atc cgc aaa cta gcc atc tca gct gac tcg gcc tac   1200
Thr Thr Asn Ala Ile Arg Lys Leu Ala Ile Ser Ala Asp Ser Ala Tyr
385                 390                 395                 400 att acc tac gcg aat gat gca ttc tac act gac agc aac acc atc gca   1248
Ile Thr Tyr Ala Asn Asp Ala Phe Tyr Thr Asp Ser Asn Thr Ile Ala
                405                 410                 415 atg cgc aaa ggc acc tca ggg agc caa gtc atc acc gtc ctc tcc aac   1296
Met Arg Lys Gly Thr Ser Gly Ser Gln Val Ile Thr Val Leu Ser Asn
            420                 425                 430 aaa ggc tcc tca gga agc agc tac acc ctg acc ctc agc gga agc ggc   1344
Lys Gly Ser Ser Gly Ser Ser Tyr Thr Leu Thr Leu Ser Gly Ser Gly
        435                 440                 445 tac aca tcc ggc acg aag ctg atc gaa gcg tac aca tgc aca tcc gtg   1392
Tyr Thr Ser Gly Thr Lys Leu Ile Glu Ala Tyr Thr Cys Thr Ser Val
450                 455                 460 acc gtg gac tcg agc ggc gat att ccc gtg ccg atg gcg tcg gga tta   1440
Thr Val Asp Ser Ser Gly Asp Ile Pro Val Pro Met Ala Ser Gly Leu
465                 470                 475                 480 ccg aga gtt ctt ctg ccc gcg tcc gtc gtc gat agc tct tcg ctc tgt   1488
Pro Arg Val Leu Leu Pro Ala Ser Val Val Asp Ser Ser Ser Leu Cys
                485                 490                 495 ggc ggg agc gga aga aca acc acg acc aca act gct gct act agt        1533
Gly Gly Ser Gly Arg Thr Thr Thr Thr Thr Ala Ala Thr Ser
            500                 505                 510

<210> SEQ ID NO 8
<211> LENGTH: 511
<212> TYPE: PRT
<213> ORGANISM: Aspergillus niger

<400> SEQUENCE: 8

Met Arg Leu Ser Thr Ser Ser Leu Phe Leu Ser Val Ser Leu Leu Gly
1               5                   10                  15

Lys Leu Ala Leu Gly Leu Ser Ala Ala Glu Trp Arg Thr Gln Ser Ile
            20                  25                  30

Tyr Phe Leu Leu Thr Asp Arg Phe Gly Arg Thr Asp Asn Ser Thr Thr
        35                  40                  45

Ala Thr Cys Asp Thr Gly Asp Gln Ile Tyr Cys Gly Gly Ser Trp Gln
    50                  55                  60
```

-continued

```
Gly Ile Ile Asn His Leu Asp Tyr Ile Gln Gly Met Gly Phe Thr Ala
 65                  70                  75                  80

Ile Trp Ile Ser Pro Ile Thr Glu Gln Leu Pro Gln Asp Thr Ala Asp
             85                  90                  95

Gly Glu Ala Tyr His Gly Tyr Trp Gln Gln Lys Ile Tyr Asp Val Asn
            100                 105                 110

Ser Asn Phe Gly Thr Ala Asp Asp Leu Lys Ser Leu Ser Asp Ala Leu
            115                 120                 125

His Ala Arg Gly Met Tyr Leu Met Val Asp Val Val Pro Asn His Met
        130                 135                 140

Gly Tyr Ala Gly Asn Gly Asn Asp Val Asp Tyr Ser Val Phe Asp Pro
145                 150                 155                 160

Phe Asp Ser Ser Tyr Phe His Pro Tyr Cys Leu Ile Thr Asp Trp
            165                 170                 175

Asp Asn Leu Thr Met Val Gln Asp Cys Trp Glu Gly Asp Thr Ile Val
            180                 185                 190

Ser Leu Pro Asp Leu Asn Thr Thr Glu Thr Ala Val Arg Thr Ile Trp
        195                 200                 205

Tyr Asp Trp Val Ala Asp Leu Val Ser Asn Tyr Ser Val Asp Gly Leu
210                 215                 220

Arg Ile Asp Ser Val Leu Glu Val Glu Pro Asp Phe Phe Pro Gly Tyr
225                 230                 235                 240

Gln Glu Ala Ala Gly Val Tyr Cys Val Gly Glu Val Asp Asn Gly Asn
            245                 250                 255

Pro Ala Leu Asp Cys Pro Tyr Gln Lys Val Leu Asp Gly Val Leu Asn
            260                 265                 270

Tyr Pro Ile Tyr Trp Gln Leu Leu Tyr Ala Phe Glu Ser Ser Ser Gly
        275                 280                 285

Ser Ile Ser Asn Leu Tyr Asn Met Ile Lys Ser Val Ala Ser Asp Cys
        290                 295                 300

Ser Asp Pro Thr Leu Leu Gly Asn Phe Ile Glu Asn His Asp Asn Pro
305                 310                 315                 320

Arg Phe Ala Ser Tyr Thr Ser Asp Tyr Ser Gln Ala Lys Asn Val Leu
            325                 330                 335

Ser Tyr Ile Phe Leu Ser Asp Gly Ile Pro Ile Val Tyr Ala Gly Glu
            340                 345                 350

Glu Gln His Tyr Ser Gly Gly Lys Val Pro Tyr Asn Arg Glu Ala Thr
        355                 360                 365

Trp Leu Ser Gly Tyr Asp Thr Ser Ala Glu Leu Tyr Thr Trp Ile Ala
        370                 375                 380

Thr Thr Asn Ala Ile Arg Lys Leu Ala Ile Ser Ala Asp Ser Ala Tyr
385                 390                 395                 400

Ile Thr Tyr Ala Asn Asp Ala Phe Tyr Thr Asp Ser Asn Thr Ile Ala
            405                 410                 415

Met Arg Lys Gly Thr Ser Gly Ser Gln Val Ile Thr Val Leu Ser Asn
            420                 425                 430

Lys Gly Ser Ser Gly Ser Ser Tyr Thr Leu Thr Leu Ser Gly Ser Gly
        435                 440                 445

Tyr Thr Ser Gly Thr Lys Leu Ile Glu Ala Tyr Thr Cys Thr Ser Val
        450                 455                 460

Thr Val Asp Ser Ser Gly Asp Ile Pro Val Pro Met Ala Ser Gly Leu
465                 470                 475                 480

Pro Arg Val Leu Leu Pro Ala Ser Val Val Asp Ser Ser Ser Leu Cys
            485                 490                 495
```

-continued

```
Gly Gly Ser Gly Arg Thr Thr Thr Thr Thr Ala Ala Thr Ser
            500                 505                 510

<210> SEQ ID NO 9
<211> LENGTH: 102
<212> TYPE: PRT
<213> ORGANISM: Bacillus flavothermus

<400> SEQUENCE: 9

Ile Ser Thr Thr Ser Gln Ile Thr Phe Thr Val Asn Asn Ala Thr Thr
  1               5                  10                  15

Val Trp Gly Gln Asn Val Tyr Val Gly Asn Ile Ser Gln Leu Gly
             20                  25                  30

Asn Trp Asp Pro Val His Ala Val Gln Met Thr Pro Ser Ser Tyr Pro
         35                  40                  45

Thr Trp Thr Val Thr Ile Pro Leu Leu Gln Gly Gln Asn Ile Gln Phe
     50                  55                  60

Lys Phe Ile Lys Lys Asp Ser Ala Gly Asn Val Ile Trp Glu Asp Ile
 65                  70                  75                  80

Ser Asn Arg Thr Tyr Thr Val Pro Thr Ala Ala Ser Gly Ala Tyr Thr
                 85                  90                  95

Ala Ser Trp Asn Val Pro
            100

<210> SEQ ID NO 10
<211> LENGTH: 99
<212> TYPE: PRT
<213> ORGANISM: Bacillus species.

<400> SEQUENCE: 10

Thr Ser Asn Val Thr Phe Thr Val Asn Asn Ala Thr Thr Val Tyr Gly
  1               5                  10                  15

Gln Asn Val Tyr Val Val Gly Asn Ile Pro Glu Leu Gly Asn Trp Asn
             20                  25                  30

Ile Ala Asn Ala Ile Gln Met Thr Pro Ser Ser Tyr Pro Thr Trp Lys
         35                  40                  45

Thr Thr Val Ser Leu Pro Gln Gly Lys Ala Ile Glu Phe Lys Phe Ile
     50                  55                  60

Lys Lys Asp Ser Ala Gly Asn Val Ile Trp Glu Asn Ile Ala Asn Arg
 65                  70                  75                  80

Thr Tyr Thr Val Pro Phe Ser Ser Thr Gly Ser Tyr Thr Ala Asn Trp
                 85                  90                  95

Asn Val Pro

<210> SEQ ID NO 11
<211> LENGTH: 102
<212> TYPE: PRT
<213> ORGANISM: Alcaliphilic Bacillus

<400> SEQUENCE: 11

Thr Ser Thr Thr Ser Gln Ile Thr Phe Thr Val Asn Asn Ala Thr Thr
  1               5                  10                  15

Val Trp Gly Gln Asn Val Tyr Val Val Gly Asn Ile Ser Gln Leu Gly
             20                  25                  30

Asn Trp Asp Pro Val Asn Ala Val Gln Met Thr Pro Ser Ser Tyr Pro
         35                  40                  45

Thr Trp Val Val Thr Val Pro Leu Pro Gln Ser Gln Asn Ile Gln Phe
     50                  55                  60
```

```
Lys Phe Ile Lys Lys Asp Gly Ser Gly Asn Val Ile Trp Glu Asn Ile
 65                  70                  75                  80

Ser Asn Arg Thr Tyr Thr Val Pro Thr Ala Ser Gly Ala Tyr Thr
                 85                  90                  95

Ala Asn Trp Asn Val Pro
            100
```

<210> SEQ ID NO 12
<211> LENGTH: 112
<212> TYPE: PRT
<213> ORGANISM: Hormoconis resinae

<400> SEQUENCE: 12

```
Cys Gln Val Ser Ile Thr Phe Asn Ile Asn Ala Thr Thr Tyr Tyr Gly
  1               5                  10                  15

Glu Asn Leu Tyr Val Ile Gly Asn Ser Ser Asp Leu Gly Ala Trp Asn
             20                  25                  30

Ile Ala Asp Ala Tyr Pro Leu Ser Ala Ser Ala Tyr Thr Gln Asp Arg
         35                  40                  45

Pro Leu Trp Ser Ala Ala Ile Pro Leu Asn Ala Gly Glu Val Ile Ser
 50                  55                  60

Tyr Gln Tyr Val Arg Gln Glu Asp Cys Asp Gln Pro Tyr Ile Tyr Glu
 65                  70                  75                  80

Thr Val Asn Arg Thr Leu Thr Val Pro Ala Cys Gly Ala Ala Val
                 85                  90                  95

Thr Thr Asp Ala Trp Met Gly Pro Val Gly Ser Ser Gly Asn Cys
            100                 105                 110
```

<210> SEQ ID NO 13
<211> LENGTH: 95
<212> TYPE: PRT
<213> ORGANISM: Lentinula edodes

<400> SEQUENCE: 13

```
Val Ser Val Thr Phe Asn Val Asp Ala Ser Thr Leu Glu Gly Gln Asn
  1               5                  10                  15

Val Tyr Leu Thr Gly Ala Val Asp Ala Leu Glu Asp Trp Ser Thr Asp
             20                  25                  30

Asn Ala Ile Leu Leu Ser Ser Ala Asn Tyr Pro Thr Trp Ser Val Thr
         35                  40                  45

Val Asp Leu Pro Gly Ser Thr Val Gln Tyr Lys Tyr Ile Lys Lys
 50                  55                  60

Asp Gly Ser Gly Thr Val Thr Trp Glu Ser Pro Asn Met Glu Ile
 65                  70                  75                  80

Thr Thr Pro Ala Asn Gly Thr Tyr Ala Thr Asn Asp Thr Trp Arg
                 85                  90                  95
```

<210> SEQ ID NO 14
<211> LENGTH: 107
<212> TYPE: PRT
<213> ORGANISM: Neurospora crassa

<400> SEQUENCE: 14

```
Cys Ala Ala Asp His Glu Val Leu Val Thr Phe Asn Glu Lys Val Thr
  1               5                  10                  15

Thr Ser Tyr Gly Gln Thr Val Lys Val Gly Ser Ile Ala Ala Leu
             20                  25                  30

Gly Asn Trp Ala Pro Ala Ser Gly Val Thr Leu Ser Ala Lys Gln Tyr
```

```
                35                  40                  45
Ser Ser Ser Asn Pro Leu Trp Ser Thr Thr Ile Ala Leu Pro Gln Gly
 50                  55                  60

Thr Ser Phe Lys Tyr Lys Tyr Val Val Val Asn Ser Asp Gly Ser Val
65                  70                  75                  80

Lys Trp Glu Asn Asp Pro Asp Arg Ser Tyr Ala Val Gly Thr Asp Cys
                85                  90                  95

Ala Ser Thr Ala Thr Leu Asp Asp Thr Trp Arg
            100                 105

<210> SEQ ID NO 15
<211> LENGTH: 115
<212> TYPE: PRT
<213> ORGANISM: Talaromyces byssochlamydioides

<400> SEQUENCE: 15

Thr Thr Thr Gly Ala Ala Pro Cys Thr Thr Pro Thr Thr Val Ala Val
1               5                   10                  15

Thr Phe Asp Glu Ile Val Thr Thr Tyr Gly Glu Thr Val Tyr Leu
            20                  25                  30

Ser Gly Ser Ile Pro Ala Leu Gly Asn Trp Asp Thr Ser Ser Ala Ile
            35                  40                  45

Ala Leu Ser Ala Val Asp Tyr Thr Ser Ser Asn Pro Leu Trp Tyr Val
 50                  55                  60

Thr Val Asn Leu Pro Ala Gly Thr Ser Phe Glu Tyr Lys Phe Phe Val
65                  70                  75                  80

Gln Gln Thr Asp Gly Thr Ile Val Trp Glu Asp Pro Asn Arg Ser
                85                  90                  95

Tyr Thr Val Pro Ala Asn Cys Gly Gln Thr Thr Ala Ile Ile Asp Asp
            100                 105                 110

Ser Trp Gln
    115

<210> SEQ ID NO 16
<211> LENGTH: 115
<212> TYPE: PRT
<213> ORGANISM: Geosmithia cylindrospora:

<400> SEQUENCE: 16

Thr Ser Thr Gly Ser Ala Pro Cys Thr Thr Pro Thr Thr Val Ala Val
1               5                   10                  15

Thr Phe Asp Glu Ile Val Thr Thr Ser Tyr Gly Glu Thr Val Tyr Leu
            20                  25                  30

Ala Gly Ser Ile Ala Ala Leu Gly Asn Trp Asp Thr Asn Ser Ala Ile
            35                  40                  45

Ala Leu Ser Ala Ala Asp Tyr Thr Ser Asn Asn Asn Leu Trp Tyr Val
 50                  55                  60

Thr Val Asn Leu Ala Ala Gly Thr Ser Phe Gln Tyr Lys Phe Phe Val
65                  70                  75                  80

Lys Glu Thr Asp Ser Thr Ile Val Trp Glu Asp Pro Asn Arg Ser
                85                  90                  95

Tyr Thr Val Pro Ala Asn Cys Gly Gln Thr Thr Ala Ile Ile Asp Asp
            100                 105                 110

Thr Trp Gln
    115

<210> SEQ ID NO 17
```

```
<211> LENGTH: 139
<212> TYPE: PRT
<213> ORGANISM: Scorias spongiosa

<400> SEQUENCE: 17

Ala Lys Val Pro Ser Thr Cys Ser Ala Ser Ala Thr Gly Thr Cys
1               5                   10                  15

Thr Thr Ala Thr Ser Thr Phe Gly Gly Ser Pro Thr Thr Ser Cys
            20                  25                  30

Ala Thr Thr Pro Thr Leu Thr Val Leu Phe Asn Glu Arg Ala Thr
                35                  40                  45

Thr Asn Phe Gly Gln Asn Val His Leu Thr Gly Ser Ile Ser Gln Leu
    50                  55                  60

Gly Ser Trp Asp Thr Asp Ser Ala Val Ala Leu Ser Ala Val Asn Tyr
65                  70                  75                  80

Thr Ser Ser Asp Pro Leu Trp Phe Val Arg Val Gln Leu Pro Ala Gly
                85                  90                  95

Thr Ser Phe Gln Tyr Lys Tyr Phe Lys Lys Asp Ser Ser Asn Ala Val
                100                 105                 110

Ala Trp Glu Ser Asp Pro Asn Arg Ser Tyr Thr Val Pro Leu Asn Cys
            115                 120                 125

Ala Gly Thr Ala Thr Glu Asn Asp Thr Trp Arg
            130                 135

<210> SEQ ID NO 18
<211> LENGTH: 126
<212> TYPE: PRT
<213> ORGANISM: Eupenicillium ludwigii

<400> SEQUENCE: 18

Ser Thr Thr Thr Thr Ser Thr Thr Lys Thr Thr Thr Thr Ser Thr Thr
1               5                   10                  15

Thr Ser Cys Thr Thr Pro Thr Ala Val Ala Val Thr Phe Asp Leu Ile
            20                  25                  30

Ala Thr Thr Tyr Tyr Gly Glu Asn Ile Lys Ile Ala Gly Ser Ile Ser
                35                  40                  45

Gln Leu Gly Asp Trp Asp Thr Ser Asn Ala Val Ala Leu Ser Ala Ala
    50                  55                  60

Asp Tyr Thr Ser Ser Asp His Leu Trp Phe Val Asp Ile Asp Leu Pro
65                  70                  75                  80

Ala Gly Thr Val Phe Glu Tyr Lys Tyr Ile Arg Ile Glu Ser Asp Gly
                85                  90                  95

Ser Ile Glu Trp Glu Ser Asp Pro Asn Arg Ser Tyr Thr Val Pro Ala
                100                 105                 110

Ala Cys Ala Thr Thr Ala Val Thr Glu Asn Asp Thr Trp Arg
            115                 120                 125

<210> SEQ ID NO 19
<211> LENGTH: 116
<212> TYPE: PRT
<213> ORGANISM: Aspergillus japonicus

<400> SEQUENCE: 19

Lys Thr Ser Thr Thr Ser Ser Cys Ser Thr Pro Thr Ser Val Ala
1               5                   10                  15

Val Thr Phe Asp Val Ile Ala Thr Thr Thr Tyr Gly Glu Asn Val Tyr
            20                  25                  30

Ile Ser Gly Ser Ile Ser Gln Leu Gly Ser Trp Asp Thr Ser Ser Ala
```

Ile Ala Leu Ser Ala Ser Gln Tyr Thr Ser Ser Asn Asn Leu Trp Tyr
50                  55                  60

Ala Thr Val His Leu Pro Ala Gly Thr Phe Gln Tyr Lys Tyr Ile
65                  70                  75                  80

Arg Lys Glu Thr Asp Gly Ser Val Thr Trp Glu Ser Asp Pro Asn Arg
                85                  90                  95

Ser Tyr Thr Val Pro Ser Ser Cys Gly Val Ser Ser Ala Thr Glu Ser
                100                 105                 110

Asp Thr Trp Arg
        115

<210> SEQ ID NO 20
<211> LENGTH: 133
<212> TYPE: PRT
<213> ORGANISM: Penicillium cf. miczynskii

<400> SEQUENCE: 20

Thr Thr Thr Gly Gly Thr Thr Thr Ser Gln Gly Ser Thr Thr Thr Thr
1               5                   10                  15

Ser Lys Thr Ser Thr Thr Thr Ser Ser Cys Thr Ala Pro Thr Ser Val
                20                  25                  30

Ala Val Thr Phe Asp Leu Ile Ala Thr Val Tyr Asp Glu Asn Val
            35                  40                  45

Gln Leu Ala Gly Ser Ile Ser Ala Leu Gly Ser Trp Asp Thr Ser Ser
50                  55                  60

Ala Ile Arg Leu Ser Ala Ser Gln Tyr Thr Ser Ser Asn His Leu Trp
65                  70                  75                  80

Tyr Val Ala Val Ser Leu Pro Ala Gly Gln Val Phe Gln Tyr Lys Tyr
                85                  90                  95

Ile Arg Val Ala Ser Ser Gly Thr Ile Thr Trp Glu Ser Asp Pro Asn
                100                 105                 110

Leu Ser Tyr Thr Val Pro Val Ala Cys Ala Ala Thr Ala Val Thr Ile
            115                 120                 125

Ser Asp Thr Trp Arg
        130

<210> SEQ ID NO 21
<211> LENGTH: 116
<212> TYPE: PRT
<213> ORGANISM: Mz1 Penicillium species.

<400> SEQUENCE: 21

Thr Lys Thr Ser Thr Ser Thr Ser Cys Thr Thr Pro Thr Ala Val Ala
1               5                   10                  15

Val Thr Phe Asp Leu Ile Ala Thr Thr Thr Tyr Gly Glu Asn Ile Lys
                20                  25                  30

Ile Ala Gly Ser Ile Ala Ala Leu Gly Ala Trp Asp Thr Asp Asp Ala
            35                  40                  45

Val Ala Leu Ser Ala Ala Asp Tyr Thr Asp Ser Asp His Leu Trp Phe
50                  55                  60

Val Thr Gln Ser Ile Pro Ala Gly Thr Val Phe Glu Tyr Lys Tyr Ile
65                  70                  75                  80

Arg Val Glu Ser Asp Gly Thr Ile Glu Trp Glu Ser Asp Pro Asn Arg
                85                  90                  95

Ser Tyr Thr Val Pro Ala Ala Cys Ala Thr Thr Ala Val Thr Glu Ser
                100                 105                 110

Asp Thr Trp Arg
        115

<210> SEQ ID NO 22
<211> LENGTH: 114
<212> TYPE: PRT
<213> ORGANISM: Thysanophora species

<400> SEQUENCE: 22

Phe Thr Ser Thr Thr Lys Thr Ser Cys Thr Thr Pro Thr Ser Val Ala
1               5                   10                  15

Val Thr Phe Asp Leu Ile Ala Thr Thr Thr Tyr Gly Glu Ser Ile Arg
            20                  25                  30

Leu Val Gly Ser Ile Ser Glu Leu Gly Asp Trp Asp Thr Gly Ser Ala
        35                  40                  45

Ile Ala Leu His Ala Thr Asp Tyr Thr Asp Ser Asp His Leu Trp Phe
    50                  55                  60

Val Thr Val Gly Leu Pro Ala Gly Ala Ser Phe Glu Tyr Lys Tyr Ile
65                  70                  75                  80

Arg Val Glu Ser Ser Gly Thr Ile Glu Trp Glu Ser Asp Pro Asn Arg
                85                  90                  95

Ser Tyr Thr Val Pro Ala Ala Cys Ala Thr Thr Ala Val Thr Glu Ser
            100                 105                 110

Asp Thr

<210> SEQ ID NO 23
<211> LENGTH: 111
<212> TYPE: PRT
<213> ORGANISM: Humicola grisea var. thermoidea

<400> SEQUENCE: 23

Ala Asp Ala Ser Glu Val Tyr Val Thr Phe Asn Glu Arg Val Ser Thr
1               5                   10                  15

Ala Trp Gly Glu Thr Ile Lys Val Val Gly Asn Val Pro Ala Leu Gly
            20                  25                  30

Asn Trp Asp Thr Ser Lys Ala Val Thr Leu Ser Ala Ser Gly Tyr Lys
        35                  40                  45

Ser Asn Asp Pro Leu Trp Ser Ile Thr Val Pro Ile Lys Ala Thr Gly
    50                  55                  60

Ser Ala Val Gln Tyr Lys Tyr Ile Lys Val Gly Thr Asn Gly Lys Ile
65                  70                  75                  80

Thr Trp Glu Ser Asp Pro Asn Arg Ser Ile Thr Leu Gln Thr Ala Ser
                85                  90                  95

Ser Ala Gly Lys Cys Ala Ala Gln Thr Val Asn Asp Ser Trp Arg
            100                 105                 110

<210> SEQ ID NO 24
<211> LENGTH: 108
<212> TYPE: PRT
<213> ORGANISM: Aspergillus niger

<400> SEQUENCE: 24

Cys Thr Thr Pro Thr Ala Val Ala Val Thr Phe Asp Leu Thr Ala Thr
1               5                   10                  15

Thr Thr Tyr Gly Glu Asn Ile Tyr Leu Val Gly Ser Ile Ser Gln Leu
            20                  25                  30

Gly Asp Trp Glu Thr Ser Asp Gly Ile Ala Leu Ser Ala Asp Lys Tyr
        35                  40                  45

```
Thr Ser Ser Asp Pro Leu Trp Tyr Val Thr Val Thr Leu Pro Ala Gly
     50                  55                  60

Glu Ser Phe Glu Tyr Lys Phe Ile Arg Ile Glu Ser Asp Asp Ser Val
 65                  70                  75                  80

Glu Trp Glu Ser Asp Pro Asn Arg Glu Tyr Thr Val Pro Gln Ala Cys
             85                  90                  95

Gly Thr Ser Thr Ala Thr Val Thr Asp Thr Trp Arg
            100                 105
```

<210> SEQ ID NO 25
<211> LENGTH: 97
<212> TYPE: PRT
<213> ORGANISM: Aspergillus rolfsii

<400> SEQUENCE: 25

```
Val Glu Val Thr Phe Asp Val Tyr Ala Thr Val Tyr Gly Gln Asn
 1               5                  10                  15

Ile Tyr Ile Thr Gly Asp Val Ser Glu Leu Gly Asn Trp Thr Pro Ala
             20                  25                  30

Asn Gly Val Ala Leu Ser Ser Ala Asn Tyr Pro Thr Trp Ser Ala Thr
             35                  40                  45

Ile Ala Leu Pro Ala Asp Thr Thr Ile Gln Tyr Lys Tyr Val Asn Ile
 50                  55                  60

Asp Gly Ser Thr Val Ile Trp Glu Asp Ala Ile Ser Asn Arg Glu Ile
 65                  70                  75                  80

Thr Thr Pro Ala Ser Gly Thr Tyr Thr Glu Lys Asp Thr Trp Asp Glu
             85                  90                  95

Ser
```

<210> SEQ ID NO 26
<211> LENGTH: 38
<212> TYPE: PRT
<213> ORGANISM: Aspergillus niger

<400> SEQUENCE: 26

```
Thr Gly Gly Thr Thr Thr Thr Ala Thr Pro Thr Gly Ser Gly Ser Val
 1               5                  10                  15

Thr Ser Thr Ser Lys Thr Thr Ala Thr Ala Ser Lys Thr Ser Thr Ser
             20                  25                  30

Thr Ser Ser Thr Ser Ala
         35
```

<210> SEQ ID NO 27
<211> LENGTH: 31
<212> TYPE: PRT
<213> ORGANISM: Aspergillus kawachii

<400> SEQUENCE: 27

```
Thr Thr Thr Thr Thr Thr Ala Ala Ala Thr Ser Thr Ser Lys Ala Thr
 1               5                  10                  15

Thr Ser Ser Ser Ser Ser Ser Ala Ala Ala Thr Thr Ser Ser Ser
             20                  25                  30
```

<210> SEQ ID NO 28
<211> LENGTH: 11
<212> TYPE: PRT
<213> ORGANISM: Athelia rolfsii

<400> SEQUENCE: 28

```
Gly Ala Thr Ser Pro Gly Gly Ser Ser Gly Ser
1               5                   10
```

<210> SEQ ID NO 29
<211> LENGTH: 8
<212> TYPE: PRT
<213> ORGANISM: Artificial sequence
<220> FEATURE:
<223> OTHER INFORMATION: Synthetic construct

<400> SEQUENCE: 29

```
Pro Glu Pro Thr Pro Glu Pro Thr
1               5
```

<210> SEQ ID NO 30
<211> LENGTH: 498
<212> TYPE: PRT
<213> ORGANISM: Aspergillus oryzae

<400> SEQUENCE: 30

```
Met Val Ala Trp Trp Ser Leu Phe Leu Tyr Gly Leu Gln Val Ala Ala
1               5                   10                  15

Pro Ala Leu Ala Ala Thr Pro Ala Asp Trp Arg Ser Gln Ser Ile Tyr
            20                  25                  30

Phe Leu Leu Thr Asp Arg Phe Ala Arg Thr Asp Gly Ser Thr Thr Ala
        35                  40                  45

Thr Cys Asn Thr Ala Asp Gln Lys Tyr Cys Gly Gly Thr Trp Gln Gly
    50                  55                  60

Ile Ile Asp Lys Leu Asp Tyr Ile Gln Gly Met Gly Phe Thr Ala Ile
65                  70                  75                  80

Trp Ile Thr Pro Val Thr Ala Gln Leu Pro Gln Thr Thr Ala Tyr Gly
                85                  90                  95

Asp Ala Tyr His Gly Tyr Trp Gln Gln Asp Ile Tyr Ser Leu Asn Glu
            100                 105                 110

Asn Tyr Gly Thr Ala Asp Asp Leu Lys Ala Leu Ser Ser Ala Leu His
        115                 120                 125

Glu Arg Gly Met Tyr Leu Met Val Asp Val Val Ala Asn His Met Gly
    130                 135                 140

Tyr Asp Gly Ala Gly Ser Ser Val Asp Tyr Ser Val Phe Lys Pro Phe
145                 150                 155                 160

Ser Ser Gln Asp Tyr Phe His Pro Phe Cys Phe Ile Gln Asn Tyr Glu
                165                 170                 175

Asp Gln Thr Gln Val Glu Asp Cys Trp Leu Gly Asp Asn Thr Val Ser
            180                 185                 190

Leu Pro Asp Leu Asp Thr Thr Lys Asp Val Val Lys Asn Glu Trp Tyr
        195                 200                 205

Asp Trp Val Gly Ser Leu Val Ser Asn Tyr Ser Ile Asp Gly Leu Arg
    210                 215                 220

Ile Asp Thr Val Lys His Val Gln Lys Asp Phe Trp Pro Gly Tyr Asn
225                 230                 235                 240

Lys Ala Ala Gly Val Tyr Cys Ile Gly Glu Val Leu Asp Gly Asp Pro
                245                 250                 255

Ala Tyr Thr Cys Pro Tyr Gln Asn Val Met Asp Gly Val Leu Asn Tyr
            260                 265                 270

Pro Ile Tyr Tyr Pro Leu Leu Asn Ala Phe Lys Ser Thr Ser Gly Ser
        275                 280                 285

Met Asp Asp Leu Tyr Asn Met Ile Asn Thr Val Lys Ser Asp Cys Pro
    290                 295                 300
```

| | | | | | | | | | | | | | | | |
|---|---|---|---|---|---|---|---|---|---|---|---|---|---|---|---|
|Asp|Ser|Thr|Leu|Leu|Gly|Thr|Phe|Val|Glu|Asn|His|Asp|Asn|Pro|Arg|
|305| | | |310| | | |315| | | |320| | | |

Phe Ala Ser Tyr Thr Asn Asp Ile Ala Leu Ala Lys Asn Val Ala Ala
                325                 330                 335

Phe Ile Ile Leu Asn Asp Gly Ile Pro Ile Ile Tyr Ala Gly Gln Glu
            340                 345                 350

Gln His Tyr Ala Gly Gly Asn Asp Pro Ala Asn Arg Glu Ala Thr Trp
        355                 360                 365

Leu Ser Gly Tyr Pro Thr Asp Ser Glu Leu Tyr Lys Leu Ile Ala Ser
    370                 375                 380

Ala Asn Ala Ile Arg Asn Tyr Ala Ile Ser Lys Asp Thr Gly Phe Val
385                 390                 395                 400

Thr Tyr Lys Asn Trp Pro Ile Tyr Lys Asp Asp Thr Thr Ile Ala Met
                405                 410                 415

Arg Lys Gly Thr Asp Gly Ser Gln Ile Val Thr Ile Leu Ser Asn Lys
            420                 425                 430

Gly Ala Ser Gly Asp Ser Tyr Thr Leu Ser Leu Ser Gly Ala Gly Tyr
        435                 440                 445

Thr Ala Gly Gln Gln Leu Thr Glu Val Ile Gly Cys Thr Thr Val Thr
    450                 455                 460

Val Gly Ser Asp Gly Asn Val Pro Val Pro Met Ala Gly Gly Leu Pro
465                 470                 475                 480

Arg Val Leu Tyr Pro Thr Glu Lys Leu Ala Gly Ser Lys Ile Cys Ser
                485                 490                 495

Ser Ser

<210> SEQ ID NO 31
<211> LENGTH: 1923
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(1923)

<400> SEQUENCE: 31

```
atg aga tta tcg act tcg agt ctc ttc ctt tcc gtg tct ctg ctg ggg      48
Met Arg Leu Ser Thr Ser Ser Leu Phe Leu Ser Val Ser Leu Leu Gly
1               5                   10                  15 aag ctg gcc ctc ggg ctg tcg gct gca gaa tgg cgc act cag tcg att      96
Lys Leu Ala Leu Gly Leu Ser Ala Ala Glu Trp Arg Thr Gln Ser Ile
            20                  25                  30 tac ttc cta ttg acg gat cgg ttc ggt agg acg gac aat tcg acg aca     144
Tyr Phe Leu Leu Thr Asp Arg Phe Gly Arg Thr Asp Asn Ser Thr Thr
        35                  40                  45 gct aca tgc gat acg ggt gac caa atc tat tgt ggt ggc agt tgg caa     192
Ala Thr Cys Asp Thr Gly Asp Gln Ile Tyr Cys Gly Gly Ser Trp Gln
    50                  55                  60 gga atc atc aac cat ctg gat tat atc cag ggc atg gga ttc acg gcc     240
Gly Ile Ile Asn His Leu Asp Tyr Ile Gln Gly Met Gly Phe Thr Ala
65                  70                  75                  80 atc tgg atc tcg cct atc act gaa cag ctg ccc cag gat act gct gat     288
Ile Trp Ile Ser Pro Ile Thr Glu Gln Leu Pro Gln Asp Thr Ala Asp
                85                  90                  95 ggt gaa gct tac cat gga tat tgg cag cag aag ata tac gac gtg aac     336
Gly Glu Ala Tyr His Gly Tyr Trp Gln Gln Lys Ile Tyr Asp Val Asn
            100                 105                 110
```

| | | |
|---|---|---|
| tcc aac ttc ggc act gca gat gac ctc aag tcc ctc tca gat gcg ctt<br>Ser Asn Phe Gly Thr Ala Asp Asp Leu Lys Ser Leu Ser Asp Ala Leu<br>115                        120                      125 | 384 |
| cat gcc cgc gga atg tac ctc atg gtg gac gtc gtc cct aac cac atg<br>His Ala Arg Gly Met Tyr Leu Met Val Asp Val Val Pro Asn His Met<br>130                        135                      140 | 432 |
| ggc tac gcc ggc aac ggc aac gat gta gac tac agc gtc ttc gac ccc<br>Gly Tyr Ala Gly Asn Gly Asn Asp Val Asp Tyr Ser Val Phe Asp Pro<br>145                        150                      155                      160 | 480 |
| ttc gat tcc tcc tcc tac ttc cac cca tac tgc ctg atc aca gat tgg<br>Phe Asp Ser Ser Ser Tyr Phe His Pro Tyr Cys Leu Ile Thr Asp Trp<br>                      165                      170                      175 | 528 |
| gac aac ttg acc atg gtc caa gat tgt tgg gag ggt gac acc atc gta<br>Asp Asn Leu Thr Met Val Gln Asp Cys Trp Glu Gly Asp Thr Ile Val<br>180                        185                      190 | 576 |
| tct ctg cca gac cta aac acc acc gaa act gcc gtg aga aca atc tgg<br>Ser Leu Pro Asp Leu Asn Thr Thr Glu Thr Ala Val Arg Thr Ile Trp<br>195                        200                      205 | 624 |
| tat gac tgg gta gcc gac ctg gta tcc aat tat tca gtc gac gga ctc<br>Tyr Asp Trp Val Ala Asp Leu Val Ser Asn Tyr Ser Val Asp Gly Leu<br>210                        215                      220 | 672 |
| cgc atc gac agt gtc ctc gaa gtc gaa cca gac ttc ttc ccg ggc tac<br>Arg Ile Asp Ser Val Leu Glu Val Glu Pro Asp Phe Phe Pro Gly Tyr<br>225                        230                      235                      240 | 720 |
| cag gaa gca gca ggt gtc tac tgc gtc ggc gaa gtc gac aac ggc aac<br>Gln Glu Ala Ala Gly Val Tyr Cys Val Gly Glu Val Asp Asn Gly Asn<br>                      245                      250                      255 | 768 |
| cct gcc ctc gac tgc cca tac cag aag gtc ctc gac ggc gtc ctc aac<br>Pro Ala Leu Asp Cys Pro Tyr Gln Lys Val Leu Asp Gly Val Leu Asn<br>                      260                      265                      270 | 816 |
| tat ccg atc tac tgg caa ctc ctc tac gcc ttc gaa tcc tcc agc ggc<br>Tyr Pro Ile Tyr Trp Gln Leu Leu Tyr Ala Phe Glu Ser Ser Ser Gly<br>275                        280                      285 | 864 |
| agc atc agc aat ctc tac aac atg atc aaa tcc gtc gca agc gac tgc<br>Ser Ile Ser Asn Leu Tyr Asn Met Ile Lys Ser Val Ala Ser Asp Cys<br>290                        295                      300 | 912 |
| tcc gat ccg aca cta ctc ggc aac ttc atc gaa aac cac gac aat ccc<br>Ser Asp Pro Thr Leu Leu Gly Asn Phe Ile Glu Asn His Asp Asn Pro<br>305                        310                      315                      320 | 960 |
| cgt ttc gcc tcc tac acc tcc gac tac tcg caa gcc aaa aac gtc ctc<br>Arg Phe Ala Ser Tyr Thr Ser Asp Tyr Ser Gln Ala Lys Asn Val Leu<br>                      325                      330                      335 | 1008 |
| agc tac atc ttc ctc tcc gac ggc atc ccc atc gtc tac gcc ggc gaa<br>Ser Tyr Ile Phe Leu Ser Asp Gly Ile Pro Ile Val Tyr Ala Gly Glu<br>                      340                      345                      350 | 1056 |
| gaa cag cac tac tcc ggc ggc aag gtg ccc tac aac cgc gaa gcg acc<br>Glu Gln His Tyr Ser Gly Gly Lys Val Pro Tyr Asn Arg Glu Ala Thr<br>                      355                      360                      365 | 1104 |
| tgg ctt tca ggc tac gac acc tcc gca gag ctg tac acc tgg ata gcc<br>Trp Leu Ser Gly Tyr Asp Thr Ser Ala Glu Leu Tyr Thr Trp Ile Ala<br>370                        375                      380 | 1152 |
| acc acg aac gcg atc cgc aaa cta gcc atc tca gct gac tcg gcc tac<br>Thr Thr Asn Ala Ile Arg Lys Leu Ala Ile Ser Ala Asp Ser Ala Tyr<br>385                        390                      395                      400 | 1200 |
| att acc tac gcg aat gat gca ttc tac act gac agc aac acc atc gca<br>Ile Thr Tyr Ala Asn Asp Ala Phe Tyr Thr Asp Ser Asn Thr Ile Ala<br>                      405                      410                      415 | 1248 |
| atg cgc aaa ggc acc tca ggg agc caa gtc atc acc gtc ctc tcc aac<br>Met Arg Lys Gly Thr Ser Gly Ser Gln Val Ile Thr Val Leu Ser Asn<br>                      420                      425                      430 | 1296 |

```
aaa ggc tcc tca gga agc agc tac acc ctg acc ctc agc gga agc ggc      1344
Lys Gly Ser Ser Gly Ser Ser Tyr Thr Leu Thr Leu Ser Gly Ser Gly
            435                 440                 445 tac aca tcc ggc acg aag ctg atc gaa gcg tac aca tgc aca tcc gtg      1392
Tyr Thr Ser Gly Thr Lys Leu Ile Glu Ala Tyr Thr Cys Thr Ser Val
        450                 455                 460 acc gtg gac tcg agc ggc gat att ccc gtg ccg atg gcg tcg gga tta      1440
Thr Val Asp Ser Ser Gly Asp Ile Pro Val Pro Met Ala Ser Gly Leu
465                 470                 475                 480 ccg aga gtt ctt ctg ccc gcg tcc gtc gtc gat agc tct tcg ctc tgt      1488
Pro Arg Val Leu Leu Pro Ala Ser Val Val Asp Ser Ser Ser Leu Cys
                485                 490                 495 ggc ggg agc gga aga aca acc acg acc aca act gct gct gct act agt      1536
Gly Gly Ser Gly Arg Thr Thr Thr Thr Thr Thr Ala Ala Ala Thr Ser
            500                 505                 510 aca tcc aaa gcc acc acc tcc tct tct tct tct gct gct gct act         1584
Thr Ser Lys Ala Thr Thr Ser Ser Ser Ser Ser Ala Ala Ala Thr
        515                 520                 525 act tct tca tca tgt acc act ccc acc gcc gtg gct gtg act ttc gat      1632
Thr Ser Ser Ser Cys Thr Thr Pro Thr Ala Val Ala Val Thr Phe Asp
530                 535                 540 ctg aca gct acc acc acc tac ggc gag aac atc tac ctg gtc gga tcg      1680
Leu Thr Ala Thr Thr Thr Tyr Gly Glu Asn Ile Tyr Leu Val Gly Ser
545                 550                 555                 560 atc tct cag ctg ggt gac tgg gaa acc agc gac ggc ata gct ctg agt      1728
Ile Ser Gln Leu Gly Asp Trp Glu Thr Ser Asp Gly Ile Ala Leu Ser
                565                 570                 575 gct gac aag tac act tcc agc gac ccg ctc tgg tat gtc act gtg act      1776
Ala Asp Lys Tyr Thr Ser Ser Asp Pro Leu Trp Tyr Val Thr Val Thr
            580                 585                 590 ctg ccg gct ggt gag tcg ttt gag tac aag ttt atc cgc att gag agc      1824
Leu Pro Ala Gly Glu Ser Phe Glu Tyr Lys Phe Ile Arg Ile Glu Ser
        595                 600                 605 gat gac tcc gtg gag tgg gag agt gat ccc aac cga gaa tac acc gtt      1872
Asp Asp Ser Val Glu Trp Glu Ser Asp Pro Asn Arg Glu Tyr Thr Val
610                 615                 620 cct cag gcg tgc gga acg tcg acc gcg acg gtg act gac acc tgg cgg      1920
Pro Gln Ala Cys Gly Thr Ser Thr Ala Thr Val Thr Asp Thr Trp Arg
625                 630                 635                 640 tag                                                                   1923
```

<210> SEQ ID NO 32
<211> LENGTH: 640
<212> TYPE: PRT
<213> ORGANISM: Artificial sequence
<220> FEATURE:
<223> OTHER INFORMATION: Synthetic Construct

<400> SEQUENCE: 32

```
Met Arg Leu Ser Thr Ser Ser Leu Phe Leu Ser Val Ser Leu Leu Gly
1               5                   10                  15

Lys Leu Ala Leu Gly Leu Ser Ala Ala Glu Trp Arg Thr Gln Ser Ile
            20                  25                  30

Tyr Phe Leu Leu Thr Asp Arg Phe Gly Arg Thr Asp Asn Ser Thr Thr
        35                  40                  45

Ala Thr Cys Asp Thr Gly Asp Gln Ile Tyr Cys Gly Gly Ser Trp Gln
    50                  55                  60

Gly Ile Ile Asn His Leu Asp Tyr Ile Gln Gly Met Gly Phe Thr Ala
65                  70                  75                  80

Ile Trp Ile Ser Pro Ile Thr Glu Gln Leu Pro Gln Asp Thr Ala Asp
```

```
                    85                  90                  95
Gly Glu Ala Tyr His Gly Tyr Trp Gln Gln Lys Ile Tyr Asp Val Asn
                100                 105                 110

Ser Asn Phe Gly Thr Ala Asp Asp Leu Lys Ser Leu Ser Asp Ala Leu
                115                 120                 125

His Ala Arg Gly Met Tyr Leu Met Val Asp Val Val Pro Asn His Met
                130                 135                 140

Gly Tyr Ala Gly Asn Gly Asn Asp Val Asp Tyr Ser Val Phe Asp Pro
145                 150                 155                 160

Phe Asp Ser Ser Tyr Phe His Pro Tyr Cys Leu Ile Thr Asp Trp
                    165                 170                 175

Asp Asn Leu Thr Met Val Gln Asp Cys Trp Glu Gly Asp Thr Ile Val
                180                 185                 190

Ser Leu Pro Asp Leu Asn Thr Thr Glu Thr Ala Val Arg Thr Ile Trp
                195                 200                 205

Tyr Asp Trp Val Ala Asp Leu Val Ser Asn Tyr Ser Val Asp Gly Leu
                210                 215                 220

Arg Ile Asp Ser Val Leu Glu Val Glu Pro Asp Phe Phe Pro Gly Tyr
225                 230                 235                 240

Gln Glu Ala Ala Gly Val Tyr Cys Val Gly Glu Val Asp Asn Gly Asn
                    245                 250                 255

Pro Ala Leu Asp Cys Pro Tyr Gln Lys Val Leu Asp Gly Val Leu Asn
                260                 265                 270

Tyr Pro Ile Tyr Trp Gln Leu Leu Tyr Ala Phe Glu Ser Ser Ser Gly
                275                 280                 285

Ser Ile Ser Asn Leu Tyr Asn Met Ile Lys Ser Val Ala Ser Asp Cys
                290                 295                 300

Ser Asp Pro Thr Leu Leu Gly Asn Phe Ile Glu Asn His Asp Asn Pro
305                 310                 315                 320

Arg Phe Ala Ser Tyr Thr Ser Asp Tyr Ser Gln Ala Lys Asn Val Leu
                    325                 330                 335

Ser Tyr Ile Phe Leu Ser Asp Gly Ile Pro Ile Val Tyr Ala Gly Glu
                340                 345                 350

Glu Gln His Tyr Ser Gly Gly Lys Val Pro Tyr Asn Arg Glu Ala Thr
                355                 360                 365

Trp Leu Ser Gly Tyr Asp Thr Ser Ala Glu Leu Tyr Thr Trp Ile Ala
                370                 375                 380

Thr Thr Asn Ala Ile Arg Lys Leu Ala Ile Ser Ala Asp Ser Ala Tyr
385                 390                 395                 400

Ile Thr Tyr Ala Asn Asp Ala Phe Tyr Thr Asp Ser Asn Thr Ile Ala
                    405                 410                 415

Met Arg Lys Gly Thr Ser Gly Ser Gln Val Ile Thr Val Leu Ser Asn
                420                 425                 430

Lys Gly Ser Ser Gly Ser Ser Tyr Thr Leu Thr Leu Ser Gly Ser Gly
                435                 440                 445

Tyr Thr Ser Gly Thr Lys Leu Ile Glu Ala Tyr Thr Cys Thr Ser Val
                450                 455                 460

Thr Val Asp Ser Ser Gly Asp Ile Pro Val Pro Met Ala Ser Gly Leu
465                 470                 475                 480

Pro Arg Val Leu Leu Pro Ala Ser Val Val Asp Ser Ser Ser Leu Cys
                    485                 490                 495

Gly Gly Ser Gly Arg Thr Thr Thr Thr Thr Ala Ala Ala Thr Ser
                500                 505                 510
```

```
Thr Ser Lys Ala Thr Thr Ser Ser Ser Ser Ala Ala Ala Thr
    515                 520                 525

Thr Ser Ser Ser Cys Thr Thr Pro Thr Ala Val Ala Val Thr Phe Asp
    530                 535                 540

Leu Thr Ala Thr Thr Thr Tyr Gly Glu Asn Ile Tyr Leu Val Gly Ser
545                 550                 555                 560

Ile Ser Gln Leu Gly Asp Trp Glu Thr Ser Asp Gly Ile Ala Leu Ser
                565                 570                 575

Ala Asp Lys Tyr Thr Ser Asp Pro Leu Trp Tyr Val Thr Val Thr
            580                 585                 590

Leu Pro Ala Gly Glu Ser Phe Glu Tyr Lys Phe Ile Arg Ile Glu Ser
        595                 600                 605

Asp Asp Ser Val Glu Trp Glu Ser Asp Pro Asn Arg Glu Tyr Thr Val
    610                 615                 620

Pro Gln Ala Cys Gly Thr Ser Thr Ala Thr Val Thr Asp Thr Trp Arg
625                 630                 635                 640

<210> SEQ ID NO 33
<211> LENGTH: 1890
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(1890)

<400> SEQUENCE: 33 atg aga tta tcg act tcg agt ctc ttc ctt tcc gtg tct ctg ctg ggg    48
Met Arg Leu Ser Thr Ser Ser Leu Phe Leu Ser Val Ser Leu Leu Gly
1               5                   10                  15 aag ctg gcc ctc ggg ctg tcg gct gca gaa tgg cgc act cag tcg att    96
Lys Leu Ala Leu Gly Leu Ser Ala Ala Glu Trp Arg Thr Gln Ser Ile
            20                  25                  30 tac ttc cta ttg acg gat cgg ttc ggt agg acg gac aat tcg acg aca   144
Tyr Phe Leu Leu Thr Asp Arg Phe Gly Arg Thr Asp Asn Ser Thr Thr
        35                  40                  45 gct aca tgc gat acg ggt gac caa atc tat tgt ggt ggc agt tgg caa   192
Ala Thr Cys Asp Thr Gly Asp Gln Ile Tyr Cys Gly Gly Ser Trp Gln
    50                  55                  60 gga atc atc aac cat ctg gat tat atc cag ggc atg gga ttc acg gcc   240
Gly Ile Ile Asn His Leu Asp Tyr Ile Gln Gly Met Gly Phe Thr Ala
65                  70                  75                  80 atc tgg atc tcg cct atc act gaa cag ctg ccc cag gat act gct gat   288
Ile Trp Ile Ser Pro Ile Thr Glu Gln Leu Pro Gln Asp Thr Ala Asp
                85                  90                  95 ggt gaa gct tac cat gga tat tgg cag cag aag ata tac gac gtg aac   336
Gly Glu Ala Tyr His Gly Tyr Trp Gln Gln Lys Ile Tyr Asp Val Asn
            100                 105                 110 tcc aac ttc ggc act gca gat gac ctc aag tcc ctc tca gat gcg ctt   384
Ser Asn Phe Gly Thr Ala Asp Asp Leu Lys Ser Leu Ser Asp Ala Leu
        115                 120                 125 cat gcc cgc gga atg tac ctc atg gtg gac gtc gtc cct aac cac atg   432
His Ala Arg Gly Met Tyr Leu Met Val Asp Val Val Pro Asn His Met
    130                 135                 140 ggc tac gcc ggc aac ggc aac gat gta gac tac agc gtc ttc gac ccc   480
Gly Tyr Ala Gly Asn Gly Asn Asp Val Asp Tyr Ser Val Phe Asp Pro
145                 150                 155                 160 ttc gat tcc tcc tcc tac ttc cac cca tac tgc ctg atc aca gat tgg   528
Phe Asp Ser Ser Ser Tyr Phe His Pro Tyr Cys Leu Ile Thr Asp Trp
                165                 170                 175
```

```
gac aac ttg acc atg gtc caa gat tgt tgg gag ggt gac acc atc gta      576
Asp Asn Leu Thr Met Val Gln Asp Cys Trp Glu Gly Asp Thr Ile Val
            180                 185                 190 tct ctg cca gac cta aac acc acc gaa act gcc gtg aga aca atc tgg      624
Ser Leu Pro Asp Leu Asn Thr Thr Glu Thr Ala Val Arg Thr Ile Trp
        195                 200                 205 tat gac tgg gta gcc gac ctg gta tcc aat tat tca gtc gac gga ctc      672
Tyr Asp Trp Val Ala Asp Leu Val Ser Asn Tyr Ser Val Asp Gly Leu
    210                 215                 220 cgc atc gac agt gtc ctc gaa gtc gaa cca gac ttc ttc ccg ggc tac      720
Arg Ile Asp Ser Val Leu Glu Val Glu Pro Asp Phe Phe Pro Gly Tyr
225                 230                 235                 240 cag gaa gca gca ggt gtc tac tgc gtc ggc gaa gtc gac aac ggc aac      768
Gln Glu Ala Ala Gly Val Tyr Cys Val Gly Glu Val Asp Asn Gly Asn
                245                 250                 255 cct gcc ctc gac tgc cca tac cag aag gtc ctg gac ggc gtc ctc aac      816
Pro Ala Leu Asp Cys Pro Tyr Gln Lys Val Leu Asp Gly Val Leu Asn
            260                 265                 270 tat ccg atc tac tgg caa ctc ctc tac gcc ttc gaa tcc tcc agc ggc      864
Tyr Pro Ile Tyr Trp Gln Leu Leu Tyr Ala Phe Glu Ser Ser Ser Gly
        275                 280                 285 agc atc agc aat ctc tac aac atg atc aaa tcc gtc gca agc gac tgc      912
Ser Ile Ser Asn Leu Tyr Asn Met Ile Lys Ser Val Ala Ser Asp Cys
    290                 295                 300 tcc gat ccg aca cta ctc ggc aac ttc atc gaa aac cac gac aat ccc      960
Ser Asp Pro Thr Leu Leu Gly Asn Phe Ile Glu Asn His Asp Asn Pro
305                 310                 315                 320 cgt ttc gcc tcc tac acc tcc gac tac tcg caa gcc aaa aac gtc ctc     1008
Arg Phe Ala Ser Tyr Thr Ser Asp Tyr Ser Gln Ala Lys Asn Val Leu
                325                 330                 335 agc tac atc ttc ctc tcc gac ggc atc ccc atc gtc tac gcc ggc gaa     1056
Ser Tyr Ile Phe Leu Ser Asp Gly Ile Pro Ile Val Tyr Ala Gly Glu
            340                 345                 350 gaa cag cac tac tcc ggc ggc aag gtg ccc tac aac cgc gaa gcg acc     1104
Glu Gln His Tyr Ser Gly Gly Lys Val Pro Tyr Asn Arg Glu Ala Thr
        355                 360                 365 tgg ctt tca ggc tac gac acc tcc gca gag ctg tac acc tgg ata gcc     1152
Trp Leu Ser Gly Tyr Asp Thr Ser Ala Glu Leu Tyr Thr Trp Ile Ala
    370                 375                 380 acc acg aac gcg atc cgc aaa cta gcc atc tca gct gac tcg gcc tac     1200
Thr Thr Asn Ala Ile Arg Lys Leu Ala Ile Ser Ala Asp Ser Ala Tyr
385                 390                 395                 400 att acc tac gcg aat gat gca ttc tac act gac agc aac acc atc gca     1248
Ile Thr Tyr Ala Asn Asp Ala Phe Tyr Thr Asp Ser Asn Thr Ile Ala
                405                 410                 415 atg cgc aaa ggc acc tca ggg agc agc caa gtc atc acc gtc ctc tcc aac 1296
Met Arg Lys Gly Thr Ser Gly Ser Gln Val Ile Thr Val Leu Ser Asn
            420                 425                 430 aaa ggc tcc tca gga agc agc tac acc ctg acc ctc agc gga agc ggc     1344
Lys Gly Ser Ser Gly Ser Ser Tyr Thr Leu Thr Leu Ser Gly Ser Gly
        435                 440                 445 tac aca tcc ggc acg aag ctg atc gaa gcg tac aca tgc aca tcc gtg     1392
Tyr Thr Ser Gly Thr Lys Leu Ile Glu Ala Tyr Thr Cys Thr Ser Val
    450                 455                 460 acc gtg gac tcg agc ggc gat att ccc gtg ccg atg gcg tcg gga tta     1440
Thr Val Asp Ser Ser Gly Asp Ile Pro Val Pro Met Ala Ser Gly Leu
465                 470                 475                 480 ccg aga gtt ctt ctg ccc gcg tcc gtc gtc gat agc tct tcg ctc tgt     1488
Pro Arg Val Leu Leu Pro Ala Ser Val Val Asp Ser Ser Ser Leu Cys
                485                 490                 495
```

```
ggc ggg agc gga aga aca acc acg acc aca act gct gct gct act agt      1536
Gly Gly Ser Gly Arg Thr Thr Thr Thr Thr Thr Ala Ala Ala Thr Ser
            500                 505                 510 aca tcc aaa gcc acc acc tcc tct tct tct tct gct gct gct act          1584
Thr Ser Lys Ala Thr Thr Ser Ser Ser Ser Ser Ala Ala Ala Thr
            515                 520                 525 act tct tca tca gtc gag gtc act ttc gac gtt tac gct acc aca gta      1632
Thr Ser Ser Ser Val Glu Val Thr Phe Asp Val Tyr Ala Thr Thr Val
            530                 535                 540 tat ggc cag aac atc tat atc acc ggt gat gtg agt gag ctc ggc aac      1680
Tyr Gly Gln Asn Ile Tyr Ile Thr Gly Asp Val Ser Glu Leu Gly Asn
545                 550                 555                 560 tgg aca ccc gcc aat ggt gtt gca ctc tct tct gct aac tac ccc acc      1728
Trp Thr Pro Ala Asn Gly Val Ala Leu Ser Ser Ala Asn Tyr Pro Thr
                565                 570                 575 tgg agt gcc acg atc gct ctc ccc gct gac acg aca atc cag tac aag      1776
Trp Ser Ala Thr Ile Ala Leu Pro Ala Asp Thr Thr Ile Gln Tyr Lys
                580                 585                 590 tat gtc aac att gac ggc agc acc gtc atc tgg gag gat gct atc agc      1824
Tyr Val Asn Ile Asp Gly Ser Thr Val Ile Trp Glu Asp Ala Ile Ser
                595                 600                 605 aat cgc gag atc acg acg ccc gcc agc ggc aca tac acc gaa aaa gac      1872
Asn Arg Glu Ile Thr Thr Pro Ala Ser Gly Thr Tyr Thr Glu Lys Asp
610                 615                 620 act tgg gat gaa tct tag                                              1890
Thr Trp Asp Glu Ser
625

<210> SEQ ID NO 34
<211> LENGTH: 629
<212> TYPE: PRT
<213> ORGANISM: Artificial sequence
<220> FEATURE:
<223> OTHER INFORMATION: Synthetic Construct

<400> SEQUENCE: 34

Met Arg Leu Ser Thr Ser Ser Leu Phe Leu Ser Val Ser Leu Leu Gly
1               5                   10                  15

Lys Leu Ala Leu Gly Leu Ser Ala Ala Glu Trp Arg Thr Gln Ser Ile
                20                  25                  30

Tyr Phe Leu Leu Thr Asp Arg Phe Gly Arg Thr Asp Asn Ser Thr Thr
            35                  40                  45

Ala Thr Cys Asp Thr Gly Asp Gln Ile Tyr Cys Gly Gly Ser Trp Gln
        50                  55                  60

Gly Ile Ile Asn His Leu Asp Tyr Ile Gln Gly Met Gly Phe Thr Ala
65                  70                  75                  80

Ile Trp Ile Ser Pro Ile Thr Glu Gln Leu Pro Gln Asp Thr Ala Asp
                85                  90                  95

Gly Glu Ala Tyr His Gly Tyr Trp Gln Gln Lys Ile Tyr Asp Val Asn
            100                 105                 110

Ser Asn Phe Gly Thr Ala Asp Asp Leu Lys Ser Leu Ser Asp Ala Leu
        115                 120                 125

His Ala Arg Gly Met Tyr Leu Met Val Asp Val Val Pro Asn His Met
    130                 135                 140

Gly Tyr Ala Gly Asn Gly Asn Asp Val Asp Tyr Ser Val Phe Asp Pro
145                 150                 155                 160

Phe Asp Ser Ser Ser Tyr Phe His Pro Tyr Cys Leu Ile Thr Asp Trp
                165                 170                 175
```

-continued

```
Asp Asn Leu Thr Met Val Gln Asp Cys Trp Glu Gly Asp Thr Ile Val
            180                 185                 190

Ser Leu Pro Asp Leu Asn Thr Thr Glu Thr Ala Val Arg Thr Ile Trp
        195                 200                 205

Tyr Asp Trp Val Ala Asp Leu Val Ser Asn Tyr Ser Val Asp Gly Leu
    210                 215                 220

Arg Ile Asp Ser Val Leu Glu Val Glu Pro Asp Phe Phe Pro Gly Tyr
225                 230                 235                 240

Gln Glu Ala Ala Gly Val Tyr Cys Val Gly Glu Val Asp Asn Gly Asn
                245                 250                 255

Pro Ala Leu Asp Cys Pro Tyr Gln Lys Val Leu Asp Gly Val Leu Asn
            260                 265                 270

Tyr Pro Ile Tyr Trp Gln Leu Leu Tyr Ala Phe Glu Ser Ser Ser Gly
        275                 280                 285

Ser Ile Ser Asn Leu Tyr Asn Met Ile Lys Ser Val Ala Ser Asp Cys
    290                 295                 300

Ser Asp Pro Thr Leu Leu Gly Asn Phe Ile Glu Asn His Asp Asn Pro
305                 310                 315                 320

Arg Phe Ala Ser Tyr Thr Ser Asp Tyr Ser Gln Ala Lys Asn Val Leu
                325                 330                 335

Ser Tyr Ile Phe Leu Ser Asp Gly Ile Pro Ile Val Tyr Ala Gly Glu
            340                 345                 350

Glu Gln His Tyr Ser Gly Gly Lys Val Pro Tyr Asn Arg Glu Ala Thr
        355                 360                 365

Trp Leu Ser Gly Tyr Asp Thr Ser Ala Glu Leu Tyr Thr Trp Ile Ala
    370                 375                 380

Thr Thr Asn Ala Ile Arg Lys Leu Ala Ile Ser Ala Asp Ser Ala Tyr
385                 390                 395                 400

Ile Thr Tyr Ala Asn Asp Ala Phe Tyr Thr Asp Ser Asn Thr Ile Ala
                405                 410                 415

Met Arg Lys Gly Thr Ser Gly Ser Gln Val Ile Thr Val Leu Ser Asn
            420                 425                 430

Lys Gly Ser Ser Gly Ser Ser Tyr Thr Leu Thr Leu Ser Gly Ser Gly
        435                 440                 445

Tyr Thr Ser Gly Thr Lys Leu Ile Glu Ala Tyr Thr Cys Thr Ser Val
    450                 455                 460

Thr Val Asp Ser Ser Gly Asp Ile Pro Val Pro Met Ala Ser Gly Leu
465                 470                 475                 480

Pro Arg Val Leu Leu Pro Ala Ser Val Val Asp Ser Ser Ser Leu Cys
                485                 490                 495

Gly Gly Ser Gly Arg Thr Thr Thr Thr Thr Ala Ala Ala Thr Ser
            500                 505                 510

Thr Ser Lys Ala Thr Thr Ser Ser Ser Ser Ser Ala Ala Ala Thr
        515                 520                 525

Thr Ser Ser Ser Val Glu Val Thr Phe Asp Val Tyr Ala Thr Thr Val
    530                 535                 540

Tyr Gly Gln Asn Ile Tyr Ile Thr Gly Asp Val Ser Glu Leu Gly Asn
545                 550                 555                 560

Trp Thr Pro Ala Asn Gly Val Ala Leu Ser Ala Asn Tyr Pro Thr
                565                 570                 575

Trp Ser Ala Thr Ile Ala Leu Pro Ala Asp Thr Thr Ile Gln Tyr Lys
            580                 585                 590

Tyr Val Asn Ile Asp Gly Ser Thr Val Ile Trp Glu Asp Ala Ile Ser
        595                 600                 605
```

```
Asn Arg Glu Ile Thr Thr Pro Ala Ser Gly Thr Tyr Thr Glu Lys Asp
    610                 615                 620

Thr Trp Asp Glu Ser
625

<210> SEQ ID NO 35
<211> LENGTH: 1923
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(1923)

<400> SEQUENCE: 35 atg gtc gcg tgg tgg tct cta ttt ctg tac ggc ctt cag gtc gcg gca        48
Met Val Ala Trp Trp Ser Leu Phe Leu Tyr Gly Leu Gln Val Ala Ala
1               5                   10                  15 cct gct ttg gct gca acg cct gcg gac tgg cga tcg caa tcc att tat        96
Pro Ala Leu Ala Ala Thr Pro Ala Asp Trp Arg Ser Gln Ser Ile Tyr
            20                  25                  30 ttc ctt ctc acg gat cga ttt gca agg acg gat ggg tcg acg act gcg       144
Phe Leu Leu Thr Asp Arg Phe Ala Arg Thr Asp Gly Ser Thr Thr Ala
        35                  40                  45 act tgt aat act gcg gat cag aaa tac tgt ggt gga aca tgg cag ggc       192
Thr Cys Asn Thr Ala Asp Gln Lys Tyr Cys Gly Gly Thr Trp Gln Gly
    50                  55                  60 atc atc gac aag ttg gac tat atc cag gga atg ggc ttc aca gcc atc       240
Ile Ile Asp Lys Leu Asp Tyr Ile Gln Gly Met Gly Phe Thr Ala Ile
65                  70                  75                  80 tgg atc acc ccc gtt aca gcc cag ctg ccc cag acc acc gca tat gga       288
Trp Ile Thr Pro Val Thr Ala Gln Leu Pro Gln Thr Thr Ala Tyr Gly
                85                  90                  95 gat gcc tac cat ggc tac tgg cag cag gat ata tac tct ctg aac gaa       336
Asp Ala Tyr His Gly Tyr Trp Gln Gln Asp Ile Tyr Ser Leu Asn Glu
            100                 105                 110 aac tac ggc act gca gat gac ttg aag gcg ctc tct tcg gcc ctt cat       384
Asn Tyr Gly Thr Ala Asp Asp Leu Lys Ala Leu Ser Ser Ala Leu His
        115                 120                 125 gag agg ggg atg tat ctt atg gtc gat gtg gtt gct aac cat atg ggc       432
Glu Arg Gly Met Tyr Leu Met Val Asp Val Val Ala Asn His Met Gly
    130                 135                 140 tat gat gga gcg ggt agc tca gtc gat tac agt gtg ttt aaa ccg ttc       480
Tyr Asp Gly Ala Gly Ser Ser Val Asp Tyr Ser Val Phe Lys Pro Phe
145                 150                 155                 160 agt tcc caa gac tac ttc cac ccg ttc tgt ttc att caa aac tat gaa       528
Ser Ser Gln Asp Tyr Phe His Pro Phe Cys Phe Ile Gln Asn Tyr Glu
                165                 170                 175 gat cag act cag gtt gag gat tgc tgg cta gga gat aac act gtc tcc       576
Asp Gln Thr Gln Val Glu Asp Cys Trp Leu Gly Asp Asn Thr Val Ser
            180                 185                 190 ttg cct gat ctc gat acc acc aag gat gtg gtc aag aat gaa tgg tac       624
Leu Pro Asp Leu Asp Thr Thr Lys Asp Val Val Lys Asn Glu Trp Tyr
        195                 200                 205 gac tgg gtg gga tca ttg gta tcg aac tac tcc att gac ggc ctc cgt       672
Asp Trp Val Gly Ser Leu Val Ser Asn Tyr Ser Ile Asp Gly Leu Arg
    210                 215                 220 atc gac aca gta aaa cac gtc cag aag gac ttc tgg ccc ggg tac aac       720
Ile Asp Thr Val Lys His Val Gln Lys Asp Phe Trp Pro Gly Tyr Asn
225                 230                 235                 240
```

```
aaa gcc gca ggc gtg tac tgt atc ggc gag gtg ctc gac ggt gat ccg      768
Lys Ala Ala Gly Val Tyr Cys Ile Gly Glu Val Leu Asp Gly Asp Pro
                245                 250                 255 gcc tac act tgt ccc tac cag aac gtc atg gac ggt gta ctg aac tat      816
Ala Tyr Thr Cys Pro Tyr Gln Asn Val Met Asp Gly Val Leu Asn Tyr
            260                 265                 270 ccc att tac tat cca ctc ctc aac gcc ttc aag tca acc tcc ggc agc      864
Pro Ile Tyr Tyr Pro Leu Leu Asn Ala Phe Lys Ser Thr Ser Gly Ser
        275                 280                 285 atg gac gac ctc tac aac atg atc aac acc gtc aaa tcc gac tgt cca      912
Met Asp Asp Leu Tyr Asn Met Ile Asn Thr Val Lys Ser Asp Cys Pro
    290                 295                 300 gac tca aca ctc ctg ggc aca ttc gtc gag aac cac gac aac cca cgg      960
Asp Ser Thr Leu Leu Gly Thr Phe Val Glu Asn His Asp Asn Pro Arg
305                 310                 315                 320 ttc gct tct tac acc aac gac ata gcc ctc gcc aag aac gtc gca gca     1008
Phe Ala Ser Tyr Thr Asn Asp Ile Ala Leu Ala Lys Asn Val Ala Ala
                325                 330                 335 ttc atc atc ctc aac gac gga atc ccc atc atc tac gcc ggc caa gaa     1056
Phe Ile Ile Leu Asn Asp Gly Ile Pro Ile Ile Tyr Ala Gly Gln Glu
            340                 345                 350 cag cac tac gcc ggc gga aac gac ccc gcg aac cgc gaa gca acc tgg     1104
Gln His Tyr Ala Gly Gly Asn Asp Pro Ala Asn Arg Glu Ala Thr Trp
        355                 360                 365 ctc tcg ggc tac ccg acc gac agc gag ctg tac aag tta att gcc tcc     1152
Leu Ser Gly Tyr Pro Thr Asp Ser Glu Leu Tyr Lys Leu Ile Ala Ser
    370                 375                 380 gcg aac gca atc cgg aac tat gcc att agc aaa gat aca gga ttc gtg     1200
Ala Asn Ala Ile Arg Asn Tyr Ala Ile Ser Lys Asp Thr Gly Phe Val
385                 390                 395                 400 acc tac aag aac tgg ccc atc tac aaa gac gac aca acg atc gcc atg     1248
Thr Tyr Lys Asn Trp Pro Ile Tyr Lys Asp Asp Thr Thr Ile Ala Met
                405                 410                 415 cgc aag ggc aca gat ggg tcg cag atc gtg act atc ttg tcc aac aag     1296
Arg Lys Gly Thr Asp Gly Ser Gln Ile Val Thr Ile Leu Ser Asn Lys
            420                 425                 430 ggt gct tcg ggt gat tcg tat acc ctc tcc ttg agt ggt gcg ggt tac     1344
Gly Ala Ser Gly Asp Ser Tyr Thr Leu Ser Leu Ser Gly Ala Gly Tyr
        435                 440                 445 aca gcc ggc cag caa ttg acg gag gtc att ggc tgc acg acc gtg acg     1392
Thr Ala Gly Gln Gln Leu Thr Glu Val Ile Gly Cys Thr Thr Val Thr
    450                 455                 460 gtt ggt tcg gat gga aat gtg cct gtt cct atg gca ggt ggg cta cct     1440
Val Gly Ser Asp Gly Asn Val Pro Val Pro Met Ala Gly Gly Leu Pro
465                 470                 475                 480 agg gta ttg tat ccg act gag aag ttg gca ggt agc aag atc tgt agt     1488
Arg Val Leu Tyr Pro Thr Glu Lys Leu Ala Gly Ser Lys Ile Cys Ser
                485                 490                 495 agc tcg gga aga aca acc acg aca act gct gct gct act agt aca        1536
Ser Ser Gly Arg Thr Thr Thr Thr Thr Ala Ala Ala Thr Ser Thr
            500                 505                 510 tcc aaa gcc acc acc tcc tct tct tct tct gct gct gct act act        1584
Ser Lys Ala Thr Thr Ser Ser Ser Ser Ser Ala Ala Ala Thr Thr
        515                 520                 525 tct tca tca tgc acc gca aca agc acc acc ctc ccc atc acc ttc gaa    1632
Ser Ser Ser Cys Thr Ala Thr Ser Thr Thr Leu Pro Ile Thr Phe Glu
    530                 535                 540 gaa ctc gtc acc act acc tac ggg gaa gaa gtc tac ctc agc gga tct    1680
Glu Leu Val Thr Thr Thr Tyr Gly Glu Glu Val Tyr Leu Ser Gly Ser
545                 550                 555                 560
```

```
atc tcc cag ctc gga gag tgg gat acg agt gac gcg gtg aag ttg tcc    1728
Ile Ser Gln Leu Gly Glu Trp Asp Thr Ser Asp Ala Val Lys Leu Ser
            565                 570                 575 gcg gat gat tat acc tcg agt aac ccc gag tgg tct gtt act gtg tcg    1776
Ala Asp Asp Tyr Thr Ser Ser Asn Pro Glu Trp Ser Val Thr Val Ser
        580                 585                 590 ttg ccg gtg ggg acg acc ttc gag tat aag ttt att aag gtc gat gag    1824
Leu Pro Val Gly Thr Thr Phe Glu Tyr Lys Phe Ile Lys Val Asp Glu
            595                 600                 605 ggt gga agt gtg act tgg gaa agt gat ccg aat agg gag tat act gtg    1872
Gly Gly Ser Val Thr Trp Glu Ser Asp Pro Asn Arg Glu Tyr Thr Val
610                 615                 620 cct gaa tgt ggg aat ggg agt ggg gag acg gtg gtt gat acg tgg agg    1920
Pro Glu Cys Gly Asn Gly Ser Gly Glu Thr Val Val Asp Thr Trp Arg
625                 630                 635                 640 tag                                                                  1923
```

<210> SEQ ID NO 36
<211> LENGTH: 640
<212> TYPE: PRT
<213> ORGANISM: Artificial sequence
<220> FEATURE:
<223> OTHER INFORMATION: Synthetic Construct

<400> SEQUENCE: 36

```
Met Val Ala Trp Trp Ser Leu Phe Leu Tyr Gly Leu Gln Val Ala Ala
1               5                   10                  15

Pro Ala Leu Ala Ala Thr Pro Ala Asp Trp Arg Ser Gln Ser Ile Tyr
            20                  25                  30

Phe Leu Leu Thr Asp Arg Phe Ala Arg Thr Asp Gly Ser Thr Thr Ala
        35                  40                  45

Thr Cys Asn Thr Ala Asp Gln Lys Tyr Cys Gly Gly Thr Trp Gln Gly
    50                  55                  60

Ile Ile Asp Lys Leu Asp Tyr Ile Gln Gly Met Gly Phe Thr Ala Ile
65                  70                  75                  80

Trp Ile Thr Pro Val Thr Ala Gln Leu Pro Gln Thr Thr Ala Tyr Gly
                85                  90                  95

Asp Ala Tyr His Gly Tyr Trp Gln Gln Asp Ile Tyr Ser Leu Asn Glu
            100                 105                 110

Asn Tyr Gly Thr Ala Asp Asp Leu Lys Ala Leu Ser Ser Ala Leu His
        115                 120                 125

Glu Arg Gly Met Tyr Leu Met Val Asp Val Val Ala Asn His Met Gly
    130                 135                 140

Tyr Asp Gly Ala Gly Ser Ser Val Asp Tyr Ser Val Phe Lys Pro Phe
145                 150                 155                 160

Ser Ser Gln Asp Tyr Phe His Pro Phe Cys Phe Ile Gln Asn Tyr Glu
                165                 170                 175

Asp Gln Thr Gln Val Glu Asp Cys Trp Leu Gly Asp Asn Thr Val Ser
            180                 185                 190

Leu Pro Asp Leu Asp Thr Thr Lys Asp Val Val Lys Asn Glu Trp Tyr
        195                 200                 205

Asp Trp Val Gly Ser Leu Val Ser Asn Tyr Ser Ile Asp Gly Leu Arg
    210                 215                 220

Ile Asp Thr Val Lys His Val Gln Lys Asp Phe Trp Pro Gly Tyr Asn
225                 230                 235                 240

Lys Ala Ala Gly Val Tyr Cys Ile Gly Glu Val Leu Asp Gly Asp Pro
                245                 250                 255
```

Ala Tyr Thr Cys Pro Tyr Gln Asn Val Met Asp Gly Val Leu Asn Tyr
                260                 265                 270

Pro Ile Tyr Tyr Pro Leu Leu Asn Ala Phe Lys Ser Thr Ser Gly Ser
            275                 280                 285

Met Asp Asp Leu Tyr Asn Met Ile Asn Thr Val Lys Ser Asp Cys Pro
290                 295                 300

Asp Ser Thr Leu Leu Gly Thr Phe Val Glu Asn His Asp Asn Pro Arg
305                 310                 315                 320

Phe Ala Ser Tyr Thr Asn Asp Ile Ala Leu Ala Lys Asn Val Ala Ala
                325                 330                 335

Phe Ile Ile Leu Asn Asp Gly Ile Pro Ile Ile Tyr Ala Gly Gln Glu
            340                 345                 350

Gln His Tyr Ala Gly Gly Asn Asp Pro Ala Asn Arg Glu Ala Thr Trp
        355                 360                 365

Leu Ser Gly Tyr Pro Thr Asp Ser Glu Leu Tyr Lys Leu Ile Ala Ser
    370                 375                 380

Ala Asn Ala Ile Arg Asn Tyr Ala Ile Ser Lys Asp Thr Gly Phe Val
385                 390                 395                 400

Thr Tyr Lys Asn Trp Pro Ile Tyr Lys Asp Asp Thr Thr Ile Ala Met
                405                 410                 415

Arg Lys Gly Thr Asp Gly Ser Gln Ile Val Thr Ile Leu Ser Asn Lys
            420                 425                 430

Gly Ala Ser Gly Asp Ser Tyr Thr Leu Ser Leu Ser Gly Ala Gly Tyr
        435                 440                 445

Thr Ala Gly Gln Gln Leu Thr Glu Val Ile Gly Cys Thr Thr Val Thr
    450                 455                 460

Val Gly Ser Asp Gly Asn Val Pro Val Pro Met Ala Gly Gly Leu Pro
465                 470                 475                 480

Arg Val Leu Tyr Pro Thr Glu Lys Leu Ala Gly Ser Lys Ile Cys Ser
                485                 490                 495

Ser Ser Gly Arg Thr Thr Thr Thr Thr Ala Ala Ala Thr Ser Thr
            500                 505                 510

Ser Lys Ala Thr Thr Ser Ser Ser Ser Ser Ala Ala Ala Thr Thr
        515                 520                 525

Ser Ser Ser Cys Thr Ala Thr Ser Thr Thr Leu Pro Ile Thr Phe Glu
    530                 535                 540

Glu Leu Val Thr Thr Thr Tyr Gly Glu Glu Val Tyr Leu Ser Gly Ser
545                 550                 555                 560

Ile Ser Gln Leu Gly Glu Trp Asp Thr Ser Asp Ala Val Lys Leu Ser
                565                 570                 575

Ala Asp Asp Tyr Thr Ser Ser Asn Pro Glu Trp Ser Val Thr Val Ser
            580                 585                 590

Leu Pro Val Gly Thr Thr Phe Glu Tyr Lys Phe Ile Lys Val Asp Glu
        595                 600                 605

Gly Gly Ser Val Thr Trp Glu Ser Asp Pro Asn Arg Glu Tyr Thr Val
    610                 615                 620

Pro Glu Cys Gly Asn Gly Ser Gly Glu Thr Val Val Asp Thr Trp Arg
625                 630                 635                 640

<210> SEQ ID NO 37
<211> LENGTH: 1830
<212> TYPE: DNA
<213> ORGANISM: Artificial sequence
<220> FEATURE:
<223> OTHER INFORMATION: Synthetic construct
<220> FEATURE:

```
<221> NAME/KEY: CDS
<222> LOCATION: (1)..(1830)

<400> SEQUENCE: 37 atg aga tta tcg act tcg agt ctc ttc ctt tcc gtg tct ctg ctg ggg     48
Met Arg Leu Ser Thr Ser Ser Leu Phe Leu Ser Val Ser Leu Leu Gly
1               5                   10                  15 aag ctg gcc ctc ggg ctg tcg gct gca gaa tgg cgc act cag tcg att     96
Lys Leu Ala Leu Gly Leu Ser Ala Ala Glu Trp Arg Thr Gln Ser Ile
            20                  25                  30 tac ttc cta ttg acg gat cgg ttc ggt agg acg gac aat tcg acg aca    144
Tyr Phe Leu Leu Thr Asp Arg Phe Gly Arg Thr Asp Asn Ser Thr Thr
        35                  40                  45 gct aca tgc gat acg ggt gac caa atc tat tgt ggt ggc agt tgg caa    192
Ala Thr Cys Asp Thr Gly Asp Gln Ile Tyr Cys Gly Gly Ser Trp Gln
    50                  55                  60 gga atc atc aac cat ctg gat tat atc cag ggc atg gga ttc acg gcc    240
Gly Ile Ile Asn His Leu Asp Tyr Ile Gln Gly Met Gly Phe Thr Ala
65                  70                  75                  80 atc tgg atc tcg cct atc act gaa cag ctg ccc cag gat act gct gat    288
Ile Trp Ile Ser Pro Ile Thr Glu Gln Leu Pro Gln Asp Thr Ala Asp
                85                  90                  95 ggt gaa gct tac cat gga tat tgg cag cag aag ata tac gac gtg aac    336
Gly Glu Ala Tyr His Gly Tyr Trp Gln Gln Lys Ile Tyr Asp Val Asn
            100                 105                 110 tcc aac ttc ggc act gca gat gac ctc aag tcc ctc tca gat gcg ctt    384
Ser Asn Phe Gly Thr Ala Asp Asp Leu Lys Ser Leu Ser Asp Ala Leu
        115                 120                 125 cat gcc cgc gga atg tac ctc atg gtg gac gtc gtc cct aac cac atg    432
His Ala Arg Gly Met Tyr Leu Met Val Asp Val Val Pro Asn His Met
    130                 135                 140 ggc tac gcc ggc aac ggc aac gat gta gac tac agc gtc ttc gac ccc    480
Gly Tyr Ala Gly Asn Gly Asn Asp Val Asp Tyr Ser Val Phe Asp Pro
145                 150                 155                 160 ttc gat tcc tcc tcc tac ttc cac cca tac tgc ctg atc aca gat tgg    528
Phe Asp Ser Ser Ser Tyr Phe His Pro Tyr Cys Leu Ile Thr Asp Trp
                165                 170                 175 gac aac ttg acc atg gtc caa gat tgt tgg gag ggt gac acc atc gta    576
Asp Asn Leu Thr Met Val Gln Asp Cys Trp Glu Gly Asp Thr Ile Val
            180                 185                 190 tct ctg cca gac cta aac acc acc gaa act gcc gtg aga aca atc tgg    624
Ser Leu Pro Asp Leu Asn Thr Thr Glu Thr Ala Val Arg Thr Ile Trp
        195                 200                 205 tat gac tgg gta gcc gac ctg gta tcc aat tat tca gtc gac gga ctc    672
Tyr Asp Trp Val Ala Asp Leu Val Ser Asn Tyr Ser Val Asp Gly Leu
    210                 215                 220 cgc atc gac agt gtc ctc gaa gtc gaa cca gac ttc ttc ccg ggc tac    720
Arg Ile Asp Ser Val Leu Glu Val Glu Pro Asp Phe Phe Pro Gly Tyr
225                 230                 235                 240 cag gaa gca gca ggt gtc tac tgc gtc ggc gaa gtc gac aac ggc aac    768
Gln Glu Ala Ala Gly Val Tyr Cys Val Gly Glu Val Asp Asn Gly Asn
                245                 250                 255 cct gcc ctc gac tgc cca tac cag aag gtc ctg gac ggc gtc ctc aac    816
Pro Ala Leu Asp Cys Pro Tyr Gln Lys Val Leu Asp Gly Val Leu Asn
            260                 265                 270 tat ccg atc tac tgg caa ctc ctc tac gcc ttc gaa tcc tcc agc ggc    864
Tyr Pro Ile Tyr Trp Gln Leu Leu Tyr Ala Phe Glu Ser Ser Ser Gly
        275                 280                 285 agc atc agc aat ctc tac aac atg atc aaa tcc gtc gca agc gac tgc    912
Ser Ile Ser Asn Leu Tyr Asn Met Ile Lys Ser Val Ala Ser Asp Cys
    290                 295                 300
```

```
tcc gat ccg aca cta ctc ggc aac ttc atc gaa aac cac gac aat ccc      960
Ser Asp Pro Thr Leu Leu Gly Asn Phe Ile Glu Asn His Asp Asn Pro
305                 310                 315                 320 cgt ttc gcc tcc tac acc tcc gac tac tcg caa gcc aaa aac gtc ctc     1008
Arg Phe Ala Ser Tyr Thr Ser Asp Tyr Ser Gln Ala Lys Asn Val Leu
                325                 330                 335 agc tac atc ttc ctc tcc gac ggc atc ccc atc gtc tac gcc ggc gaa     1056
Ser Tyr Ile Phe Leu Ser Asp Gly Ile Pro Ile Val Tyr Ala Gly Glu
            340                 345                 350 gaa cag cac tac tcc ggc ggc aag gtg ccc tac aac cgc gaa gcg acc     1104
Glu Gln His Tyr Ser Gly Gly Lys Val Pro Tyr Asn Arg Glu Ala Thr
        355                 360                 365 tgg ctt tca ggc tac gac acc tcc gca gag ctg tac acc tgg ata gcc     1152
Trp Leu Ser Gly Tyr Asp Thr Ser Ala Glu Leu Tyr Thr Trp Ile Ala
370                 375                 380 acc acg aac gcg atc cgc aaa cta gcc atc tca gct gac tcg gcc tac     1200
Thr Thr Asn Ala Ile Arg Lys Leu Ala Ile Ser Ala Asp Ser Ala Tyr
385                 390                 395                 400 att acc tac gcg aat gat gca ttc tac act gac agc aac acc atc gca     1248
Ile Thr Tyr Ala Asn Asp Ala Phe Tyr Thr Asp Ser Asn Thr Ile Ala
                405                 410                 415 atg cgc aaa ggc acc tca ggg agc caa gtc atc acc gtc ctc tcc aac     1296
Met Arg Lys Gly Thr Ser Gly Ser Gln Val Ile Thr Val Leu Ser Asn
            420                 425                 430 aaa ggc tcc tca gga agc agc tac acc ctg acc ctc agc gga agc ggc     1344
Lys Gly Ser Ser Gly Ser Ser Tyr Thr Leu Thr Leu Ser Gly Ser Gly
        435                 440                 445 tac aca tcc ggc acg aag ctg atc gaa gcg tac aca tgc aca tcc gtg     1392
Tyr Thr Ser Gly Thr Lys Leu Ile Glu Ala Tyr Thr Cys Thr Ser Val
450                 455                 460 acc gtg gac tcg agc ggc gat att ccc gtg ccg atg gcg tcg gga tta     1440
Thr Val Asp Ser Ser Gly Asp Ile Pro Val Pro Met Ala Ser Gly Leu
465                 470                 475                 480 ccg aga gtt ctt ctg ccc gcg tcc gtc gtc gat agc tct tcg ctc tgt     1488
Pro Arg Val Leu Leu Pro Ala Ser Val Val Asp Ser Ser Ser Leu Cys
                485                 490                 495 ggc ggg agc gga aga ggt gct aca agc ccg ggt ggc tcc tcg ggt agt     1536
Gly Gly Ser Gly Arg Gly Ala Thr Ser Pro Gly Gly Ser Ser Gly Ser
            500                 505                 510 gtc gag gtc act ttc gac gtt tac gct acc aca gta tat ggc cag aac     1584
Val Glu Val Thr Phe Asp Val Tyr Ala Thr Thr Val Tyr Gly Gln Asn
        515                 520                 525 atc tat atc acc ggt gat gtg agt gag ctc ggc aac tgg aca ccc gcc     1632
Ile Tyr Ile Thr Gly Asp Val Ser Glu Leu Gly Asn Trp Thr Pro Ala
530                 535                 540 aat ggt gtt gca ctc tct tct gct aac tac ccc acc tgg agt gcc acg     1680
Asn Gly Val Ala Leu Ser Ser Ala Asn Tyr Pro Thr Trp Ser Ala Thr
545                 550                 555                 560 atc gct ctc ccc gct gac acg aca atc cag tac aag tat gtc aac att     1728
Ile Ala Leu Pro Ala Asp Thr Thr Ile Gln Tyr Lys Tyr Val Asn Ile
                565                 570                 575 gac ggc agc acc gtc atc tgg gag gat gct atc agc aat cgc gag atc     1776
Asp Gly Ser Thr Val Ile Trp Glu Asp Ala Ile Ser Asn Arg Glu Ile
            580                 585                 590 acg acg ccc gcc agc ggc aca tac acc gaa aaa gac act tgg gat gaa     1824
Thr Thr Pro Ala Ser Gly Thr Tyr Thr Glu Lys Asp Thr Trp Asp Glu
        595                 600                 605 tct tag                                                              1830
Ser
```

-continued

```
<210> SEQ ID NO 38
<211> LENGTH: 609
<212> TYPE: PRT
<213> ORGANISM: Artificial sequence
<220> FEATURE:
<223> OTHER INFORMATION: Synthetic Construct

<400> SEQUENCE: 38
```

Met Arg Leu Ser Thr Ser Ser Leu Phe Leu Ser Val Ser Leu Leu Gly
1               5                   10                  15

Lys Leu Ala Leu Gly Leu Ser Ala Ala Glu Trp Arg Thr Gln Ser Ile
            20                  25                  30

Tyr Phe Leu Leu Thr Asp Arg Phe Gly Arg Thr Asp Asn Ser Thr Thr
        35                  40                  45

Ala Thr Cys Asp Thr Gly Asp Gln Ile Tyr Cys Gly Gly Ser Trp Gln
    50                  55                  60

Gly Ile Ile Asn His Leu Asp Tyr Ile Gln Gly Met Gly Phe Thr Ala
65                  70                  75                  80

Ile Trp Ile Ser Pro Ile Thr Glu Gln Leu Pro Gln Asp Thr Ala Asp
                85                  90                  95

Gly Glu Ala Tyr His Gly Tyr Trp Gln Gln Lys Ile Tyr Asp Val Asn
            100                 105                 110

Ser Asn Phe Gly Thr Ala Asp Asp Leu Lys Ser Leu Ser Asp Ala Leu
        115                 120                 125

His Ala Arg Gly Met Tyr Leu Met Val Asp Val Val Pro Asn His Met
    130                 135                 140

Gly Tyr Ala Gly Asn Gly Asn Asp Val Asp Tyr Ser Val Phe Asp Pro
145                 150                 155                 160

Phe Asp Ser Ser Tyr Phe His Pro Tyr Cys Leu Ile Thr Asp Trp
                165                 170                 175

Asp Asn Leu Thr Met Val Gln Asp Cys Trp Glu Gly Asp Thr Ile Val
            180                 185                 190

Ser Leu Pro Asp Leu Asn Thr Thr Glu Thr Ala Val Arg Thr Ile Trp
        195                 200                 205

Tyr Asp Trp Val Ala Asp Leu Val Ser Asn Tyr Ser Val Asp Gly Leu
    210                 215                 220

Arg Ile Asp Ser Val Leu Glu Val Glu Pro Asp Phe Phe Pro Gly Tyr
225                 230                 235                 240

Gln Glu Ala Ala Gly Val Tyr Cys Val Gly Glu Val Asp Asn Gly Asn
                245                 250                 255

Pro Ala Leu Asp Cys Pro Tyr Gln Lys Val Leu Asp Gly Val Leu Asn
            260                 265                 270

Tyr Pro Ile Tyr Trp Gln Leu Leu Tyr Ala Phe Glu Ser Ser Ser Gly
        275                 280                 285

Ser Ile Ser Asn Leu Tyr Asn Met Ile Lys Ser Val Ala Ser Asp Cys
    290                 295                 300

Ser Asp Pro Thr Leu Leu Gly Asn Phe Ile Glu Asn His Asp Asn Pro
305                 310                 315                 320

Arg Phe Ala Ser Tyr Thr Ser Asp Tyr Ser Gln Ala Lys Asn Val Leu
                325                 330                 335

Ser Tyr Ile Phe Leu Ser Asp Gly Ile Pro Ile Val Tyr Ala Gly Glu
            340                 345                 350

Glu Gln His Tyr Ser Gly Gly Lys Val Pro Tyr Asn Arg Glu Ala Thr
        355                 360                 365

Trp Leu Ser Gly Tyr Asp Thr Ser Ala Glu Leu Tyr Thr Trp Ile Ala

```
                    370                 375                 380
Thr Thr Asn Ala Ile Arg Lys Leu Ala Ile Ser Ala Asp Ser Ala Tyr
385                 390                 395                 400

Ile Thr Tyr Ala Asn Asp Ala Phe Tyr Thr Asp Ser Asn Thr Ile Ala
                405                 410                 415

Met Arg Lys Gly Thr Ser Gly Ser Gln Val Ile Thr Val Leu Ser Asn
            420                 425                 430

Lys Gly Ser Ser Gly Ser Ser Tyr Thr Leu Thr Leu Ser Gly Ser Gly
        435                 440                 445

Tyr Thr Ser Gly Thr Lys Leu Ile Glu Ala Tyr Thr Cys Thr Ser Val
    450                 455                 460

Thr Val Asp Ser Ser Gly Asp Ile Pro Val Pro Met Ala Ser Gly Leu
465                 470                 475                 480

Pro Arg Val Leu Leu Pro Ala Ser Val Val Asp Ser Ser Ser Leu Cys
                485                 490                 495

Gly Gly Ser Gly Arg Gly Ala Thr Ser Pro Gly Gly Ser Ser Gly Ser
            500                 505                 510

Val Glu Val Thr Phe Asp Val Tyr Ala Thr Thr Val Tyr Gly Gln Asn
        515                 520                 525

Ile Tyr Ile Thr Gly Asp Val Ser Glu Leu Gly Asn Trp Thr Pro Ala
    530                 535                 540

Asn Gly Val Ala Leu Ser Ser Ala Asn Tyr Pro Thr Trp Ser Ala Thr
545                 550                 555                 560

Ile Ala Leu Pro Ala Asp Thr Thr Ile Gln Tyr Lys Tyr Val Asn Ile
                565                 570                 575

Asp Gly Ser Thr Val Ile Trp Glu Asp Ala Ile Ser Asn Arg Glu Ile
            580                 585                 590

Thr Thr Pro Ala Ser Gly Thr Tyr Thr Glu Lys Asp Thr Trp Asp Glu
        595                 600                 605

Ser
```

<210> SEQ ID NO 39
<211> LENGTH: 1827
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(1827)

<400> SEQUENCE: 39

```
atg gtc gcg tgg tgg tct cta ttt ctg tac ggc ctt cag gtc gcg gca    48
Met Val Ala Trp Trp Ser Leu Phe Leu Tyr Gly Leu Gln Val Ala Ala
1               5                   10                  15 cct gct ttg gct gca acg cct gcg gac tgg cga tcg caa tcc att tat    96
Pro Ala Leu Ala Ala Thr Pro Ala Asp Trp Arg Ser Gln Ser Ile Tyr
            20                  25                  30 ttc ctc ctc acg gat cga ttt gca agg acg gat ggg tcg acg act gcg   144
Phe Leu Leu Thr Asp Arg Phe Ala Arg Thr Asp Gly Ser Thr Thr Ala
        35                  40                  45 act tgt aat act gcg gat cag aaa tac tgt ggt gga aca tgg cag ggc   192
Thr Cys Asn Thr Ala Asp Gln Lys Tyr Cys Gly Gly Thr Trp Gln Gly
    50                  55                  60 atc atc gac aag ttg gac tat atc cag gga atg ggc ttc aca gcc atc   240
Ile Ile Asp Lys Leu Asp Tyr Ile Gln Gly Met Gly Phe Thr Ala Ile
65                  70                  75                  80 tgg atc acc ccc gtt aca gcc cag ctg ccc cag acc acc gca tat gga   288
Trp Ile Thr Pro Val Thr Ala Gln Leu Pro Gln Thr Thr Ala Tyr Gly
```

```
Trp Ile Thr Pro Val Thr Ala Gln Leu Pro Gln Thr Thr Ala Tyr Gly
                85                  90                  95 gat gcc tac cat ggc tac tgg cag cag gat ata tac tct ctg aac gaa    336
Asp Ala Tyr His Gly Tyr Trp Gln Gln Asp Ile Tyr Ser Leu Asn Glu
            100                 105                 110 aac tac ggc act gca gat gac ttg aag gcg ctc tct tcg gcc ctt cat    384
Asn Tyr Gly Thr Ala Asp Asp Leu Lys Ala Leu Ser Ser Ala Leu His
        115                 120                 125 gag agg ggg atg tat ctt atg gtc gat gtg gtt gct aac cat atg ggc    432
Glu Arg Gly Met Tyr Leu Met Val Asp Val Val Ala Asn His Met Gly
    130                 135                 140 tat gat gga gcg ggt agc tca gtc gat tac agt gtg ttt aaa ccg ttc    480
Tyr Asp Gly Ala Gly Ser Ser Val Asp Tyr Ser Val Phe Lys Pro Phe
145                 150                 155                 160 agt tcc caa gac tac ttc cac ccg ttc tgt ttc att caa aac tat gaa    528
Ser Ser Gln Asp Tyr Phe His Pro Phe Cys Phe Ile Gln Asn Tyr Glu
                165                 170                 175 gat cag act cag gtt gag gat tgc tgg cta gga gat aac act gtc tcc    576
Asp Gln Thr Gln Val Glu Asp Cys Trp Leu Gly Asp Asn Thr Val Ser
            180                 185                 190 ttg cct gat ctc gat acc acc aag gat gtg gtc aag aat gaa tgg tac    624
Leu Pro Asp Leu Asp Thr Thr Lys Asp Val Val Lys Asn Glu Trp Tyr
        195                 200                 205 gac tgg gtg gga tca ttg gta tcg aac tac tcc att gac ggc ctc cgt    672
Asp Trp Val Gly Ser Leu Val Ser Asn Tyr Ser Ile Asp Gly Leu Arg
    210                 215                 220 atc gac aca gta aaa cac gtc cag aag gac ttc tgg ccc ggg tac aac    720
Ile Asp Thr Val Lys His Val Gln Lys Asp Phe Trp Pro Gly Tyr Asn
225                 230                 235                 240 aaa gcc gca ggc gtg tac tgt atc ggc gag gtg ctc gac ggt gat ccg    768
Lys Ala Ala Gly Val Tyr Cys Ile Gly Glu Val Leu Asp Gly Asp Pro
                245                 250                 255 gcc tac act tgt ccc tac cag aac gtc atg gac ggc gta ctg aac tat    816
Ala Tyr Thr Cys Pro Tyr Gln Asn Val Met Asp Gly Val Leu Asn Tyr
            260                 265                 270 ccc att tac tat cca ctc ctc aac gcc ttc aag tca acc tcc ggc agc    864
Pro Ile Tyr Tyr Pro Leu Leu Asn Ala Phe Lys Ser Thr Ser Gly Ser
        275                 280                 285 atg gac gac ctc tac aac atg atc aac acc gtc aaa tcc gac tgt cca    912
Met Asp Asp Leu Tyr Asn Met Ile Asn Thr Val Lys Ser Asp Cys Pro
    290                 295                 300 gac tca aca ctc ctg ggc aca ttc gtc gag aac cac gac aac cca cgg    960
Asp Ser Thr Leu Leu Gly Thr Phe Val Glu Asn His Asp Asn Pro Arg
305                 310                 315                 320 ttc gct tct tac acc aac gac ata gcc ctc gcc aag aac gtc gca gca   1008
Phe Ala Ser Tyr Thr Asn Asp Ile Ala Leu Ala Lys Asn Val Ala Ala
                325                 330                 335 ttc atc atc ctc aac gac gga atc ccc atc atc tac gcc ggc caa gaa   1056
Phe Ile Ile Leu Asn Asp Gly Ile Pro Ile Ile Tyr Ala Gly Gln Glu
            340                 345                 350 cag cac tac gcc ggc gga aac gac ccc gcg aac cgc gaa gca acc tgg   1104
Gln His Tyr Ala Gly Gly Asn Asp Pro Ala Asn Arg Glu Ala Thr Trp
        355                 360                 365 ctc tcg ggc tac ccg acc gac agc gag ctg tac aag tta att gcc tcc   1152
Leu Ser Gly Tyr Pro Thr Asp Ser Glu Leu Tyr Lys Leu Ile Ala Ser
    370                 375                 380 gcg aac gca atc cgg aac tat gcc att agc aaa gat aca gga ttc gtg   1200
Ala Asn Ala Ile Arg Asn Tyr Ala Ile Ser Lys Asp Thr Gly Phe Val
385                 390                 395                 400 acc tac aag aac tgg ccc atc tac aaa gac gac aca acg atc gcc atg   1248
```

```
                Thr Tyr Lys Asn Trp Pro Ile Tyr Lys Asp Asp Thr Thr Ile Ala Met
                                405                 410                 415 cgc aag ggc aca gat ggg tcg cag atc gtg act atc ttg tcc aac aag        1296
Arg Lys Gly Thr Asp Gly Ser Gln Ile Val Thr Ile Leu Ser Asn Lys
            420                 425                 430 ggt gct tcg ggt gat tcg tat acc ctc tcc ttg agt ggt gcg ggt tac        1344
Gly Ala Ser Gly Asp Ser Tyr Thr Leu Ser Leu Ser Gly Ala Gly Tyr
        435                 440                 445 aca gcc ggc cag caa ttg acg gag gtc att ggc tgc acg acc gtg acg        1392
Thr Ala Gly Gln Gln Leu Thr Glu Val Ile Gly Cys Thr Thr Val Thr
    450                 455                 460 gtt ggt tcg gat gga aat gtg cct gtt cct atg gca ggt ggg cta cct        1440
Val Gly Ser Asp Gly Asn Val Pro Val Pro Met Ala Gly Gly Leu Pro
465                 470                 475                 480 agg gta ttg tat ccg act gag aag ttg gca ggt agc aag atc tgt agt        1488
Arg Val Leu Tyr Pro Thr Glu Lys Leu Ala Gly Ser Lys Ile Cys Ser
                485                 490                 495 agc tcg gga aga ggt gct aca agc ccg ggt ggc tcg tcg ggt agt gtc        1536
Ser Ser Gly Arg Gly Ala Thr Ser Pro Gly Gly Ser Ser Gly Ser Val
            500                 505                 510 gag gtc act ttc gac gtt tac gct acc aca gta tat ggc cag aac atc        1584
Glu Val Thr Phe Asp Val Tyr Ala Thr Thr Val Tyr Gly Gln Asn Ile
        515                 520                 525 tat atc acc ggt gat gtg agt gag ctc ggc aac tgg aca ccc gcc aat        1632
Tyr Ile Thr Gly Asp Val Ser Glu Leu Gly Asn Trp Thr Pro Ala Asn
    530                 535                 540 ggt gtt gca ctc tct tct gct aac tac ccc acc tgg agt gcc acg atc        1680
Gly Val Ala Leu Ser Ser Ala Asn Tyr Pro Thr Trp Ser Ala Thr Ile
545                 550                 555                 560 gct ctc ccc gct gac acg aca atc cag tac aag tat gtc aac att gac        1728
Ala Leu Pro Ala Asp Thr Thr Ile Gln Tyr Lys Tyr Val Asn Ile Asp
                565                 570                 575 ggc agc acc gtc atc tgg gag gat gct atc agc aat cgc gag atc acg        1776
Gly Ser Thr Val Ile Trp Glu Asp Ala Ile Ser Asn Arg Glu Ile Thr
            580                 585                 590 acg ccc gcc agc ggc aca tac acc gaa aaa gac act tgg gat gaa tct        1824
Thr Pro Ala Ser Gly Thr Tyr Thr Glu Lys Asp Thr Trp Asp Glu Ser
        595                 600                 605 tag                                                                    1827

<210> SEQ ID NO 40
<211> LENGTH: 608
<212> TYPE: PRT
<213> ORGANISM: Artificial sequence
<220> FEATURE:
<223> OTHER INFORMATION: Synthetic Construct

<400> SEQUENCE: 40

Met Val Ala Trp Trp Ser Leu Phe Leu Tyr Gly Leu Gln Val Ala Ala
1               5                   10                  15

Pro Ala Leu Ala Ala Thr Pro Ala Asp Trp Arg Ser Gln Ser Ile Tyr
            20                  25                  30

Phe Leu Leu Thr Asp Arg Phe Ala Arg Thr Asp Gly Ser Thr Thr Ala
        35                  40                  45

Thr Cys Asn Thr Ala Asp Gln Lys Tyr Cys Gly Gly Thr Trp Gln Gly
    50                  55                  60

Ile Ile Asp Lys Leu Asp Tyr Ile Gln Gly Met Gly Phe Thr Ala Ile
65                  70                  75                  80

Trp Ile Thr Pro Val Thr Ala Gln Leu Pro Gln Thr Thr Ala Tyr Gly
                85                  90                  95
```

```
Asp Ala Tyr His Gly Tyr Trp Gln Gln Asp Ile Tyr Ser Leu Asn Glu
            100                 105                 110

Asn Tyr Gly Thr Ala Asp Asp Leu Lys Ala Leu Ser Ser Ala Leu His
            115                 120                 125

Glu Arg Gly Met Tyr Leu Met Val Asp Val Val Ala Asn His Met Gly
            130                 135                 140

Tyr Asp Gly Ala Gly Ser Ser Val Asp Tyr Ser Val Phe Lys Pro Phe
145                 150                 155                 160

Ser Ser Gln Asp Tyr Phe His Pro Phe Cys Phe Ile Gln Asn Tyr Glu
                165                 170                 175

Asp Gln Thr Gln Val Glu Asp Cys Trp Leu Gly Asp Asn Thr Val Ser
            180                 185                 190

Leu Pro Asp Leu Asp Thr Thr Lys Asp Val Val Lys Asn Glu Trp Tyr
            195                 200                 205

Asp Trp Val Gly Ser Leu Val Ser Asn Tyr Ser Ile Asp Gly Leu Arg
            210                 215                 220

Ile Asp Thr Val Lys His Val Gln Lys Asp Phe Trp Pro Gly Tyr Asn
225                 230                 235                 240

Lys Ala Ala Gly Val Tyr Cys Ile Gly Glu Val Leu Asp Gly Asp Pro
                245                 250                 255

Ala Tyr Thr Cys Pro Tyr Gln Asn Val Met Asp Gly Val Leu Asn Tyr
            260                 265                 270

Pro Ile Tyr Tyr Pro Leu Leu Asn Ala Phe Lys Ser Thr Ser Gly Ser
            275                 280                 285

Met Asp Asp Leu Tyr Asn Met Ile Asn Thr Val Lys Ser Asp Cys Pro
290                 295                 300

Asp Ser Thr Leu Leu Gly Thr Phe Val Glu Asn His Asp Asn Pro Arg
305                 310                 315                 320

Phe Ala Ser Tyr Thr Asn Asp Ile Ala Leu Ala Lys Asn Val Ala Ala
                325                 330                 335

Phe Ile Ile Leu Asn Asp Gly Ile Pro Ile Ile Tyr Ala Gly Gln Glu
            340                 345                 350

Gln His Tyr Ala Gly Gly Asn Asp Pro Ala Asn Arg Glu Ala Thr Trp
            355                 360                 365

Leu Ser Gly Tyr Pro Thr Asp Ser Glu Leu Tyr Lys Leu Ile Ala Ser
            370                 375                 380

Ala Asn Ala Ile Arg Asn Tyr Ala Ile Ser Lys Asp Thr Gly Phe Val
385                 390                 395                 400

Thr Tyr Lys Asn Trp Pro Ile Tyr Lys Asp Asp Thr Thr Ile Ala Met
                405                 410                 415

Arg Lys Gly Thr Asp Gly Ser Gln Ile Val Thr Ile Leu Ser Asn Lys
            420                 425                 430

Gly Ala Ser Gly Asp Ser Tyr Thr Leu Ser Leu Ser Gly Ala Gly Tyr
            435                 440                 445

Thr Ala Gly Gln Gln Leu Thr Glu Val Ile Gly Cys Thr Thr Val Thr
            450                 455                 460

Val Gly Ser Asp Gly Asn Val Pro Val Pro Met Ala Gly Gly Leu Pro
465                 470                 475                 480

Arg Val Leu Tyr Pro Thr Glu Lys Leu Ala Gly Ser Lys Ile Cys Ser
                485                 490                 495

Ser Ser Gly Arg Gly Ala Thr Ser Pro Gly Gly Ser Gly Ser Val
            500                 505                 510

Glu Val Thr Phe Asp Val Tyr Ala Thr Thr Val Tyr Gly Gln Asn Ile
```

```
                  515                 520                 525
Tyr Ile Thr Gly Asp Val Ser Glu Leu Gly Asn Trp Thr Pro Ala Asn
            530                 535                 540

Gly Val Ala Leu Ser Ser Ala Asn Tyr Pro Thr Trp Ser Ala Thr Ile
545                 550                 555                 560

Ala Leu Pro Ala Asp Thr Thr Ile Gln Tyr Lys Tyr Val Asn Ile Asp
                565                 570                 575

Gly Ser Thr Val Ile Trp Glu Asp Ala Ile Ser Asn Arg Glu Ile Thr
            580                 585                 590

Thr Pro Ala Ser Gly Thr Tyr Thr Glu Lys Asp Thr Trp Asp Glu Ser
            595                 600                 605

<210> SEQ ID NO 41
<211> LENGTH: 640
<212> TYPE: PRT
<213> ORGANISM: Aspergillus kawachii
<220> FEATURE:
<221> NAME/KEY: mat_peptide
<222> LOCATION: (22)..(640)

<400> SEQUENCE: 41

Met Arg Val Ser Thr Ser Ser Ile Ala Leu Ala Val Ser Leu Phe Gly
        -20                 -15                 -10

Lys Leu Ala Leu Gly Leu Ser Ala Ala Glu Trp Arg Thr Gln Ser Ile
-5                   -1  1               5                  10

Tyr Phe Leu Leu Thr Asp Arg Phe Gly Arg Thr Asp Asn Ser Thr Thr
                15                  20                  25

Ala Thr Cys Asn Thr Gly Asp Gln Ile Tyr Cys Gly Gly Ser Trp Gln
            30                  35                  40

Gly Ile Ile Asn His Leu Asp Tyr Ile Gln Gly Met Gly Phe Thr Ala
        45                  50                  55

Ile Trp Ile Ser Pro Ile Thr Glu Gln Leu Pro Gln Asp Thr Ser Asp
60                  65                  70                  75

Gly Glu Ala Tyr His Gly Tyr Trp Gln Gln Lys Ile Tyr Tyr Val Asn
                80                  85                  90

Ser Asn Phe Gly Thr Ala Asp Asp Leu Lys Ser Leu Ser Asp Ala Leu
            95                 100                 105

His Ala Arg Gly Met Tyr Leu Met Val Asp Val Val Pro Asn His Met
        110                 115                 120

Gly Tyr Ala Gly Asn Gly Asn Asp Val Asp Tyr Ser Val Phe Asp Pro
125                 130                 135

Phe Asp Ser Ser Ser Tyr Phe His Pro Tyr Cys Leu Ile Thr Asp Trp
140                 145                 150                 155

Asp Asn Leu Thr Met Val Gln Asp Cys Trp Glu Gly Asp Thr Ile Val
                160                 165                 170

Ser Leu Pro Asp Leu Asn Thr Thr Glu Thr Ala Val Arg Thr Ile Trp
            175                 180                 185

Tyr Asp Trp Val Ala Asp Leu Val Ser Asn Tyr Ser Val Asp Gly Leu
        190                 195                 200

Arg Ile Asp Ser Val Glu Glu Val Pro Asp Phe Phe Pro Gly Tyr
205                 210                 215

Gln Glu Ala Ala Gly Val Tyr Cys Val Gly Glu Val Asn Gly Asn
220                 225                 230                 235

Pro Ala Leu Asp Cys Pro Tyr Gln Lys Tyr Leu Asp Gly Val Leu Asn
                240                 245                 250

Tyr Pro Ile Tyr Trp Gln Leu Leu Tyr Ala Phe Glu Ser Ser Ser Gly
```

```
                    255                 260                 265
Ser Ile Ser Asn Leu Tyr Asn Met Ile Lys Ser Val Ala Ser Asp Cys
            270                 275                 280

Ser Asp Pro Thr Leu Leu Gly Asn Phe Ile Glu Asn His Asp Asn Pro
285                 290                 295

Arg Phe Ala Ser Tyr Thr Ser Asp Tyr Ser Gln Ala Lys Asn Val Leu
300                 305                 310                 315

Ser Tyr Ile Phe Leu Ser Asp Gly Ile Pro Val Tyr Ala Gly Glu
                320                 325                 330

Glu Gln His Tyr Ser Gly Gly Asp Val Pro Tyr Asn Arg Glu Ala Thr
                335                 340                 345

Trp Leu Ser Gly Tyr Asp Thr Ser Ala Glu Leu Tyr Thr Trp Ile Ala
                350                 355                 360

Thr Thr Asn Ala Ile Arg Lys Leu Ala Ile Ser Ala Asp Ser Asp Tyr
        365                 370                 375

Ile Thr Tyr Lys Asn Asp Pro Ile Tyr Thr Asp Ser Asn Thr Ile Ala
380                 385                 390                 395

Met Arg Lys Gly Thr Ser Gly Ser Gln Ile Ile Thr Val Leu Ser Asn
                400                 405                 410

Lys Gly Ser Ser Gly Ser Ser Tyr Thr Leu Thr Leu Ser Gly Ser Gly
                415                 420                 425

Tyr Thr Ser Gly Thr Lys Leu Ile Glu Ala Tyr Thr Cys Thr Ser Val
        430                 435                 440

Thr Val Asp Ser Asn Gly Asp Ile Pro Val Pro Met Ala Ser Gly Leu
        445                 450                 455

Pro Arg Val Leu Leu Pro Ala Ser Val Val Asp Ser Ser Leu Cys
460                 465                 470                 475

Gly Gly Ser Gly Asn Thr Thr Thr Thr Thr Ala Ala Thr Ser Thr
                480                 485                 490

Ser Lys Ala Thr Thr Ser Ser Ser Ser Ser Ala Ala Ala Thr Thr
                495                 500                 505

Ser Ser Ser Cys Thr Ala Thr Ser Thr Thr Leu Pro Ile Thr Phe Glu
        510                 515                 520

Glu Leu Val Thr Thr Thr Tyr Gly Glu Glu Val Tyr Leu Ser Gly Ser
525                 530                 535

Ile Ser Gln Leu Gly Glu Trp His Thr Ser Asp Ala Val Lys Leu Ser
540                 545                 550                 555

Ala Asp Asp Tyr Thr Ser Ser Asn Pro Glu Trp Ser Val Thr Val Ser
                560                 565                 570

Leu Pro Val Gly Thr Thr Phe Glu Tyr Lys Phe Ile Lys Val Asp Glu
                575                 580                 585

Gly Gly Ser Val Thr Trp Glu Ser Asp Pro Asn Arg Glu Tyr Thr Val
                590                 595                 600

Pro Glu Cys Gly Ser Gly Ser Glu Thr Val Val Asp Thr Trp Arg
                605                 610                 615

<210> SEQ ID NO 42
<211> LENGTH: 505
<212> TYPE: PRT
<213> ORGANISM: Aspergillus niger
<220> FEATURE:
<221> NAME/KEY: mat_peptide
<222> LOCATION: (22)..(505)

<400> SEQUENCE: 42

Met Arg Leu Ser Thr Ser Ser Leu Phe Leu Ser Val Ser Leu Leu Gly
```

```
          -20             -15             -10
Lys Leu Ala Leu Gly Leu Ser Ala Ala Glu Trp Arg Thr Gln Ser Ile
 -5              -1   1               5                  10

Tyr Phe Leu Leu Thr Asp Arg Phe Gly Arg Thr Asp Asn Ser Thr Thr
             15              20              25

Ala Thr Cys Asp Thr Gly Asp Gln Ile Tyr Cys Gly Ser Trp Gln
         30              35              40

Gly Ile Ile Asn His Leu Asp Tyr Ile Gln Gly Met Gly Phe Thr Ala
         45              50              55

Ile Trp Ile Ser Pro Ile Thr Glu Gln Leu Pro Gln Asp Thr Ala Asp
 60              65              70              75

Gly Glu Ala Tyr His Gly Tyr Trp Gln Gln Lys Ile Tyr Asp Val Asn
                 80              85              90

Ser Asn Phe Gly Thr Ala Asp Asp Leu Lys Ser Leu Ser Asp Ala Leu
             95             100             105

His Ala Arg Gly Met Tyr Leu Met Val Asp Val Val Pro Asn His Met
            110             115             120

Gly Tyr Ala Gly Asn Gly Asn Asp Val Asp Tyr Ser Val Phe Asp Pro
            125             130             135

Phe Asp Ser Ser Ser Tyr Phe His Pro Tyr Cys Leu Ile Thr Asp Trp
140             145             150             155

Asp Asn Leu Thr Met Val Gln Asp Cys Trp Glu Gly Asp Thr Ile Val
                160             165             170

Ser Leu Pro Asp Leu Asn Thr Thr Glu Thr Ala Val Arg Thr Ile Trp
            175             180             185

Tyr Asp Trp Val Ala Asp Leu Val Ser Asn Tyr Ser Val Asp Gly Leu
            190             195             200

Arg Ile Asp Ser Val Leu Glu Val Glu Pro Asp Phe Phe Pro Gly Tyr
205             210             215

Gln Glu Ala Ala Gly Val Tyr Cys Val Gly Glu Val Asp Asn Gly Asn
220             225             230             235

Pro Ala Leu Asp Cys Pro Tyr Gln Lys Val Leu Asp Gly Val Leu Asn
            240             245             250

Tyr Pro Ile Tyr Trp Gln Leu Leu Tyr Ala Phe Glu Ser Ser Ser Gly
            255             260             265

Ser Ile Ser Asn Leu Tyr Asn Met Ile Lys Ser Val Ala Ser Asp Cys
            270             275             280

Ser Asp Pro Thr Leu Leu Gly Asn Phe Ile Glu Asn His Asp Asn Pro
            285             290             295

Arg Phe Ala Ser Tyr Thr Ser Asp Tyr Ser Gln Ala Lys Asn Val Leu
300             305             310             315

Ser Tyr Ile Phe Leu Ser Asp Gly Ile Pro Ile Val Tyr Ala Gly Glu
            320             325             330

Glu Gln His Tyr Ser Gly Gly Lys Val Pro Tyr Asn Arg Glu Ala Thr
            335             340             345

Trp Leu Ser Gly Tyr Asp Thr Ser Ala Glu Leu Tyr Thr Trp Ile Ala
            350             355             360

Thr Thr Asn Ala Ile Arg Lys Leu Ala Ile Ser Ala Asp Ser Ala Tyr
365             370             375

Ile Thr Tyr Ala Asn Asp Ala Phe Tyr Thr Asp Ser Asn Thr Ile Ala
380             385             390             395

Met Arg Lys Gly Thr Ser Gly Ser Gln Val Ile Thr Val Leu Ser Asn
            400             405             410
```

```
Lys Gly Ser Ser Gly Ser Ser Tyr Thr Leu Thr Leu Ser Gly Ser Gly
                415                 420                 425

Tyr Thr Ser Gly Thr Lys Leu Ile Glu Ala Tyr Thr Cys Thr Ser Val
            430                 435                 440

Thr Val Asp Ser Ser Gly Asp Ile Pro Val Pro Met Ala Ser Gly Leu
445                 450                 455

Pro Arg Val Leu Leu Pro Ala Ser Val Val Asp Ser Ser Ser Leu Cys
460                 465                 470                 475

Gly Gly Ser Gly Arg Leu Tyr Val Glu
                480

<210> SEQ ID NO 43
<211> LENGTH: 476
<212> TYPE: PRT
<213> ORGANISM: Aspergillus oryzae
<220> FEATURE:
<221> NAME/KEY: mat_peptide
<222> LOCATION: (1)..(476)

<400> SEQUENCE: 43

Ala Thr Pro Ala Asp Trp Arg Ser Gln Ser Ile Tyr Phe Leu Leu Thr
1               5                   10                  15

Asp Arg Phe Ala Arg Thr Asp Gly Ser Thr Thr Ala Thr Cys Asn Thr
            20                  25                  30

Ala Asp Gln Lys Tyr Cys Gly Gly Thr Trp Gln Gly Ile Ile Asp Lys
        35                  40                  45

Leu Asp Tyr Ile Gln Gly Met Gly Phe Thr Ala Ile Trp Ile Thr Pro
    50                  55                  60

Val Thr Ala Gln Leu Pro Gln Thr Thr Ala Tyr Gly Asp Ala Tyr His
65                  70                  75                  80

Gly Tyr Trp Gln Gln Asp Ile Tyr Ser Leu Asn Glu Asn Tyr Gly Thr
                85                  90                  95

Ala Asp Asp Leu Lys Ala Leu Ser Ser Ala Leu His Glu Arg Gly Met
            100                 105                 110

Tyr Leu Met Val Asp Val Val Ala Asn His Met Gly Tyr Asp Gly Ala
        115                 120                 125

Gly Ser Ser Val Asp Tyr Ser Val Phe Lys Pro Phe Ser Ser Gln Asp
    130                 135                 140

Tyr Phe His Pro Phe Cys Phe Ile Gln Asn Tyr Glu Asp Gln Thr Gln
145                 150                 155                 160

Val Glu Asp Cys Trp Leu Gly Asp Asn Thr Val Ser Leu Pro Asp Leu
                165                 170                 175

Asp Thr Thr Lys Asp Val Val Lys Asn Glu Trp Tyr Asp Trp Val Gly
            180                 185                 190

Ser Leu Val Ser Asn Tyr Ser Ile Asp Gly Leu Arg Ile Asp Thr Val
        195                 200                 205

Lys His Val Gln Lys Asp Phe Trp Pro Gly Tyr Asn Lys Ala Ala Gly
    210                 215                 220

Val Tyr Cys Ile Gly Glu Val Leu Asp Gly Asp Pro Ala Tyr Thr Cys
225                 230                 235                 240

Pro Tyr Gln Asn Val Met Asp Gly Val Leu Asn Tyr Pro Ile Tyr Tyr
                245                 250                 255

Pro Leu Leu Asn Ala Phe Lys Ser Thr Ser Gly Ser Met Asp Asp Leu
            260                 265                 270

Tyr Asn Met Ile Asn Thr Val Lys Ser Asp Cys Pro Asp Ser Thr Leu
        275                 280                 285
```

```
Leu Gly Thr Phe Val Glu Asn His Asp Asn Pro Arg Phe Ala Ser Tyr
    290                 295                 300
Thr Asn Asp Ile Ala Leu Ala Lys Asn Val Ala Ala Phe Ile Ile Leu
305                 310                 315                 320
Asn Asp Gly Ile Pro Ile Ile Tyr Ala Gly Gln Glu Gln His Tyr Ala
                325                 330                 335
Gly Gly Asn Asp Pro Ala Asn Arg Glu Ala Thr Trp Leu Ser Gly Tyr
            340                 345                 350
Pro Thr Asp Ser Glu Leu Tyr Lys Leu Ile Ala Ser Ala Asn Ala Ile
        355                 360                 365
Arg Asn Tyr Ala Ile Ser Lys Asp Thr Gly Phe Val Thr Tyr Lys Asn
    370                 375                 380
Trp Pro Ile Tyr Lys Asp Asp Thr Thr Ile Ala Met Arg Lys Gly Thr
385                 390                 395                 400
Asp Gly Ser Gln Ile Val Thr Ile Leu Ser Asn Lys Gly Ala Ser Gly
                405                 410                 415
Asp Ser Tyr Thr Leu Ser Leu Ser Gly Ala Gly Tyr Thr Ala Gly Gln
            420                 425                 430
Gln Leu Thr Glu Val Ile Gly Cys Thr Thr Val Thr Val Gly Ser Asp
        435                 440                 445
Gly Asn Val Pro Val Pro Met Ala Gly Gly Leu Pro Arg Val Leu Tyr
    450                 455                 460
Pro Thr Glu Lys Leu Ala Gly Ser Lys Ile Cys Ser
465                 470                 475
```